United States Patent [19]

Kamiya et al.

[11] 4,267,176

[45] May 12, 1981

[54] AMINO OR ACYLAMINO-SUBSTITUTED PYRIMIDINYL CEPHALOSPORANIC ACID DERIVATIVES AND PHARMACEUTICAL COMPOSITIONS THEREOF

[75] Inventors: Takashi Kamiya, Suita; Tsutomu Teraji, Toyonaka; Yoshiharu Nakai, Otsu; Kazuo Sakane, Amagasaki; Jiro Goto, Suita, all of Japan

[73] Assignee: Fujisawa Pharmaceutical Co., Ltd., Osaka, Japan

[21] Appl. No.: 32,778

[22] Filed: Apr. 24, 1979

Related U.S. Application Data

[63] Continuation-in-part of Ser. No. 960,226, Nov. 13, 1978, abandoned.

[30] Foreign Application Priority Data

Nov. 14, 1977 [GB]  United Kingdom ............... 47352/77
Apr. 27, 1978 [GB]  United Kingdom ............... 16810/78
Sep. 4, 1978 [GB]  United Kingdom ............... 35436/78

[51] Int. Cl.³ .................. A61K 31/545; C07D 501/56

[52] U.S. Cl. ..................... 424/246; 544/21; 544/25; 544/27; 544/28

[58] Field of Search ........................ 544/27; 424/246

[56] References Cited

U.S. PATENT DOCUMENTS

| | | | |
|---|---|---|---|
| 4,098,888 | 7/1978 | Ochiai et al. | 544/22 |
| 4,104,469 | 8/1978 | Naito et al. | 544/27 |
| 4,122,259 | 10/1978 | Humber | 424/246 |
| 4,152,433 | 5/1979 | Kamiya et al. | 424/246 |
| 4,166,115 | 8/1979 | Takaya et al. | 424/246 |

*Primary Examiner*—Paul M. Coughlan, Jr.
*Attorney, Agent, or Firm*—Oblon, Fisher, Spivak, McClelland & Maier

[57] ABSTRACT

The invention relates to novel amino or acylamino-substituted pyrimidinyl cephalosporanic acid derivatives and pharmaceutically acceptable salts thereof, of antibacterial activity, to processes for the preparation thereof, and to pharmaceutical compositions comprising the novel cephalosporanic acid derivatives.

25 Claims, No Drawings

AMINO OR ACYLAMINO-SUBSTITUTED PYRIMIDINYL CEPHALOSPORANIC ACID DERIVATIVES AND PHARMACEUTICAL COMPOSITIONS THEREOF

This invention is a continuation-in-part application of co-pending application Ser. No. 960,226 filed on Nov. 13, 1978, now abandoned.

The present invention relates to novel cephalosporanic acid derivatives and pharmaceutically acceptable salts thereof. More particularly, it relates to novel cephalosporanic acid derivatives and pharmaceutically acceptable salts thereof, which have anti-bacterial activities, to processes for the preparation thereof, to pharmaceutical composition comprising the same, and to a method of using the same therapeutically in the treatment of infectious diseases in human beings and animals.

Accordingly, one object of the present invention is to provide novel cephalosporanic acid derivatives and pharmaceutically acceptable salts thereof, which are highly active against a number of pathogenic bacteria.

Another object of the present invention is to provide processes for the preparation of novel cephalosporanic acid derivatives and pharmaceutically acceptable salts thereof.

A further object of the present invention is to provide pharmaceutical composition comprising, as an active ingredient, said cephalosporanic acid derivatives or its pharmaceutically acceptable salts.

Still further object of the present invention is to provide a method for the treatment of infectious diseases by pathogenic bacteria in human beings and animals.

The object cephalosporanic acid derivatives can be represented by the following general formula (I):

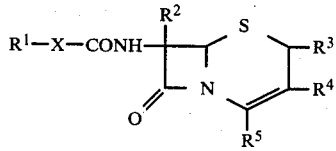

wherein $R^1$ is a group of the formula:

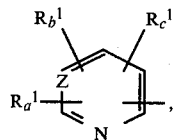

in which
$R_a^1$ is hydrogen, amino or a protected amino group,
$R_b^1$ and $R_c^1$ are each hydrogen, halogen, lower alkoxy or arylthio, and
Z is N or CH,
$R^2$ is hydrogen or lower alkoxy,
$R^3$ is hydrogen or lower alkyl,
$R^4$ is hydrogen, halogen, carbamoyloxymethyl, lower alkyl, lower alkoxy, lower alkanoyloxymethyl, lower alkanoylthiomethyl, or heterocyclic-thiomethyl which may have suitable substituent(s),
$R^5$ is carboxy or its derivative, and
X is lower alkylene or a group of the formula:

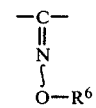

in which $R^6$ is hydrogen or an organic residue which may have suitable substituent(s), and non-toxic, pharmaceutically acceptable salts thereof.

In the object compounds (I) and the corresponding starting compounds (III) of Process 1 mentioned below, the partial structure represented by the formula:

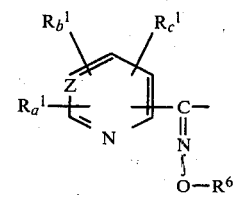

is to be understood to include both of the geometrical structures represented by the formula:

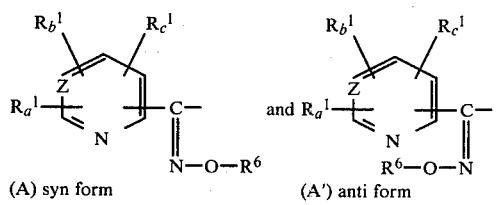

(A) syn form    (A') anti form

Accordingly, with regard to the compounds having the above mentioned partial structure, the compounds having the geometrical structure shown by the formula (A) are referred to as "syn isomer" and the other compounds having the alternative one shown by the formula (A') as "anti isomer" in this specification.

Suitable pharmaceutically acceptable salts of the object compounds (I) are conventional non-toxic salts and may include an inorganic salt, for example, a metal salt such as an alkali metal salt (e.g., sodium salt, potassium salt, etc.) and an alkaline earth metal salt (e.g., calcium salt, magnesium salt, etc.), and an ammonium salt etc.; an organic salt, for example, an organic amine salt (e.g., trimethylamine salt, triethylamine salt, pyridine salt, picoline salt, dicyclohexylamine salt, N,N'-dibenzylethylenediamine salt, N-methylglucamine salt, diethanolamine salt, triethanolamine salt, tris(hydroxymethylamino)methane salt, etc.) etc.; an organic carboxylic or sulfonic acid addition salt (e.g., formate, acetate, maleate, tartrate, methanesulfonate, benzenesulfonate, toluenesulfonate, etc.); an inorganic acid addition salt (e.g., hydrochloride, hydrobromide, sulfate, phosphate, etc.); a salt with a basic or acidic amino acid (e.g., arginine, aspartic acid, glutamic acid, etc.), and the like.

According to the present invention, the object compounds (I) and the pharmaceutically acceptable salts thereof can be prepared by the processes as illustrated by the following schemes.

Process 1:

-continued

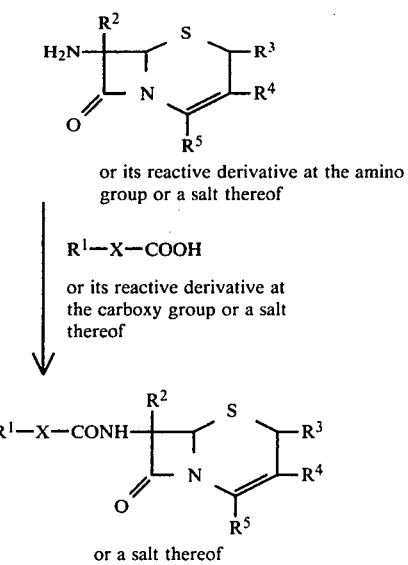

or its reactive derivative at the amino group or a salt thereof

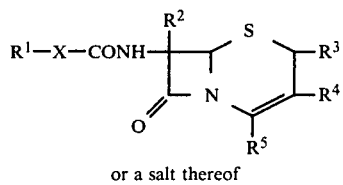

or its reactive derivative at the carboxy group or a salt thereof (I)

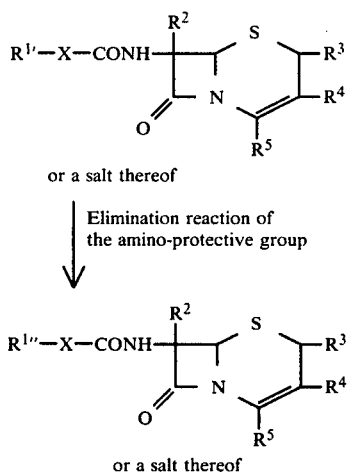

or a salt thereof

Process 2:

(Ia)

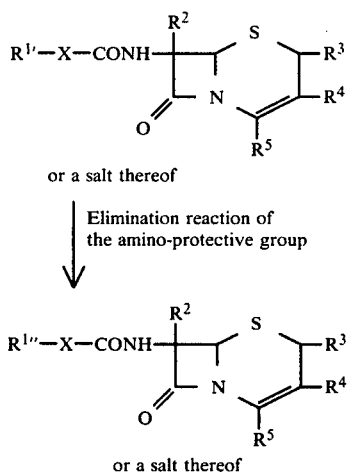

or a salt thereof

Elimination reaction of the amino-protective group (Ib)

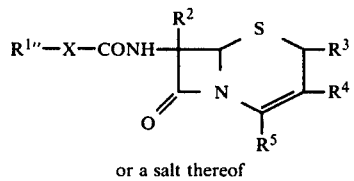

or a salt thereof

Process 3:

(Ic)

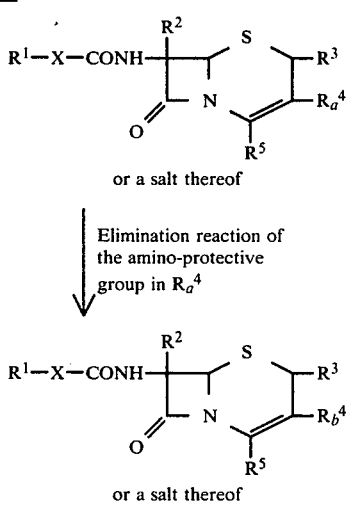

or a salt thereof

Elimination reaction of the amino-protective group in $R_a^4$ (Id)

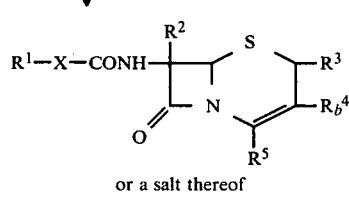

or a salt thereof

Process 4:

(Ie)

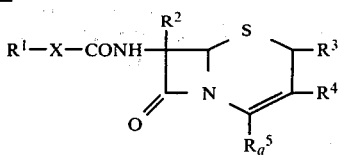

or a salt thereof

Elimination reaction of the carboxy-protective group (If)

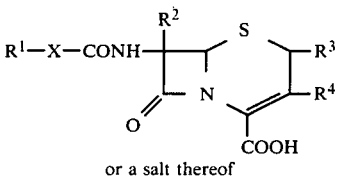

or a salt thereof

Process 5:

(Ig)

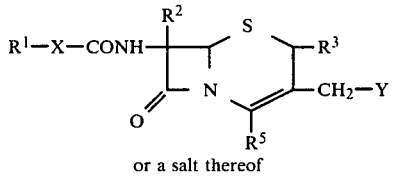

or a salt thereof

H—$R^7$
or a reactive derivative thereof (IV)

(Ih)

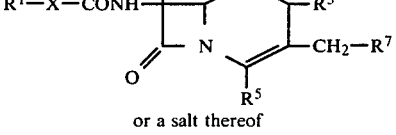

or a salt thereof wherein $R^1$, $R^2$, $R^3$, $R^4$, $R^5$ and X are each as defined above, and $R^{1\prime}$ is a group of the formula:

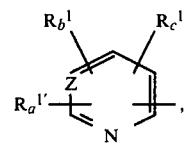

in which $R_a^{1\prime}$ is a protected amino group, and $R_b^1$, $R_c^1$ and Z are each as defined above, $R^{1\prime\prime}$ is a group of the formula:

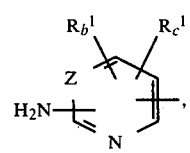

in which $R_b^1$, $R_c^1$ and Z are each as defined above, $R_a^4$ is heterocyclic-thiomethyl having a protected amino(lower)alkyl group, $R_b^4$ is heterocyclic-thiomethyl having a amino(lower-)alkyl group, $R_a^5$ is a protected carboxy group, $R^7$ is heterocyclic-thio which may have suitable substituents, and Y is a conventional group which is capable to be replaced by the residue ($-R^7$) of the compound of the formula: $HR^7$ in which $R^7$ is as defined above.

Some of the starting compound (III) in Process 1 are novel and can be prepared, for example, from the known compounds (A-1), (B-1), (C-1a) and (D-1a) by the Processes A to Q as illustrated by the following reaction schemes or a similar manner thereto.

The compounds (A-1), (B-1), (C-1a) and (D-1a) are disclosed, for example, in the following literatures.

Compound (A-1):

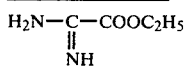

(Journal of Organic Chemistry, Vol.27, page 3608)

Compound (B-1):

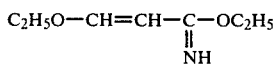

(Journal of the American Chemical Society, Vol.69, page 2657 (1949).

Compound (C-1a):

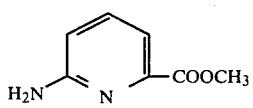

(Chemical Abstract Vol.54, 6709)

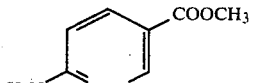

(Chemical Abstract Vol.52, 7313g)

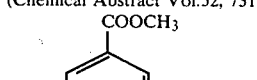

(Chemical Abstract Vol.53, 7162c)

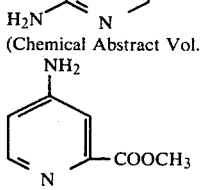

(Journal fur Praktische Chemie Reihe 4, Vol.13, page 58, 1961)

Compound (D-1a)

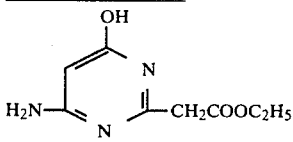

(Abstracts of the 9th Congress of Heterocyclic Chemistry, page 146, Fukuoka, Japan, 1976)

Process A:

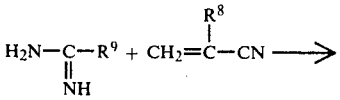

or a salt thereof (A-1)   (A-2)

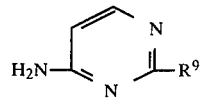

or a salt thereof (A-3)

Process B:

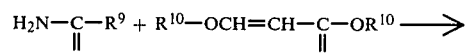

or a salt thereof (A-1)    or a salt thereof (B-1)

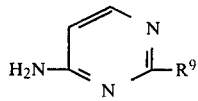

or a salt thereof (B-2)

Process C:

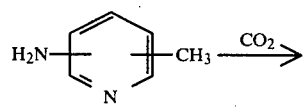

or a salt thereof (C-1)

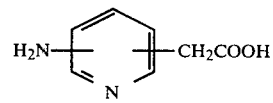

or a salt thereof (C-2)

Process D:

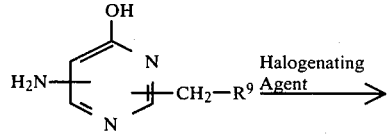

or a salt thereof (D-1)

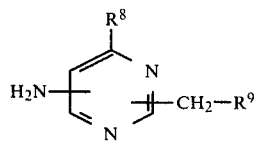

or a salt thereof (D-2)

Process E:

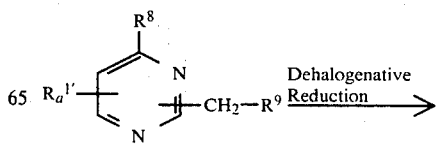

(E-1)

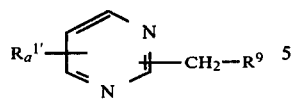
(E-2)
Process F:
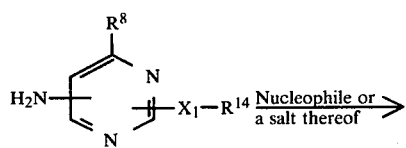
or a salt thereof
(F-1)
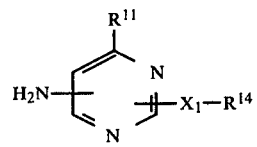
or a salt thereof
(F-2)
Process G:
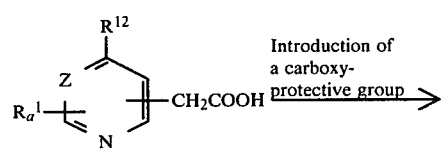
or a salt thereof
(G-1)
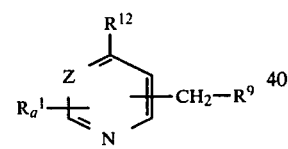
or a salt thereof
(G-2)
Process H:
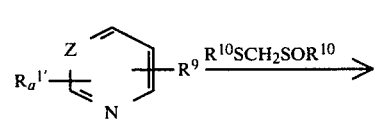
(H-1)
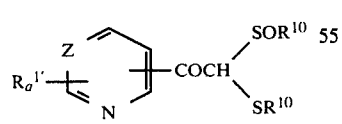
(H-2)
Process I:
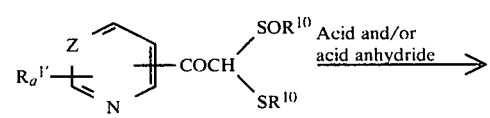
(H-2)
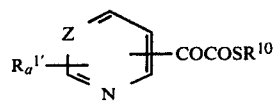
(I-1)
Process J:
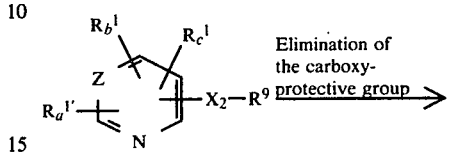
(J-1)
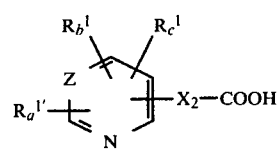
or a salt thereof
(J-2)
Process K:
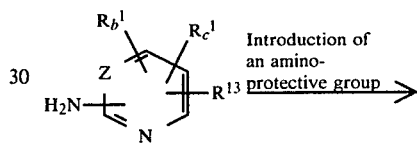
(K-1)
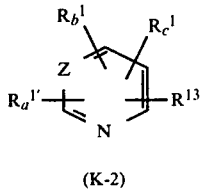
(K-2)
Process L:
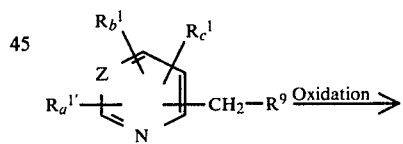
(L-1)
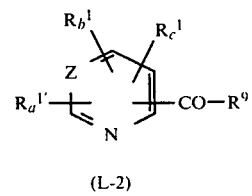
(L-2)
Process M:
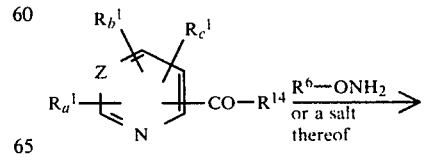
or its hydrate,
or a salt thereof
(M-1)

-continued

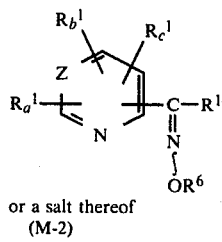

or a salt thereof
(M-2)

Process N:

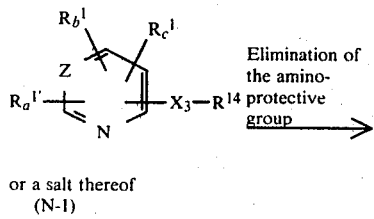

or a salt thereof
(N-1)

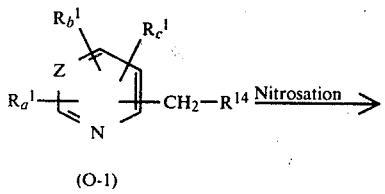

or a salt thereof
(N-2)

Process O:

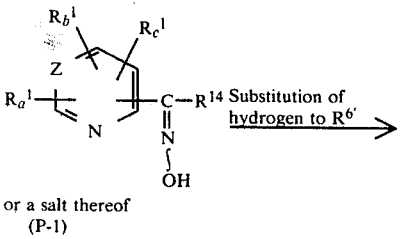

(O-1)

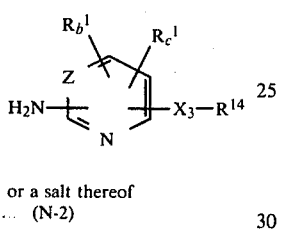

(O-2)

Process P:

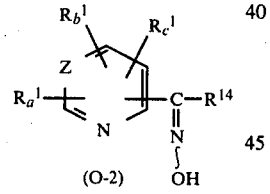

or a salt thereof
(P-1)

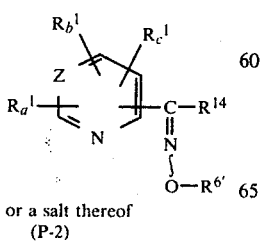

or a salt thereof
(P-2)

Process Q:

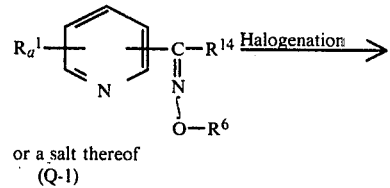

or a salt thereof
(Q-1)

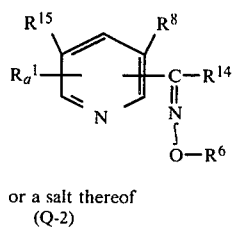

or a salt thereof
(Q-2)

wherein
$R_a^{1'}$, $R_b^1$, $R_c^1$, $R^6$ and Z are each as defined above, and
$R^{6'}$ is an organic residue which may have suitable substituent(s),
$R^8$ is halogen,
$R^9$ is a protected carboxy group,
$R^{10}$ is lower alkyl,
$R^{11}$ is lower alkoxy or arylthio,
$R^{12}$ is hydrogen or lower alkyl,
$R^{13}$ is a protected carboxy group, or a group of the formula $$-X_4-R^{14}$$

or

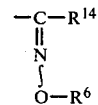

in which
$X_4$ is lower alkylene,
$R^6$ is as defined above and
$R^{14}$ is as defined below,
$R^{14}$ is carboxy or a protected carboxy group,
$R^{15}$ is hydrogen or halogen,
$X_1$ is lower alkylene or a group of the formula:

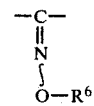

in which $R^6$ is as defined above,
$X_2$ is lower alkylene, or a group of the formula:

$$-CO-$$

or

in which $R^6$ is as defined above, and
$X_3$ is a group of the formula:

—CO— or

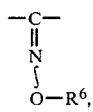

in which $R^6$ is as defined above.

In the above and subsequent description of the present specification, suitable examples and illustration of the various definitions which the present invention intends to include within the scope thereof are explained in detail as follows.

The term "lower" is intended to mean a group having 1 to 6 carbon atoms, unless otherwise provided.

Suitable "protective group" in the terms "a protected amino group" and "a protected amino(lower)alkyl group" may include an acyl and the other conventional protective group such as ar(lower)alkyl (e.g., benzyl, trityl, diphenylmethyl, etc.), substituted phenylthio (e.g. 2-nitrophenylthio, etc.), substituted aralkylidene (e.g. 4-nitrobenzylidene, etc.), substituted alkylidene (e.g. 1-methoxycarbonyl-2-propylidene, etc.), substituted lower cycloalkylidene (e.g. 2-ethoxycarbonylcyclohexylidene, etc.), and the like. And suitable acyl group may be the ones derived from carboxylic, sulfonic or carbamic acid, and more particularly substituted or unsubstituted carbamoyl aliphatic acyl, and acyl having an aromatic ring (referred to as aromatic acyl) or heterocyclic ring (referred to as heterocyclic acyl.)

Suitable examples of the aliphatic acyl may be lower alkanoyl (e.g., formyl, acetyl, propionyl, butyryl, isobutyryl, isovaleryl, oxalyl, succinyl, pivaloyl, etc.); lower cycloalkanecarbonyl (e.g. cyclopentanecarbonyl, cyclohexanecarbonyl, etc.); lower alkoxycarbonyl (e.g., methoxycarbonyl, ethoxycarbonyl, propoxycarbonyl, isopropoxycarbonyl, butoxycarbonyl, tert-butoxycarbonyl, pentyloxycarbonyl, tert-pentyloxycarbonyl, hexyloxycarbonyl, etc.); lower cycloalkyl(lower)alkoxycarbonyl (e.g., 1-cyclopropylethoxycarbony, etc.); lower alkoxyalkanoyl (e.g., methoxyacetyl, ethoxyacetyl, methoxypropionyl, etc.); and lower alkanesulfonyl (e.g., mesyl, ethanesulfonyl, propanesulfonyl, butanesulfonyl, etc.).

Suitable examples of the aromatic acyl may be ar(lower)alkanoyl (e.g., phenylacetyl, phenylpropionyl, etc.); ar(lower)alkoxycarbonyl (e.g., benzyloxycarbonyl, phenethyloxycarbonyl, etc.); arenesulfonyl (e.g., benzenesulfonyl, tosyl, etc.); and aroyl (e.g., benzoyl, toluoyl, naphthoyl, phthaloyl, indancarbonyl, etc.).

Suitable examples of the heterocyclic acyl may be heterocyclic(lower)alkanoyl (e.g., thienylacetyl, furylacetyl, pyrrolylacetyl, thiadiazolylacetyl, tetrazolylacetyl, piperazinylacetyl, etc.); heterocyclicoxycarbonyl (e.g. 8-quinolyloxycarbonyl, etc.); heterocycliccarbonyl (e.g., thenoyl, furoyl, nicotinoyl, isonicotinoyl, pyrrolecarbonyl, pyrrolidinecarbonyl, tetrahydropyrancarbonyl, etc.); heterocyclic-(lower)alkoxycarbonyl (e.g. 2-pyridylmethoxycarbonyl, etc.).

Suitable substituted or unsubstituted carbamoyl may include carbamoyl, lower alkylcarbamoyl (e.g., methylcarbamoyl, ethylcarbamoyl, etc.), arylcarbamoyl (e.g., phenylcarbamoyl, etc.), ar(lower)alkylcarbamoyl (e.g., benzylcarbamoyl, tritylcarbamoyl, etc.), lower alkanoylcarbamoyl (e.g., formylcarbamoyl, acetylcarbamoyl, etc.), mono(or di or tri)halo(lower)alkanoylcarbamoyl (e.g., chloroacetylcarbamoyl, trichloroacetylcarbamoyl, etc.), and the like.

The "acyl" as stated above may optionally have 1 to 3 suitable substituent(s) such as halogen (e.g., chlorine, bromine, iodine or fluorine), hydroxy, cyano, nitro, lower alkoxy, lower alkyl, lower alkenyl, acyl[preferable mono(or di or tri)halo(lower)alkanoyl (e.g., chloroacetyl, dichloroacetyl, trichloroacetyl, trifluoroacetyl, etc.)], aryl (e.g., phenyl, tolyl, etc.), or the like.

Preferable examples of said "protective group" in the terms "a protected amino group" and "a protected amino(lower)alkyl group" are acyl, and more preferably lower alkanoyl (e.g., formyl, acetyl, propionyl, butyryl, isobutyryl, isovaleryl, oxalyl, succinyl, pivaloyl, etc.), mono (or di or tri)halo(lower)-alkanoyl (e.g., chloroacetyl, dichloroacetyl, trichloroacetyl, trifluoroacetyl, etc.) and lower alkoxycarbonyl (e.g., methoxycarbonyl, ethoxycarbonyl, propoxycarbonyl, isopropoxycarbonyl, butoxycarbonyl, tert-butoxycarbonyl, pentyloxycarbonyl, tert-pentyloxycarbonyl, hexyloxycarbonyl, etc.).

Suitable "lower alkyl" may include straight or branched saturated aliphatic hydrocarbon residue such as methyl, ethyl, propyl, isopropyl, butyl, isobutyl, tert-butyl, pentyl, neopentyl, tert-pentyl, hexyl, and the like, and preferably one having 1 to 4 carbon atoms.

Suitable "organic residue which may have suitable substituent(s)" may include:

lower alkyl (e.g., methyl, ethyl, propyl, isopropyl, butyl, isobutyl, tert-butyl, pentyl, neopentyl, tert-pentyl, hexyl, etc.);

mono(or di or tri)halo(lower)alkyl (e.g., chloromethyl, dichloromethyl, trichloromethyl, bromomethyl, chloroethyl, dichloroethyl, trichloroethyl, fluoroethyl, trifluoroethyl, etc.);

lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.);

lower alkynyl (e.g., ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, etc.);

aryl (e.g., phenyl, tolyl, xylyl, cumenyl, naphthyl, etc.);

ar(lower)alkyl such as phenyl(lower)alkyl (e.g., benzyl, phenethyl, phenylpropyl, etc.); and the like.

halo(lower)alkanoyl (e.g. chloroacetyl, dichloroacetyl, etc.); and the like.

Suitable "lower alkoxy" may be straight or branched and include methoxy, ethoxy, propoxy, isopropoxy, butoxy, isobutoxy, t-butoxy, pentyloxy, neopentyloxy, hexyloxy and the like, and preferably one having 1 to 4 carbon atoms.

Suitable "halogen" may be chlorine, bromine, iodine or fluorine.

Suitable "lower alkanoyloxylmethyl" may include acetoxymethyl, propionyloxymethyl, butyryloxymethyl, isobutyryloxymethyl, valeryloxymethyl, isovaleryloxymethyl, pivaloyloxymethyl, hexanoyloxymethyl and the like.

Suitable "lower alkanoylthiomethyl" may include acetylthiomethyl, propionylthiomethyl, butyrylthiomethyl, isobutyrylthiomethyl, valerylthiomethyl, isovalerylthiomethyl, pivaloylthiomethyl, hexanoylthiomethyl, and the like.

Suitable "heterocyclic moiety" in the terms "heterocyclicthiomethyl which may have suitable substituent(s)" and "heterocyclic-thio which may have suitable substituent(s)" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl and its N-oxide, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 6-membered heteromonocyclic group containing 1 to 4 nitrogen atoms (e.g., pyrrolidinyl, imidazolidinyl, piperidino, piperazinyl, etc.);

unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.;

unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 6-membered heteromonocyclic group containing 1 to 2 oxygen atoms and 1 to 3 nitrogen atoms (e.g., morpholinyl, etc.);

unsaturated condensed heterocyclic group containing 1 to 2 oxygen atoms and 1 to 3 nitrogen atoms (e.g., benzoxazolyl, benzoxadiazolyl, etc.);

unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.), etc.;

saturated 3 to 6-membered heteromonocyclic group containing 1 to 2 sulfur atoms and 1 to 3 nitrogen atoms (e.g., thiazolidinyl, etc.);

unsaturated condensed heterocyclic group containing 1 to 2 sulfur atoms and 1 to 3 nitrogen atoms (e.g., benzothiazolyl, benzothiadiazolyl, etc.) and the like; wherein said heterocyclic group may have 1 to 4 suitable substituents selected from lower alkyl or lower cycloalkyl (e.g., methyl, ethyl, propyl, isopropyl, butyl, isobutyl, pentyl, cyclopentyl, hexyl, cyclohexyl, etc.); lower alkenyl (e.g. vinyl, allyl, 1 or 2 or 3-propenyl, 1 or 2 or 3 or 4-butenyl, 1 or 2 or 3 or 4 or 5-pentenyl, etc.); amino(lower)alkyl (e.g., aminomethyl, 2-aminoethyl, 2-aminopropyl, 3-aminopropyl, 4-aminobutyl, 5-aminopentyl, 6-aminohexyl, etc.); a protected amino(lower)alkyl group such as lower alkoxycarbonylamino(lower)alkyl (e.g. tert-butoxycarbonylaminomethyl, etc.); carboxy(lower)alkyl (e.g., carboxymethyl, 2-carboxyethyl, 2-carboxypropyl, 3-carboxypropyl, 4-carboxybutyl, 5-carboxypentyl, 6-carboxyhexyl, etc.); sulfo(lower)alkyl (e.g., sulfomethyl, 2-sulfoethyl, 2-sulfopropyl, 3-sulfopropyl, 4-sulfobutyl, 5-sulfopentyl, 6-sulfohexyl, etc.); phenyl which may have 1 to 3 halogen atom(s) (e.g. phenyl, 2 or 3 or 4-chlorophenyl, 2 or 3 or 4-bromophenyl, etc.); and lower alkylamino(lower)alkyl (e.g., N-methylaminomethyl, N,N-dimethylaminomethyl, 2-(N-methylamino)ethyl, 2-(N,N-dimethylamino)ethyl, 2-(N-methyl-N-ethylamino)ethyl, 3-(N-methylamino)propyl, 3-(N,N-dimethylamino)propyl, 3-(N,N-diethylamino)propyl, 4-(N-methylamino)butyl, 4-(N,N-dimethylamino)butyl, 4-(N-methyl-N-ethylamino)butyl, 5-(N-methylamino)pentyl, 5-(N,N-dimethylamino)pentyl, 6-(N,N-diethylamino)hexyl, 6-(N,N-dimethylamino)hexyl, etc.).

And preferable examples of said "heterocyclic moiety" are:

thiadiazolyl (e.g., 1,2,4-thiadiazolyl, 1,3,4-thiadiazolyl, 1,2,5-thiadiazolyl, etc.) which may have a substituent selected from the groups consisting of lower alkyl (e.g., methyl, ethyl, propyl, isopropyl, butyl, pentyl, hexyl, etc.), amino(lower)alkyl (e.g., aminomethyl, aminoethyl, aminopropyl, etc.) and lower alkoxycarbonylamino(lower)alkyl (e.g., methoxycarbonylaminomethyl, tert-butoxycarbonylaminomethyl, ethoxycarbonylaminoethyl, etc.);

oxadiazolyl (e.g., 1,2,4-oxadiazolyl, 1,3,4-oxadiazolyl, 1,2,5-oxadiazolyl, etc.) which may have halophenyl (e.g., 2-chlorophenyl,4-chlorophenyl,4-bromophenyl, etc.);

tetrazolyl (e.g., 1H-tetrazolyl, 2H-tetrazolyl,) which may have a substituent selected from the groups consisting of lower alkyl (e.g., methyl, ethyl, propyl, isopropyl, butyl, pentyl, hexyl, etc.), carboxy(lower)alkyl (e.g., carboxymethyl, carboxyethyl, carboxypropyl, etc.), lower alkenyl (e.g., vinyl, allyl, etc.) and amino(lower)alkyl (e.g., aminomethyl, 2-aminoethyl, 2-aminopropyl, 3-aminopropyl, 4-aminobutyl, 5-aminopentyl, 6-aminohexyl, etc.);

pyrazinyl; and tetrazolopyridazinyl (e.g., tetrazolo[1,5-b]pyridazinyl, etc.).

"Heterocyclic" moiety in the terms "heterocyclic-thiomethyl having a protected amino(lower)alkyl group" and "heterocyclic-thiomethyl having an amino(lower)alkyl group" may be the same as exemplified above, and thus defined heterocyclic moiety is preferably lower alkoxycarbonylamino(lower)alkylthiadiazolyl and amino(lower)alkylthiadiazolyl as aforementioned, respectively.

Suitable "lower alkylene" may include methylene, ethylene, trimethylene, 1-methylethylene, etc., preferably one having 1 to 3 carbon atoms, more preferably one having 1 to 2 carbon atoms and the most preferably methylene.

Suitable "carboxy derivative" includes protected carboxy such as esterified carboxy. And suitable examples of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g., vinyl ester, allyl ester, etc.);

lower alkynyl ester (e.g., ethynyl ester, propynyl ester, etc.);

lower alkoxyalkyl ester (e.g., methoxymethyl ester, ethoxymethyl ester, isopropoxymethyl ester, 1-methoxyethyl ester, 1-ethoxyethyl ester, etc.); lower alkylthioalkyl ester (e.g., methylthiomethyl ester, ethylthiomethyl ester, ethylthioethyl ester, isopropylthiomethyl ester, etc.);

mono (or di or tri)-halo(lower)alkyl ester (e.g., 2-iodoethyl ester, 2,2,2-trichloroethyl ester, etc.); lower alkanoyloxy(lower)alkyl ester (e.g., acetoxymethylester, proionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g., mesylmethyl ester, 2-mesylethyl ester etc.);

ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-di-t-butylbenzyl ester, etc.);

aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester;

lower alkylthioester (e.g. methylthioester, ethylthioester, etc.) and the like.

Suitable "a protected carboxy group" may include esterified carboxy as aforementioned.

Suitable "a conventional group which is capable to be replaced by the residue (—R$^7$) of the compound of the formula: HR$^7$" in the symbol Y may include halogen (e.g., chlorine, bromine, etc.), azido, acyloxy such as lower alkanoyloxy (e.g., formyloxy, acetoxy, propionyloxy, butyryloxy, etc.), and the like.

Suitable "arylthio" may include phenylthio, tolylthio, xylylthio, mesitylthio, naphthylthio and the like.

The processes for preparing the object compounds (I) of the present invention are explained in detail in the following.

Process 1

The object compound (I) or a salt thereof can be prepared by reacting a 7-aminocephalosporanic acid derivative (II) or its reactive derivative at the amino group or a salt thereof with a carboxylic acid (III) or its reactive derivative at the carboxy group or a salt thereof.

As to the starting compounds to be used in this process, the 7-aminocephalosporanic acid derivatives (II) have been publicly known and can be prepared by the method known to the art in the cephalosporin field, and the carboxylic acid (III) can be prepared according to a manner as disclosed in Processes A to Q.

Suitable reactive derivative at the amino group of the compound (II) may include a conventional reactive derivative used in amidation reaction, for example, a silyl derivative formed by the reaction of the compound (II) with a silyl compound such as bis(trimethylsilyl)acetamide, trimethylsilylacetamide, etc.; isocyanato, isothiocyanato, etc.; Schiff's base or its tautomeric enamine type isomer formed by the reaction of the amino group with a carbonyl compound such as an aldehyde compound (e.g., acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc.) or a ketone compound (e.g., acetone, methyl ethyl ketone, methyl isobutyl ketone, acetylacetone, ethyl acetoacetate, etc.), and the like.

Suitable derivatives at the carboxy group of the compound (II) and suitable salts of the compound (II) are to be referred to the ones exemplified for the compound (I).

Suitable reactive derivatives at the carboxy group of the compound (III) may include, for example, an acid halide, an acid anhydride, an activated amide, an activated ester, and the like, and preferably an acid chloride and acid bromide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g., methyl carbonate, ethyl carbonate, propyl carbonate, etc.), aliphatic carboxylic acid (e.g., pivalic acid, pentanoic acid, isopentanoic acid, 2-ethylbutyric acid, trichloroacetic acid, etc.), aromatic carboxylic acid (e.g., benzoic acid, etc.); a symmetrical acid anhydride; an activated acid amide with a heterocyclic compound contained imino function such as imidazole, 4-substituted imidazole, dimethylpyrazole, triazole or tetrazole; an activated ester (e.g., cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidinylester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like. The suitable reactive derivative can optionally be selected from the above according to the kind of the compound (III) to be used practically.

Suitable salts of the compound (III) may include a salt with an inorganic base such as an alkali metal salt (e.g., sodium or potassium salt), an alkaline earth metal salt (e.g., calcium or magnesium salt), a salt with an organic base such as trimethylamine, triethylamine, an acid addition salt (e.g., hydrochloride), and the like.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water. The reaction can be usually carried out under cooling.

When the carboxylic acid (III) is used in a form of the free acid or salt in this reaction, the reaction is preferably carried out in the presence of a condensing agent such as a carbodiimide compound (e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a ketenimine compound (e.g., N,N'-carbonylbis(2-methylimidazole), pentamethyleneketene-N-cyclohexylimine, diphenylketene-N-cyclohexylimine, etc.); an olefinic or acetylenic ether compounds (e.g., ethoxyacetylene), β-chlorovinylethyl ether, a sulfonic acid ester of N-hydroxybenzotriazole derivative (e.g., 1-(4-chlorobenzenesulfonyloxy)-6-chloro-1H-benzotriazole, etc.), a phosphorus compound (e.g., trialkyl phosphite, ethyl polyphosphate, isopropyl polyphosphate, phosphoryl chloride, phosphorus trichloride, triphenylphosphine, etc.), thionyl chloride, oxalyl chloride, N-ethyl-benzisoxazolium salt, N-ethyl-5-phenylisoxazolium-3-sulfonate, a reagent (referred to as so-called "Vilsmeier reagent") formed by the reaction of an amide compound such as dimethylformamide, diethylacetamide, N-methylformamide or the like with a halogen compound such as thionyl chloride, phosphoryl chloride, phosgene or the like.

Process 2

The object compound (Ib) or a salt thereof can be prepared by subjecting the compound (Ia) or a salt thereof to elimination reaction of the amino-protective group.

The elimination reaction is carried out by a conventional method such as hydrolysis, reduction or the like.

These methods may be selected depending on the kind of the protecting group to be eliminated.

The hydrolysis may include a method being conducted in the presence of an acid (referred to as acidic hydrolysis hereinafter), base (referred to as basic hydrolysis hereinafter), hydrazine, or the like.

Among these methods, acidic hydrolysis is one of the common and preferable method for eliminating the protective group such as substituted or unsubstituted alkoxycarbonyl (e.g., t-butoxycarbonyl, t-pentyloxycarbonyl, trichloroethoxycarbonyl, etc.), substituted or unsubstituted alkanoyl (e.g., formyl, etc.) lower cycloalkoxycarbonyl, substituted or unsubstituted ar(-lower)alkoxycarbonyl (e.g., benzyloxycarbonyl, substituted henzyloxycarbonyl, etc.), ar(lower)alkyl (e.g., benzyl, trityl, etc.), substituted phenylthio, substituted aralkylidene, substituted alkylidene, substituted lower cycloalkylidene, or the like. Suitable acid for the hydrolysis includes an organic or an inorganic acid, for example, formic acid, trifluoroacetic acid, benzenesulfonic acid, p-toluenesulfonic acid, hydrochloric acid and the like. Preferable acid is one which can easily be removed from the reaction mixture by a conventional manner such as distillation under reduced pressure, for example, formic acid, trifluoroacetic acid, hydrochloric acid, etc. The acid suitable for the reaction can be selected according to the kind of protective group to be eliminated, and the elimination reaction can be carried out in the presence or absence of a solvent. Suitable solvent includes a conventional organic solvent, water or a mixture thereof. When the hydrolysis is carried out in the presence of trifluoroacetic acid, the reaction may be preferably carried out in the presence of anisole.

The basic hydrolysis is preferable applied for eliminating the protective group such as haloalkanoyl (e.g., trifluoroacetyl, etc.), etc. Suitable base includes, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonte, etc.), alkaline earth metal carbonate (e.g., magnesium carbonate, calcium carbonate, etc.), alkali metal bicarbonate (e.g., sodium bicarbonate, potassium bicarbonate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as alkali metal acetate (e.g., sodium acetate, potassium acetate, etc.), alkali metal alkoxide (e.g., sodium methoxide, sodium ethoxide, sodium propoxide, etc.), trialkylamine (e.g., trimethylamine, triethylamine, etc.), picoline, N-methylpyrrolidine, N-methylmorpholine, 1,5-diazabicyclo[4,3,0]-5-nonene, 1,4-diazabicyclo[2,2,2]octane, 1,5-diazabicyclo[5,4,0]-5-undecane or the like. The basic hydrolysis is often carried out in water or a hydrophilic or moistened organic solvent or a miture thereof.

The hydrolysis using hydrazine is commonly applied for eliminating the protective group such as succinyl or phthaloyl.

The protecting group can generally be eliminated by hydrolysis as mentioned above or by the other conventional hydrolysis. In case that the protective group is halo(lower)alkoxycarbonyl or 8-quinolyloxycarbonyl, they are eliminated preferably by treating with a heavy metal such as copper, zinc or the like.

The reductive elimination is generally applied for eliminating the protective group such as halo(lower)alkoxycarbonyl (e.g., trichloroethoxycarbonyl etc.), substituted or unsubstituted aralkoxycarbonyl (e.g., benzyloxycarbonyl, substituted benzyloxycarbonyl etc.), 2-pyridylmethoxycarbonyl, benzyl, etc. Suitable reduction may include, for example, reduction with an alkali metal borohydride (e.g., sodium borohydride, etc.) and the like.

The reaction temperature is not critical and may be suitably selected in accordance with the kind of the protective group to be eliminated and the method to be applied, and the present reaction is preferably carried out under a mild condition such as under cooling, at ambient temperature or slightly elevated temperature.

Process 3

The object compound (Id) or a salt thereof can be prepared by subjecting the compound (Ic) or a salt thereof to elimination reaction of the aminoprotective group in $R_a^4$.

The present reaction is carried out by conventional method, such as hydrolysis, reduction or the like. The method of hydrolysis and reduction and the reaction conditions (e.g. reaction temperature, solvent, etc.) are substantially the same as those illustrated for the elimination of the protective group of the protected amino group for $R_a^{1'}$ of the compound (Ia) in the above Process 2 and therefore are to be referred to said explanation.

Process 4

The object compound (If) can be prepared by subjecting the compound (Ie) to elimination reaction of a carboxy-protective group.

The present reaction is carried out by conventional method, such as hydrolysis, reduction or the like. The methods of hydrolysis and reduction and the reaction conditions (e.g., reaction temperature, solvent, etc.) are substantially the same as those illustrated for the elimination of the protective group of the protected amino group for $R_a^{1'}$ of the compound (Ia) in the Process 2 and therefore are to be referred to said explanation.

Process 5

The object compound (Ih) or a salt thereof can be prepared by reacting the compound (Ig) or a salt thereof with the compound (IV) or its reactive derivative at the mercapto group.

Suitable reactive derivative at the mercapto group of the compound (IV) may include a metal salt such as an alkali metal salt (e.g., sodium salt, potassium salt, etc.) an alkaline earth metal salt (e.g., magnesium salt, etc.) and the like.

The reaction may be preferably carried out in a solvent such as water, acetone, chloroform, nitrobenzene, N,N-dimethylformamide, methanol, ethanol, dimethylsulfoxide, or any other organic solvents, which do not adversely influence the reaction and an optional mixture thereof, preferably in a rather high polar solvents. The reaction is preferably carried out in around neutral condition. When the compound (Ig) or the compound (IV) is used in a free form, the reaction is preferably conducted in the presence of a base such as alkali metal hydroxide, alkali metal carbonate, alkali metal bicarbonate, trialkylamine or the like. The reaction is usually carried out at ambient temperature or slightly elevated temperature.

The present invention may include, within its scope, the cases that the protected amino group and/or the derivative at the carboxy group are transformed into the corresponding free amino group and/or carboxy group during the reaction or posttreatment in the processes as explained above.

The object compounds (I) obtained according to the processes 1–5 as explained above can be used without any isolation in the subsequent processes.

Processes A to Q for preparing the starting compounds are explained in detail as follows.

Process A

The compound (A-3) or a salt thereof can be prepared by reacting the compound (A-1) or a salt thereof with the compound (A-2).

The present reaction is usually carried out in the presence of a base as aforementioned in Process 2 in a conventional solvent which does not adversely influence the reaction.

The reaction temperature is not critical and the reaction can be carried out under cooling or at ambient temperature.

Process B

The compound (B-2) or a salt thereof can be prepared by reacting the compound (A-1) or a salt thereof with the compound (B-1) or a salt thereof.

The present reaction is substantially the same as Process A, and accordingly the reaction conditions (e.g. a base, reaction temperature, solvent, etc.) can be referred to those of Process A.

Process C

The compound (C-2) or a salt thereof can be prepared by reacting the compound (C-1) or a salt thereof with carbon dioxide.

The present reaction is usually carried out in the presence of a base such as alkyl lithium (e.g. butyl lithium, etc.) or the like in a conventional solvent which does not adversely in fluence the reaction.

The reaction temperature is not critical and the reaction can be carried out under cooling or at ambient temperature.

Process D

The compound (D-2) or a salt thereof can be prepared by reacting the compound (D-1) or a salt thereof with an halogenating agent.

Suitable halogenating agent may include a conventional one used for halogenation of hydroxy group such as phosphorus compound (e.g., phosphoryl chloride, phosphorus trichloride, phosphorus tribromide, phosphorus pentachloride, etc.) or the like.

The present reaction is usually carried out in a conventional solvent which does not adversely influence the reaction.

The reaction temperature is not critical and the reaction can be carried out under warming to heating.

Process E

The compound (E-2) can be prepared by subjecting a compound (E-1) to dehalogenative reduction. The dehalogenative reduction to be used in this process is a conventional one such as a catalytic reduction (e.g., palladium on carbon, palladium black, spongy palladium, etc.) and the like.

The present reaction is usually carried out in a conventional solvent which does not adversely influence the reaction.

The reaction temperature is not critical and the reaction can be carried out at ambient temperature.

Process F

The compound (F-2) or a salt thereof can be prepared by reacting the compound (F-1) or a salt thereof with a nucleophile selected from alkanol and arenethiol or a salt thereof.

The present reaction is usually carried out in the presence of a base as aforementioned in Process 2 in a conventional solvent which does not adversely influence the reaction.

The reaction temperature is not critical and the reaction can be carried out under cooling or at ambient temperature.

Process G

The compound (G-2) or a salt thereof can be prepared by reacting the compound (G-1) or a salt thereof with a carboxy protective agent.

Suitable agent to be used in this reaction may include conventional ones such as lower alkyl halide (e.g. methyliodide, etc.) di(lower)alkylsulfate (e.g. dimethylsulfate, etc.), diazo(lower)alkane (e.g. diazomethane, etc.), lower alkanol (e.g. methanol, ethanol, etc.) or the like.

The present reaction is usually carried out in the presence of an acid as aforementioned in Process 2 in a conventional solvent which does not adversely influence the reaction.

The reaction temperature is not critical and the reaction can be carried out under cooling to heating.

Process H

The compound (H-2) can be prepared by reacting the compound (H-1) with a compound of the formula: $R^{10}SCH_2SOR^{10}$.

The present reaction is usually carried out in the presence of a base as aforementioned Process 2 in a conventional solvent which does not adversely influence the reaction.

The reaction temperature is not critical and the reaction can be carried out under cooling to under heating.

Process I

The compound (I-1) can be prepared by reacting the compound (H-2) with an acid and/or acid anhydride such as acetic acid and/or acetic anhydride. The reaction can preferably be carried out in the presence of alkali metal perchlorate (e.g. sodium perchlorate, potassium perchlorate, etc.), alkaline earth metal perchlorate (e.g., magnesium perchlorate, calcium perchlorate, etc.) and the like, and an acid such as an organic carboxylic acid (e.g., formic acid, etc.).

The reaction temperature is not critical and the reaction is preferably carried out under warming to heating.

Process J

The compound (J-2) or a salt thereof can be prepared by subjecting the compound (J-1) to elimination reaction of the carboxy-protective group.

The present reaction can be carried out in substantially the same manner as that of Process 4. Accordingly, the detailed explanation therefor is to be referred to said Process 4.

Process K

The compound (K-2) or a salt thereof can be prepared by reacting the compound (K-1) or a salt thereof with an amino-protective agent. When the amino-protective agent is acylating agent, the reaction can be carried out in substantially the same manner as that of Process 1. Accordingly, the detailed explanation therefor is to be referred to said Process 1.

Process L

The compound (L-2) can be prepared by oxidizing the compound (L-1).

The present oxidation reaction is conducted by a conventional method which is applied for the transformation of so-called activated methylene group into carbonyl group. That is, the present oxidation is conducted by a conventional method such as oxidation by using selenium dioxide or the like.

The present reaction is usually carried out in a conventional solvent which does not adversely influence the reaction.

The reaction temperature is not critical and the reaction is preferably carried out under warming to heating.

Process M

The compound (M-2) or a salt thereof can be prepared by reacting the compound (M-1) or its hydrate or a salt thereof with a compound of the formula: $R^6$—$ONH_2$ or a salt thereof.

The present reaction is usuallly carried out in a conventional solvent which does not adversely influence the reaction, and when a salt of the compound of the formula: $R^6$—$ONH_2$ is used in the reaction, the reaction is preferably carried out in a presence of a base as aforementioned in Process 2.

The reaction temperature is not critical and the reaction can be carried out at ambient temperature.

Process N

The compound (N-2) or a salt thereof can be prepared by subjecting the compound (N-1) or a salt thereof to elimination reaction of the amino-protective group.

The present reaction can be carried out in substantially the same manner as that of Process 2. Accordingly, the detailed explanation therefor is to be referred to said Process 2.

Process O

The compound (O-2) or a salt thereof can be prepared by reacting the compound (O-1) or a salt thereof with a nitrosating agent.

Suitable nitrosating agent may include a conventional one such as alkali metal nitrite (e.g., sodium nitrite, potassium nitrite, etc.) and the like.

The present reaction is usually carried out in a conventional solvent which does not adversely influence the reaction.

The reaction temperature is not critical and the reaction is preferably carried out under cooling or at ambient temperature.

Process P

The compound (P-2) or a salt thereof can be prepared by reacting the compound (P-1) or a salt thereof with a substituting agent capable for substituting a hydrogen atom of the hydroxy in the compound (P-1) by $R^{6'}$ group.

The present reaction is usually carried out in a conventional solvent which does not adversely influence the reaction.

When the substituting agent is diazo compound, the reaction can be carried out under cooling or at ambient temperature.

Process Q

The compound (Q-2) or a salt there of can be prepared by reacting the compound (Q-1) or a salt thereof with a halogenating agent.

Suitable halogenating agent may include a conventional one used for halogenation of an aromatic ring such as chlorine, bromine and the like.

The present reaction is usually carried out in a conventional solvent which does not adversely influence the reaction.

The reaction temperature is not critical and the reaction can be carried out at ambient temperature.

It is to be noted that, in the aforementioned reactions and/or the post-treatment of the reaction mixture, the aforementioned geometric isomer may be occasionally transformed into the other geometric isomer and such case is also included in the scope of the present invention.

In case that the object compound (I) have a free carboxy group at 4 position and/or a free amino group for $R_a^1$, it may be transformed into its pharmaceutically acceptable salt by a conventional method.

All of the object compounds (I) and nontoxic pharmaceutically acceptable salt thereof of the present invention are novel and exhibit high antibacterial activity, inhibiting the growth of a wide variety of pathogenic microorganisms including Gram-positive and Gram-negative bacteria and are useful as antibacterial agents. Now, in order to show the utility of the object compounds (I), the test data on the in vitro antibacterial activity of some representative compounds (I) of this invention are shown in the following.

In vitro antibacterial activity

Test Method

In vitro antibacterial activity was determined by the two-fold agar-plate dilution method as described below.

One loopful of an overnight culture of each test strain in Trypticase-soy broth (approximately $10^6$ variable cells per ml.) was streaked on heart infusion agar (HI-agar) containing graded concentrations of antibiotics, and the minimal inhibitory concentration (MIC) was expressed in terminal of μg/ml after incubation at 37° C. for 20 hours.

Test compounds

No. 1: 7-[2-(4-Aminopyrimidin-2-yl)-2-ethoxyiminoacetamido]-3-(1,3,4-thiadiazol-2-ylthiomethyl)-3-cephem-4-carboxylic acid (syn isomer).

No. 2: 7-[2-(4-Aminopyrimidin-2-yl)-2-methoxyiminoacetamido]-3-[(1-allyl-1H-tetrazol-5-yl)thiomethyl]-3-cephem-4-carboxylic acid (syn isomer).

No. 3: 7-[2-Allyloxyimino-2-(4-aminopyrimidin-2-yl)acetamido]-3-(1,3,4-thiadiazol-2-ylthiomethyl)-3-cephem-4-carboxylic acid (syn isomer).

No. 4: 7-[2-(4-Aminopyrimidin-2-yl)-2-propoxyiminoacetamido]-3-(1,3,4-thiadiazol-2-ylthiomethyl)-3-cephem-4-carboxylic acid (syn isomer).

No. 5: 7-[2-(6-Aminopyridin-2-yl)-2-(2,2,2-trifluoroethoxyimino)acetamido]-3-[(1-carboxymethyl-1H-tetrazol-5-yl)thiomethyl]-3-cephem-4-carboxylic acid (syn isomer).

No. 6: 7-[2-(6-aminopyridin-2-yl)-2-methoxyiminoacetamido]-3-(1-methyl-1H-tetrazol-5-yl)thiomethyl-3-cephem-4-carboxylic acid (syn isomer).

No. 7: 7-[2-(6-aminopyridin-2-yl)-2-methoxyiminoacetamido]-3-cephem-4-carboxylic acid.

No. 8: 7-[2-(6-aminopyridin-2-yl)-2-methoxyiminoacetamido]-3-carbamoyloxymethyl-3-cephem-4-carboxylic acid (syn isomer).

No. 9: 7-[2-(6-aminopyridin-2-yl)-2-methoxyiminoacetamido]cephalosporanic acid (syn isomer).

No. 10: 7-[2-(2-aminopyrimidin-4-yl)-2-methoxyiminoacetamido]-3-(1-methyl-1H-tetrazol-5-yl)thiomethyl-3-cephem-4-carboxylic acid.

No. 11: 7-[2-(4-aminopyrimidin-2-yl)-2-methoxyiminoacetamido]-3-(1-methyl-1H-tetrazol-5-ylthiomethyl)-3-cephem-4-carboxylic acid (syn isomer).

No. 12: 7-[2-allyloxyimino-2-(6-aminopyridin-2-yl)acetamido]-3-(1-methyl-1H-tetrazol-5-ylthiomethyl)-3-cephem-4-carboxylic acid (syn isomer).

No. 13: 7-[2-(6-aminopyridin-2-yl)-2-propargyloxyiminoacetamido]-3-(1-methyl-1H-tetrazol-5-ylthiomethyl)-3-cephem-4-carboxylic acid (syn isomer).

No. 14: 7-[2-(6-aminopyridin-2-yl)-2-ethoxyiminoacetamido]-2-methyl-3-cephem-4-carboxylic acid (syn isomer).

| | Test Results MIC (µg/ml.) | |
|---|---|---|
| | Micro-organisms | |
| Compound No. | Proteus vulgaris IAM 1025 | Pseudomonas aeruginosa NCTC-10490 |
| 1 | <0.025 | <1.56 |
| 2 | <0.025 | 6.25 |
| 3 | 0.05 | <1.56 |
| 4 | <0.025 | <1.56 |
| 5 | 0.025 | <1.56 |
| 6 | ≦0.025 | ≦1.56 |
| 7 | ≦0.025 | 6.25 |
| 8 | 0.05 | 3.13 |
| 9 | ≦0.025 | ≦1.56 |
| 10 | 0.2 | 6.25 |
| 11 | ≦0.025 | <1.56 |
| 12 | 0.05 | ≦1.56 |
| 13 | 0.05 | ≦1.56 |
| 14 | 0.05 | <1.56 |

For therapeutic administration, the object compounds (I) and pharmaceutically acceptable salt thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age, conditions of the patient, a kind of disease, a kind of the compounds (I) to be applied, etc. In general, amounts between 1 mg. and about 2000 mg. or even more per day may be administered to a patient. An average single dose of about 50 mg., 100 mg., 250 mg., and 500 mg. of the object compounds (I) of the present invention may be used in treating diseases infected by pathogenic bacteria.

The following examples are given for the purpose of illustrating the present invention:

EXAMPLE 1

(1) Phosphoryl chloride (0.998 g.) was added to N,N-dimethylformamide (5 ml.) and stirred at 40° C. for 30 minutes. To the solution was added a solution of 2-(6-formamidopyridin-2-yl)-2-methoxyiminoacetic acid (syn isomer) (1.125 g.) in N,N-dimethylformamide (5 ml.) at −15° C., and stirred at −10° to −8° C. for 50 minutes [solution A]. On the other hand, 7-amino-3-(1-methyl-1H-tetrazol-5-yl)thiomethyl-3-cephem-4-carboxylic acid (2.007 g.) and trimethylsilylacetamide (7.22 g.) were dissolved in methylene chloride (20 ml.) at 40° C. and cooled. To the cool solution was added the above solution A at −20° to −15° C. and stirred at the same temperature for 40 minutes. The resultant solution was poured into a solution of a saturated aqueous solution of sodium bicarbonate (30 ml.) and water (40 ml.) under ice cooling. The aqueous layer was separated, washed with ethyl acetate, and then ethyl acetate (50 ml.) was added to the aqueous layer. The solution was adjusted to pH 3 with 10% hydrochloric acid, and extracted with ethyl acetate twice. The extract was washed with water and concentrated to a small amount under reduced pressure. The appeared precipitates were collected by filtration, washed with ethyl acetate and dried to give 7-[2-(6-formamidopyridin-2-yl)-2-methoxyiminoacetamido]-3-(1-methyl-1H-tetrazol-5-yl)thiomethyl-3-cephem-4-carboxylic acid (syn isomer) (873 mg.). The same product (126 mg.) was recovered from the mother liquor. Total yield was 999 mg.

I.R. $\nu_{max}^{Nujol}$: 3280, 1785, 1728, 1673, 1454, 1053 cm$^{-1}$.

N.M.R. δppm (DMSO-d$_6$): 3.62, 3.76 (2H, AB-q, J=18 Hz), 3.90 (3H, s), 3.94 (3H, s), 4.24, 4.35 (2H, AB-q, J=16 Hz), 5.16 (1H, d, J=5 Hz), 5.85 (1H, dd, J=5 Hz, 8 Hz), 7.50 (1H, d, J=8 Hz), 7.80 (1H, t, J=8 Hz), 8.00 (0.3H, broad s), 6.88 (0.7H, broad d, J=8 Hz), 9.28 (0.7H, broad d, J=10 Hz), 8.28 (0.3H, broad s), 9.50 (1H, broad d, J=8 Hz), 10.7 (1H, m, J=10 Hz).

(2) A mixture of N,N-dimethylformamide (3 ml.) and phosphoryl chloride (460 mg.) was stirred at 37° to 40° C. for 30 minutes. To the solution were added methylene chloride (3 ml.) and 2-(6-formamidopyridin-2-yl)-2-methoxyiminoacetic acid (669 mg.) at −20° to −25° C. and stirred at −10° to −15° C. for one hour. A solution of 4-nitrobenzyl 7-amino-3-cephem-4-carboxylate (670 mg.) and trimethylsilylacetamide (2 g.) in methylene chloride (200 ml.) was added to the above solution at −10° to −15° C., and then stirred at the same temperature for 30 minutes. After the solution was concentrated under reduced pressure, ethyl acetate and water were added to the residue. The ethyl acetate layer was separated, washed with an aqueous solution of sodium bicarbonate, water and a saturated aqueous solution of sodium chloride, dried over magnesium sulfate and then concentrated under reduced pressure. The residue was triturated with diethyl ether to give 4-nitrobenzyl 7-[2-(6-formamidopyridin-2-yl)-2-methoxyiminoacetamido]-3-cephem-4-carboxylate (730 mg.), mp. 195° to 200° C. (dec.).

I.R. $\nu_{max}^{Nujol}$: 3350, 3200, 1790, 1725, 1690, 1660 cm$^{-1}$.

The following compounds were prepared in substantially the same manner as those of Example 1-(1) and (2).

(3) 7-[2-(6-Formamidopyridin-2-yl)-2-methoxyiminoacetamido]-3-(1,3,4-thiadiazol-2-yl)thiomethyl-3-cephem-4-carboxylic acid (syn isomer), mp. 167° to 169° C. (dec.).

I.R. $\nu_{max}^{Nujol}$: 3270, 1780, 1670, 1455, 1370, 1252, 1052 cm$^{-1}$.

N.M.R. δppm (DMSO-d$_6$): 3.65, 3.78 (2H, AB-q, J=18 Hz), 3.97 (3H, s), 4.30, 4.57 (2H, AB-q, J=12 Hz), 5.22 (1H, d, J=5 Hz), 5.93 (1H, dd, J=5 Hz, 8 Hz), 6.57 (1H, broad d, J=7 Hz), 7.58 (1H, d, J=7 Hz), 7.90 (1H, t, J=7 Hz), 9.3-9.8 (2H, m), 9.63 (1H, s), 10.62, 10.70 (1H, m).

(4) 7-[2-(6-Formamidopyridin-2-yl)-2-methoxyiminoacetamido]-3-(5-t-butoxycarbonylaminomethyl-1,3,4-thiadiazol-2-yl)thiomethyl-3-cephem-4-carboxylic acid (syn isomer), mp. 178° to 186° C. (dec.).

I.R. $\nu_{max}^{Nujol}$: 3280, 1785, 1720-1660 (broad), 1457, 1255, 1162, 1052 cm$^{-1}$.

N.M.R. δppm (DMSO-d$_6$): 1.40 (9H, s), 3.63, 3.78 (2H, AB-q, J=18 Hz), 3.98 (3H, s), 4.1-4.7 (4H, m), 5.21 (1H, d, J=4.5 Hz); 5.89 (1H, dd, J=4.5 Hz, 8 Hz), 6.2-8.2 (4H, m), 8.33 (0.3 H, broad s), 9.35 (0.7H, broad d, J=10 Hz), 9.55 (1H, broad d, J=8 Hz), 10.5-10.8 (1H, m).

(5) 7-[2-(6-Formamidopyridin-2-yl)-2-methoxyiminoacetamido]cephalosporanic acid (syn isomer), mp 191° to 193° C. (dec.).

I.R. $\nu_{max}^{Nujol}$: 3250, 1780, 1725, 1665, 1240, 1053 cm$^{-1}$.

N.M.R. δppm (DMSO-d$_6$): 2.03 (3H, s), 3.53, 3.62 (2H, AB-q, J=17 Hz), 3.97 (3H, s), 4.70, 5.02 (2H, AB-q, J=13 Hz), 5.18 (1H, d, J=5 Hz), 5.88 (1H, dd, J=5 Hz, 8 Hz), 6.90 (1H, broad d, J=7 Hz), 7.53 (1H, d, J=7 Hz), 7.82 (1H, t, J=7 Hz), 9.3 (1H, broad d, J=9 Hz), 9.54 (1H, d, J=8 Hz), 10.6 (1H, m).

(6) 4-Nitrobenzyl 7-[2-(6-formamidopyridin-2-yl)2-methoxyiminoacetamido]-3-chloro-3-cephem-4-carboxylate (syn isomer), mp. 162° to 168° C. (dec.).

I.R. $\nu_{max}^{Nujol}$: 3200, 1780, 1735, 1690-1660, 1040 cm$^{-1}$.

N.M.R. δppm (DMSO-d$_6$): 3.70, 4.10 (2H, AB-q, J=18 Hz), 3.93 (3H, s), 5.32 (1H, d, J=5 Hz), 5.45 (2H, s), 5.98 (1H, dd, J=5 Hz), 6.9 (1H, m), 7.50 (1H, d, J=8 Hz), 7.57 (2H, d, J=8 Hz), 7.83 (1H, m), 8.26 (2H, d, J=8 Hz), 9.30 (1H, m), 9.69 (1H, d, J=8 Hz), 10.70 (1H, m).

(7) 4-Nitrobenzyl 7-[2-(6-formamidopyridin-2-yl)-2-methoxyiminoacetaido]-3-methoxy-3-cephem-4-carboxylate.

I.R. $\nu_{max}^{Nujol}$: 3700-3000, 1780, 1710-1640, 1050, 1010, 640 cm$^{-1}$.

N.M.R. δppm (DMSO-d$_6$): 3.7 (2H, broad s), 3.84 (3H, s), 3.99 (3H, s), 5.25 (1H, d, J=5 Hz), 5.36 (2H, s), 5.77 (1H, dd, J=5 Hz, 8 Hz), 6.9 (1H, m), 7.52 (1H, d, J=8 Hz), 7.67 (2H, d, J=8 Hz), 7.8 (1H, m), 8.22 (2H, d, J=8 Hz), 9.3 (1H, m), 9.52 (1H, d, J=8 Hz), 10.7 (1H, m).

(8) Benzhydryl 7-[2-(6-formamidopyridin-2-yl)-2-methoxyiminoacetamido]-7-methoxy-3-(1-methyl-1H-tetrazol-5-yl)thiomethyl-3-cephem-4-carboxylate (syn isomer), mp. 145° to 150° C. (dec.).

I.R. $\nu_{max}^{Nujol}$: 3230, 1780, 1725, 1680 cm$^{-1}$.

N.M.R. δppm (acetone-d$_6$): 3.59 (3H, s), 3.63, 3.73 (2H, AB-q, J=18 Hz), 3.83 (3H, s), 3.96 (3H, s), 4.23, 4.43 (2H, AB-q, J=13 Hz), 5.10 (1H, s), 6.86 (1H, s), 7.16-7.80 (13H, m).

(9) 7-[2-(6-Formamidopyridin-2-yl)-2-methoxyiminoacetamido]-2-methyl-3-cephem-4-carboxylic acid (syn isomer), mp. 198° to 202° C. (dec.).

I.R. $\nu_{max}^{Nujol}$: 3380-3070, 1790, 1735, 1670 cm$^{-1}$.

N.M.R. δppm (DMSO-d$_6$): 1.47 (3H, d, J=7 Hz), 3.5-4.2 (1H, m), 4.00 (3H, s), 5.20 (1H, d, J=5 Hz), 6.05 (1H, dd, J=5 Hz, 8 Hz),, 6.67 (1H, d, J=6 Hz), 6.9-8.7 (3H, m).

(10) 7-[2-(6-Formamidopyridin-2-yl)-2-methoxyiminoacetamido]-3-methyl-3-cephem-4-carboxylic acid (syn isomer), mp. 225° to 225.5° C. (dec.).

I.R. $\nu_{max}^{Nujol}$: 3400, 3250, 3220, 1773, 1730, 1680-1650, 1560, 1260, 1160, 1050 cm$^{-1}$.

N.M.R. δppm (DMSO-d$_6$): 2.02 (3H, s), 3.3, 3.6 (2H, AB-q, J=18 Hz), 3.96 (3H, s), 5.13 (1H, d, J=4.5 Hz), 5.78 (1H, dd, J=4.5 Hz, 8 Hz), 6.9-8.3 (3H, m), 9.3-9.5 (2H, m), 10.55 (1H, m).

(11) 7-[2-(6-Trifluoroacetamidopyridin-2-yl)-2-methoxyiminoacetamido]cephalosporanic acid (syn isomer), mp. 151° to 155° C.

I.R. $\nu_{max}^{Nujol}$: ~3260, 1775, 1730, 1690-1670, 1380, 1160, 1040 cm$^{-1}$.

N.M.R. δppm (DMSO-d$_6$): 2.00 (3H, s), 3.5 (2H, broad s), 3.98 (3H, s), 4.67, 5.03 (2H, AB-q, J=12 Hz), 5.18 (1H, d, J=5 Hz), 5.88 (1H, dd, J=5 Hz), 8 Hz), 7.5-8.0 (3H, m), 9.51 (1H, d, J=8 Hz), 11.63 (1H, m).

(12) 7-[2-(6-Formamidopyridin-2-yl)-2-methoxyiminoacetamido]-3-carbamoyloxymethyl-3-cephem-4-carboxylic acid (syn isomer), mp. 185° to 190° C. (dec.).

I.R. $\nu_{max}^{Nujol}$: 3200, 1790, 1700, 1665 cm$^{-1}$.

N.M.R. δppm (DMSO-d$_6$): 3.60, 3.42 (2H, AB-q,, J=18 Hz), 3.98 (3H, s), 4.64, 4.92 (2H, AB-q, J=12 Hz), 5.20 (1H, d, J=4 Hz), 5.90 (1H, dd, J=4 Hz), 9 Hz), 6.50 (2H, s), 6.8-8.0 (3H, s), 9.58 (1H, d, J=9 Hz).

(13) 7-[2-(2-Formamidopyrimidin-4-yl)-2-methoxyiminoacetamido]-3-(1-methyl-1H-tetrazol-5-yl)thiomethyl-3-cephem-4-carboxylic acid, mp. 138° to 155° C. (dec.).

I.R. $\nu_{max}^{Nujol}$: 3300, 1787, 1565, 1408, 1043 cm$^{-1}$.

N.M.R. δppm (DMSO-d$_6$): 3.63, 3.76 (2H, AB-q, J=18 Hz), 3.92 (3H, s), 4.02 (3H, s), 4.24, 4.35 (2H, Ab-q, J=12 Hz), 5.16 (1H, d, J=5 Hz), 5.86 (1H, dd, J=5 Hz, 9 Hz), 7.47 (1H, d, J=6 Hz), 8.63 (1H, d, J=8 Hz), 9.37 (1H, d, J=10 Hz), 9.60 (1H, d, J=9 Hz), 11.00 (1H, d, J=10 Hz).

(14) 7-[2-(6-Formamidopyridin-2-yl)-2-ethoxyiminoacetamido]-3-(1-methyl-1H-tetrazol-5-yl)thiomethyl-3-cephem-4-carboxylic acid (syn isomer), mp. 150° to 155° C. (dec.).

I.R. $\nu_{max}^{Nujol}$: 3200, 1780, 1700, 1660 cm$^{-1}$.

N.M.R. δppm (DMSO-d$_6$): 1.30 (3H, t, J=7 Hz), 3.65, 3.80 (2H, AB-q, J=16 Hz), 3.95 (3H, s), 4.25 (2H, q, J=7 Hz), 4.28 (2H, broad s), 5.18 (1H, d, J=5 Hz), 5.90 (1H, dd, J=5 Hz, 9 Hz), 6.8-8.2 (3H, m), 9.4 (2H, m), 10.6 (1H, broad d).

(15) A solution of pivaloyl chloride (1.07 g.) in methylene chloride (3 ml.) was added to a solution of 2-(6-Formamidopyridin-2-yl)acetic acid (1.6 g.) and 1,5-diazabicyclo[5,4,0]undecene-5(1.35 g.) in methylene chloride (25 ml.) at −20° to −25° C., and stirred at the same temperature for one hour [solution A]. On the other hand, a solution of 7-amino-3-(1-methyl-1H-tetrazol-5-yl)thiomethyl-3-cephem-4-carboxylic acid (3.24 g.) and 1,5-diazabicyclo[5,4,0]undecene-5 (1.35 g.) in methylene chloride (60 ml.) was stirred at room temperature for 10 minutes. To the solution was added the above solution A at −20° to −25° C. and stirred at the same temperature for 1.5 hours. After removing the solvent from the resultant solution, ethyl acetate, water and sodium bicarbonate were added to the residue. The aqueous layer was separated and washed with ethyl acetate. Ethyl acetate (300 ml.) was added to the aqueous solution, adjusted to pH 2 to 3 with 5% hydrochloric acid, and then shaken sufficiently. The ethyl acetate layer was separated, washed with water and concentrated under reduced pressure to give 7-[2-(6-formamidopyridin-2-yl)acetamido]-3-(1-methyl-1H-tetrazol-5-yl)thiomethyl-3-cephem-4-carboxylic acid (2.2 g.).

I.R. $\nu_{max}^{Nujol}$: 3320, 1782, 1690 (broad) cm$^{-1}$.

N.M.R. δppm (DMSO-d$_6$): 3.68 (4H, broad s), 3.93 (3H, s), 4.33 (2H, broad s), 5.10 (1H, d, J=5 Hz), 5.72 (1H, dd, J=5 Hz, 9 Hz), 6.8, 7.8 (1H), 7.10 (1H, d, J=8 Hz), 7.73 (1H, t, J=8 Hz), 9.10 (1H, d, J=9 Hz), 8.33, 9.37 (1H, broad s), 10.55 (1H, broad d, J=7 Hz).

(16) A solution of phosphoryl chloride (2.14 g.) in N,N-dimethylformamide (14 ml.) was stirred at 37° to 40° C. for 30 minutes. To the solution were added methylene chloride (14 ml.) and 2-(6-formamidopyridin-2-yl)-2-dichloroacetoxyiminoacetic acid (syn isomer) (4.48 g.) at −20° to −25° C. and stirred at −10° to −15° C. for 30 minutes [solution A]. On the other hand, 7-amino-3-(1-methyl-1H-tetrazol-5-yl)thiomethyl-3-cephem-4-carboxylic acid (4.6 g.) was dissolved in a solution of trimethylsilylacetamide (14 g.) in methylene chloride (150 ml.) at 40° C., and cooled to −10° to −15° C. The solution was added to the above solution A at −10° to −15° C. and stirred at the same temperature for 30 minutes. After removing methylene chloride from the resultant solution under reduced pressure, ice water and ethyl acetate were added to the residue, and adjusted to pH 4 with an aqueous solution of sodium bicarbonate. The aqueous layer was separated, washed with ethyl acetate, adjusted to pH 2 with 10% hydrochloric acid, and then extracted with ethyl acetate. The extract was washed with a saturated aqueous solution of sodium chloride, dried over magnesium sulfate and concentrated under reduced pressure. The residue was triturated with diethyl ether. The precipitates were collected by filtration; washed with diethyl ether and dired to give 7-[2-(6-formamidopyridin-2-yl)-2-hydroxyiminoacetamido]-3-(1-methyl-1H-tetrazol-5-yl)thiomethyl-3-cephem-4-carboxylic acid (syn isomer) (5.0 g.), mp. 110° to 115° C.

I.R. $\nu_{max}^{Nujol}$: 3240, 1780, 1700, 1660 cm$^{-1}$.

N.M.R. δppm (DMSO-d$_6$): 3.73 (2H, broad s), 4.00 (3H, s), 4.35 (2H, broad s), 5.20 (1H, d, J=4 Hz), 5.93 (1H, dd, J=9 Hz, 4 Hz), 6.83-8.0 (3H, m), 9.45 (1H, d, J=9 Hz).

EXAMPLE 2

(1) Conc. hydrochloric acid (127.4 mg.) was dropwise added to a suspension of 7-[2-(6-formamidopyridin-2-yl)-2-methoxyiminoacetamido]-3-(1-methyl-1H-tetrazol-5-yl)thiomethyl-3-cephem-4-carboxylic acid (syn isomer, 930 mg.) in methanol (15 ml.) and stirred at room temperature for 40 minutes. After methanol was removed under reduced pressure from the resultant solution, water (100 ml.) was added to the residue and the solid substance was dissolved by adding 10% hydrochloric acid. After the insoluble material was filtered out, the filtrate was adjusted to pH 3 with an aqueous sodium bicarbonate. The solution was purified by column chromatography on macroporous, non-ionic adsorption resin "Diaion HP-20" (Trademark, manufactured by Mitsubishi Chemical Industries Ltd.), with an eluent of aqueous methanol. The eluate was lyophilized to give 7-[2-(6-aminopyridin-2-yl)-2-methoxyiminoacetamido]-3-(1-methyl-1H-tetrazol-5-yl)thiomethyl-3-cephem-4-carboxylic acid (syn isomer) (605 mg.), mp. 150° to 154° C.

I.R. $\nu_{max}^{Nujol}$: 3360, 3220, 1780, 1670, 1620, 1585, 1544, 1042 cm$^{-1}$.

N.M.R. δppm (DMSO-d$_6$): 3.73 (2H, broad s), 3.75 (3H, s), 3.78 (3H, s), 4.30 and 4.37 (2H, AB-q, J=12 Hz), 5.17 (1H, d, J=5 Hz), 5.85 (1H, dd, J=5 Hz, 9 Hz), 6.53 (1H, d, J=8 Hz), 6.93 (1H, d, J=8 Hz), 7.48 (1H, t, J=8 Hz), 9.52 (1H, d, J=9 Hz).

(2) A solution of 7-[2-(6-formamidopyridin-2-yl)-2-methoxyiminoacetamido]-3-cephem-4-carboxylic acid (2.3 g.) in methanolic hydrochloric acid (12 ml., containing hydrochloric acid 6 mmol) was stirred at room temperature for one hour. To the resultant solution was added diethyl ether, and the precipitates were collected by filtration and dissolved in a mixture of methanol (50 ml.) and water (10 ml.). The solution was adjusted to pH 3 with an aqueous solution of sodium bicarbonate, treated with activated charcoal (1 g.) and concentrated to a volume of about 20 ml. The precipitating crystals were collected by filtration, washed with water and dried to give 7-[2-(6-aminopyridin-2-yl)-2-methoxyiminoacetamido]-3-cephem-4-carboxylic acid (1.12 g.), mp. 215° to 220° C. (dec.). The mother liquor and washings were combined and concentrated under reduced pressure. The appeared precipitates were collected by filtration, washed with water and dried to give the same object compound (0.36 g.). Total yield 1.48 g.

I.R. $\nu_{max}^{Nujol}$: 3300, 1785, 1730, 1670 cm$^{-1}$.

N.M.R. δppm (DMSO-d$_6$): 3.64 (2H, broad s), 4.06 (3H, s), 5.18 (1H, dd, J=4 Hz, 8 Hz), 5.85 (1H, dd, J=4 Hz, 8 Hz), 6.52 (1H, broad t), 6.78 (1H, d, J=8 Hz), 7.19 (1H, d, J=9 Hz), 7.92 (1H, dd, J=8 Hz, 9 Hz), 10.0 (1H, d, J=8 Hz).

The following compounds were prepared in substantially the same manner as those of Examples 2-(1) and (2).

(3) 7-[2-(6-Aminopyridin-2-yl)-2-methoxyiminoacetamido]-3-(1,3,4-thiadiazol-2-yl)thiomethyl-3-cephem-4-carboxylic acid (syn isomer), mp. 152° to 156° C. (dec.).

I.R. $\nu_{max}^{Nujol}$: 3400, 3230, 1780, 1670, 1622, 1590, 1550, 1050 cm$^{-1}$.

N.M.R. δppm (DMSO-d$_6$): 3.67, 3.73 (2H, AB-q, J=18 Hz), 3.83 (3H, s), 4.30, 4.55 (2H, AB-q, J=14 Hz), 5.13 (1H, d, J=4 Hz), 5.82 (1H, dd, J=4 Hz, 8 Hz), 6.50 (1H, d, J=8 Hz), 6.88 (1H, d, J=8 Hz), 7.45 (1H, t, J=8 Hz), 9.50 (1H, d, J=8 Hz), 9.57 (1H, s).

(4) 7-[2-(6-Aminopyridin-2-yl)-2-methoxyiminoacetamido]-3-(1-carboxymethyl-1H-tetrazol-5-yl)thiomethyl-3-cephem-4-carboxylic acid (syn isomer), mp. 169° to 177° C. (dec.).

I.R. $\nu_{max}^{Nujol}$: 3380, 3220, 1780, 1670, 1620, 1050 cm$^{-1}$.

N.M.R. δppm (DMSO-d$_6$+D$_2$O): 3.67, 3.80 (2H, AB-q, J=14 Hz), 3.98 (3H, s), 4.27, 4.50 (2H, AB-q, J=14 Hz), 5.18 (1H, d, J=5 Hz), 5.33 (2H, s), 5.88 (1H, d, J=5 Hz), 6.65 (1H, d, J=8 Hz), 6.97 (1H, d, J=8 Hz), 7.60 (1H, t, J=8 Hz).

(5) 7-[2-(6-Aminopyridin-2-yl)acetamido]-3-(1-methyl-1H-tetrazol-5-yl)thiomethyl-3-cephem-4-carboxylic acid (syn isomer), mp. 188° to 193° C. (dec.).

I.R. $\nu_{max}^{Nujol}$: 3600-3080, 1763, 1698, 1663 cm$^{-1}$.

N.M.R. δppm (D$_2$O+DCl): 3.83 (2H, s), 4.03 (2H, s), 4.15 (3H, s), 4.20, 4.43 (2H, AB-q, J=14 Hz), 5.27 (1H, d, J=5 Hz), 5.73 (1H, d, J=5 Hz), 6.93 (1H, d, J=8 Hz), 7.07 (1H, d, J=9 Hz), 7.98 (1H, dd, J=8 Hz, 9 Hz).

(6) 7-[2-(6-Aminopyridin-2-yl)-2-methoxyiminoacetamido]-3-chloro-3cephem-4-carboxylic acid hydrochloride (syn isomer), yellow powder, mp. 170° to 220° C. (dec.).

I.R. $\nu_{max}^{Nujol}$: 3300-3100, 1780, 1710, 1660, 1610, 1540, 1370 cm$^{-1}$.

N.M.R. δppm (DMSO-d$_6$): 3.57 4.13 (2H, AB-q, J=18 Hz), 4.13 (3H, s), 5.37 (1H, d, J=4.5 Hz), 5.88

(1H, dd, J=4.5 Hz, 8 Hz), 6.77 (1H, d, J=8 Hz), 7.21 (1H, d, J=9 Hz), 7.97 (1H, dd, J=8 Hz, 9 Hz), 8.0–9.3 (2H, m), 10.07 (1H, d, J=8 Hz).

(7) 7-[2-(6-Aminopyridin-2-yl)-2-methoxyiminoacetamido]-3-methoxy-3-cephem-4-carboxylic acid, mp. 175° to 182° C. (dec.).

I.R. $\nu_{max}^{Nujol}$: 3300, 1775, 1700-1650, 1045 cm$^{-1}$.

N.M.R. δ ppm (DMSO-d$_6$): 3.62 (2H, broad s), 3.75 (3H, s), 3.96 (3H, s), 5.15 (1H, d, J=4.5 Hz), 5.60 (1H, dd, J=4.5 Hz, 8 Hz), 6.70 (1H, d, J=8 Hz), 6.85 (1H, d, J=8 Hz), 7.56 (1H, t, J=8 Hz), 9.53 (1H, d, J=8 Hz).

(8) 7-[2-(6-Aminopyridin-2-yl)-2-methoxyiminoacetamido]-7-methoxy-3-(1-methyl-1H-tetrazol-5-yl)thiomethyl-3-cephem-4-carboxylic acid (syn isomer), mp. 165° to 170° C. dec.).

I.R. $\nu_{max}^{Nujol}$: 3300, 1780, 1700, 1680 cm$^{-1}$.

N.M.R. δ ppm (D$_2$O+NaHCO$_3$): 3.72, 3.58 (2H, AB-q, J=17 Hz), 3.64 (3H, s), 3.98 (3H, s), 4.04 (3H, s), 4.24, 4.06 (2H, AB-q, J=13 Hz), 5.20 (1H, s), 6.74 (1H, d, J=8 Hz), 7.10 (1H, d, J=8 Hz), 7.56 (1H, t, J=8 Hz).

(9) 7-[2-(6-Aminopyridin-2-yl)-2-methoxyiminoacetamido]-2-methyl-3-cephem-4-carboxylic acid (syn isomer), mp. 199° to 205° C. (dec.).

I.R. $\nu_{max}^{Nujol}$: 3400-3100, 1780, 1730, 1665, 1550, 1295, 1258, 1050 cm$^{-1}$.

N.M.R. δ ppm (DMSO-d$_6$): 1.48 (3H, d, J=9 Hz), 3.7–4.2 (1H, m), 4.10 (3H, s), 5.20 (1H, d, J=5 Hz), 5.92 (1H, dd, J=9 Hz, 5 Hz), 6.62 (1H, d, J=6 Hz), 6.78 (1H, d, J=8 Hz), 7.27 (1H, d, J=9 Hz), 8.00 (1H, dd, J=8 Hz, 9 Hz), 10.00 (1H, d, J=9 Hz).

(10) 7-[2-(6-Aminopyridin-2-yl)-2-methoxyiminoacetamido]-3-methyl-3-cephem-4-carboxylic acid hdrochloride (syn isomer), mp. 195° to 198° C. (dec.).

I.R. $\nu_{max}^{Nujol}$: 3100, 1780, 1682, 1668, 1260, 1050 cm$^{-1}$.

N.M.R. δ ppm (DMSO-d$_6$): 2.07 (3H, s), 3.35, 3.70 (2H, AB-q, J=18 Hz), 4.11 (3H, s), 5.18 (1H, d, J=4.5 Hz), 5.77 (1H, dd, J=4.5 Hz, 8 Hz), 6.80 (1H, d, J=8 Hz), 7.20 (1H, d, J=9 Hz), 7.98 (1H, dd, J=8 Hz, 9 Hz), 9.95 (1H, d, J=8 Hz), 6–9.3 (2H, m).

(11) 7-[2-(6-Aminopyridin-2-yl)-2-hydroxyiminoacetamido]-3-(1-methyl-1H-tetrazol-5-yl)thiomethyl-3-cephem-4-carboxylic acid (syn isomer), mp. 165° to 170° C. (dec.).

I.R. $\nu_{max}^{Nujol}$: 3300, 1760, 1680 cm$^{-1}$.

N.M.R. δ ppm (DMSO-d$_6$): 3.68 (2H, broad s), 3.93 (3H, s), 4.30 (2H, broad s), 5.13 (1H, d, J=4 Hz), 5.83 (1H, dd, J=4 Hz, 9 Hz), 6.48 (1H, d, J=8 Hz), 6.93 (1H, d, J=8 Hz), 7.43 (1H, t, J=8 Hz), 9.37 (1H, d, J=9 Hz).

(12) 7-[2-(6-Aminopyridin-2-yl)-2-methoxyiminoacetamido]-3-carbamoyloxymethyl-3-cephem-4-carboxylic acid (syn isomer), mp. 190° to 195° C. (dec.).

I.R. $\nu_{max}^{Nujol}$: 3400, 1780, 1720, 1670 cm$^{-1}$.

N.M.R. δ ppm (DMSO-d$_6$): 3.60, 3.44 (2H, AB-q, J=17 Hz), 3.88 (3H, s), 4.62, 4.88 (2H, Ab-q, J=13 Hz), 5.13 (1H, d, J=4 Hz), 5.80 (1H, dd, J=4 Hz, 9 Hz), 6.48 (1H, d, J=8 Hz), 6.88 (1H, d, J=8 Hz), 7.42 (1H, t, J=8 Hz), 9.44 (1H, d, J=9 Hz).

(13) 7-[2-(2-Aminopyrimidin-4-yl)-2-methoxyiminoacetamido]-3-(1-methyl-1H-tetrazol-5-yl)thiomethyl-3-cephem-4-carboxylic acid, mp. 181° to 182.5° C. (dec.).

I.R. $\nu_{max}^{Nujol}$: 3440, 3320, 1790, 1693, 1660, 1630, 1525, 1043 cm$^{-1}$.

N.M.R. δ ppm (DMSO-d$_6$): 3.68 (2H, broad s), 3.90 (3H, s), 3.93 (3H, s), 4.25, 4.33 (2H, AB-q, J=14 Hz), 5.12 (1H, d, J=5 Hz), 5.82 (1H, dd, J=5 Hz, 8 Hz), 6.85 (1H, d, J=5 Hz), 8.27 (1H, d, J=5 Hz), 9.50 (1H, d, J=8 Hz).

(14) 7-[2-(6-Aminopyridin-2-yl)-2-ethoxyiminoacetamido]-3-(1-methyl-1H-tetrazol-5-yl)thiomethyl-3-cephem-4-carboxylic acid (syn isomer), mp. 165° to 170° C. (dec.).

I.R. $\nu_{max}^{Nujol}$: 3380, 3240, 1780, 1670 cm$^{-1}$.

N.M.R. δ ppm (DMSO-d$_6$): 1.28 (3H, t, J=7 Hz), 3.64, 3.76 (2H, AB-q, J=18 Hz), 3.95 (3H, s), 4.18 (2H, q, J=7 Hz), 4.24, 4.38 (2H, AB-q, J=14 Hz), 5.15 (1H, d, J=5 Hz), 5.84 (1H, dd, J=5 Hz, 8 Hz), 6.50 (1H, d, J=8 Hz), 6.90 (1H, d, J=8 Hz), 7.43 (1H, t, J=8 Hz), 9.46 (1H, d, J=8 Hz).

(15) 7-[2-(6-Trifluoroacetamidopyridin-2-yl)-2-methoxyiminoacetamido]cephalosporanic acid (syn isomer) (380 mg.) was added to a solution of sodium acetate (857 mg.) in water (6 ml.), and stirred at room temperature for 16 hours. The resultant solution was washed with ethyl acetate (5 ml.), adjusted to pH 4 with 10% hydrochloric acid and washed with ethyl acetate. The solution was concentrated under reduced pressure to ⅔ of the initial volume, and subjected to column chromatography on macroporous, non-ionic adsorption resin "Diaion HP-20" (Trademark: manufactured by Mitsubishi Chemical Industries Ltd.) and eluted with 10% isopropyl alcohol. The eluate was lyophilized to give 7-[2-(6-aminopyridin-2-yl)-2-methoxyiminoacetamido]cephalosporanic acid (syn isomer) (130 mg.), pale yellow powder, mp. 155° to 161° C. (dec.).

I.R. $\nu_{max}^{Nujol}$: 3350-3220, 1780, 1740, 1680-1655, 1380, 1040 cm$^{-1}$.

N.M.R. δ ppm (DMSO-d$_6$): 2.00 (2H, s), 3.5 (2H, broad s), 3.88 (3H, s), 4.67, 5.04 (2H, AB-q, J=12 Hz), 5.15 (1H, d, J=5 Hz), 5.83 (1H, dd, J=5 Hz, 8 Hz), 6.45 (1H, d, J=8 Hz), 6.88 (1H, d, J=8 Hz), 7.43 (1H, t, J=8 Hz), 9.4 (1H, d, J=8 Hz).

EXAMPLE 3

A solution of 7-[2-(6-formamidopyridin-2-yl)-2-methoxyiminoacetamido]-3-(5-t-butoxycarbonylaminomethyl-1,3,4-thiadiazol-2-yl)thiomethyl-3-cephem-4-carboxylic acid (syn isomer)(1.12 g.) in 98% formic acid (11 ml.) was stirred at room temperature for 2 hours. Methanol (20 ml.) and conc. hydrochloric acid (0.3 ml.) were added to the resultant solution and then stirred at room temperature for 30 minutes. After the reaction mixture was concentrated in vacuo, water (25 ml.) was added to the residue, and then the solution was adjusted to pH 3 to 4 with a saturated aqueous solution of sodium bicarbonate. The solution was subjected to column chromatography on macroporous, non-ionic adsorption resin "Diaion HP-20" (Trademark, manufactured by Mitsubishi Chemical Industries Ltd.) with an eluent of aqueous methanol. The eluate was concentrated under reduced pressure and lyophilized to give 7-[2-(6-aminopyridin-2-yl)-2-methoxyiminoacetamido]-3-(5-aminomethyl-1,3,4-thiadiazol-2-yl)thiomethyl-3-cephem-4-carboxylic acid (syn isomer) (0.48 g.), mp. 248° to 251° C. (dec.).

I.R. $\nu_{max}^{Nujol}$: 3500, 3400, 3230, 1770, 1670, 1620, 1040 cm$^{-1}$.

N.M.R. δ ppm (DMSO-d$_6$): 3.53 (2H, broad s), 3.88 (3H, s), 4.35 (4H, broad s), 5.05 (1H, d, J=5 Hz), 5.75 (1H, dd, J=5 Hz, 8 Hz), 6.48 (1H, d, J=8 Hz), 6.88 (1H, d, J=8 Hz), 7.43 (1H, t, J=8 Hz).

EXAMPLE 4

(1) 10% Palladium on carbon (216 mg.) was added to a solution of 4-nitrobenzyl 7-[2-(6-formamidopyridin-2-yl)-2-methoxyiminoacetamido]-3-cephem-4-carboxylate (540 mg.) in tetrahydrofuran (10 ml.), methanol (5 ml.), acetic acid (0.075 ml.), and water (0.75 ml.). The mixture was subjected to catalytic reduction at ambient temperature under ordinary pressure for 5 hours, and then allowed to stand overnight. After filtered off the catalyst, the filtrate was concentrated under reduced pressure. Ethyl acetate and an aqueous solution of sodium bicarbonate were added to the residue, and the aqueous layer was separated. The solution was adjusted to pH 2 with 10% hydrochloric acid. The appeared precipitates were collected by filtration, washed with water and dried to give 7-[2-(6-formamidopyridin-2-yl)-2-methoxyiminoacetamido]-3-cephem-4-carboxylic acid (300 mg.), mp. 202° to 204° C. (dec.).

I.R. $\nu_{max}^{Nujol}$: 3250, 3200, 1780, 1720, 1660 cm$^{-1}$.

N.M.R. δ ppm (DMSO-d$_6$+D$_2$O): 3.56 (2H, broad d), 3.96 (3H, s), 5.13 (1H, d, J=5 Hz), 5.91 (1H, d, J=5 Hz), 6.46 (1H, m), 6.85–8.00 (3H, m).

(2) A mixture of 4-nitrobenzyl 7-[2-(6-formamidopyridin-2-yl)-2-methoxyiminoacetamido]-3-chloro-3-cephem-4-carboxylate (syn isomer)(1.43 g.), 10% palladium on carbon (0.8 g.), methanol (30 ml.) and tetrahydrofuran (60 ml.) was subjected to catalytic reduction at ambient temperature under ordinary pressure for 4 hours. After removing the catalyst by filtration, the filtrate was concentrated under reduced pressure. An aqueous solution of sodium bicarbonate and ethyl acetate were added to the residue, and the aqueous layer was separated. The aqueous layer was adjusted to pH 6, washed with ethyl acetate, and then adjusted to pH 1 to 2. The aqueous layer was extracted with ethyl acetate. The ethyl acetate extract was washed with an aqueous solution of sodium chloride, dried over magnesium sulfate, and concentrated under reduced pressure. Diethyl ether (30 ml.) was added to the residue, stirred for one hour, and then the precipitates were collected by filtration to give 7-[2-(6-formamidopyridin-2-yl)-2-methoxyiminoacetamido]-3-chloro-3-cephem-4-carboxylic acid (syn isomer)(680 mg.), brownish yellow powder, mp. 200° to 204° C. (dec.).

I.R. $\nu_{max}^{Nujol}$: 3225, 1780, 1730, 1680-1650, 1550 cm$^{-1}$.

N.M.R. δ ppm (DMSO-d$_6$): 3.65, 4.08 (2H, AB-q, J=18 Hz), 4.00 (3H, s), 5.30 (1H, d, J=4.5 Hz), 5.98 (1H, dd, J=8 Hz, 4.5 Hz), 6.97 (1H, d, J=8 Hz), 7.53 (1H, d, J=8 Hz), 7.87 (1H, t, J=8 Hz), 9.35 (1H, m), 9.63 (1H, d, J=8 Hz), 10.63 (1H, m).

The following compounds were prepared in substantially the same manner as that of Example 4-(1) and (2).

(3) 7-[2-(6-Formamidopyridin-2-yl)-2-methoxyiminoacetamido]-3-methoxy-3-cephem-4-carboxylic acid, mp. 173° to 175° C. (dec.).

I.R. $\nu_{max}^{Nujol}$: 3300, 1770, 1720-1660, 1040, 810, 620 cm$^{-1}$.

N.M.R. δ ppm (DMSO-d$_6$): 3.61 (2H, broad s), 3.73 (3H, s), 3.95 (3H, s), 5.14 (1H, d, J=5 Hz), 5.66 (1H, dd, J=5 Hz, 8 Hz), 6.9 (1H, m), 7.48 (1H, d, J=8 Hz), 7.80 (1H, dd, J=8 Hz, 9 Hz), 9.3 (1H, m), 9.42 (1H, d, J=8 Hz), 10.5 (1H, m).

(4) 7-[2-(6-Aminopyridin-2-yl)-2-methoxyiminoacetamido]-3-(1-methyl-1H-tetrazol-5-yl)thiomethyl-3-cephem-4-carboxylic acid (syn isomer).

I.R. $\nu_{max}^{Nujol}$: 3360, 3220, 1780, 1670, 1620, 1585, 1544, 1042 cm$^{-1}$.

(5) 7-[2-(6-aminopyridin-2-yl)-2-methoxyiminoacetamido]-3-cephem-4-carboxylic acid.

I.R. $\nu_{max}^{Nujol}$: 3300, 1785, 1730, 1670 cm$^{-1}$.

(6) 7-[2-(6-Aminopyridin-2-yl)-2-methoxyiminoacetamido]-3-(1,3,4-thiadiazol-2-yl)thiomethyl-3-cephem-4-carboxylic acid (syn isomer).

I.R. $\nu_{max}^{Nujol}$: 3400, 3230, 1780, 1670, 1622, 1590, 1550, 1050 cm$^{-1}$.

(7) 7-[2-(6-Aminopyridin-2-yl)-2-methoxyiminoacetamido]-3-(5-aminomethyl-1,3,4-thiadiazol-2-yl)thiomethyl-3-cephem-4-carboxylic acid (syn isomer).

I.R. $\nu_{max}^{Nujol}$: 3500, 3400, 3230, 1770, 1670, 1620, 1040 cm$^{-1}$.

(8) 7-[2-(6-Aminopyridin-2-yl)-2-methoxyiminoacetamido]-3-(1-carboxymethyl-1H-tetrazol-5-yl)thiomethyl-3-cephem-4-carboxylic acid (syn isomer).

I.R. $\nu_{max}^{Nujol}$: 3380, 3220, 1780, 1670, 1620, 1050 cm$^{-1}$.

(9) 7-[2-(6-Aminopyridin-2-yl)acetamido]-3-(1-methyl-1H-tetrazol-5-yl)thiomethyl-3-cephem-4-carboxylic acid (syn isomer).

I.R. $\nu_{max}^{Nujol}$: 3600-3080, 1763, 1698, 1663 cm$^{-1}$.

(10) 7-[2-(6-Aminopyridin-2-yl)-2-methoxyiminoacetamido]-3-chloro-3-cephem-4-carboxylic acid hydrochloride (syn isomer).

I.R. $\nu_{max}^{Nujol}$: 3300-3100, 1780, 1710, 1660, 1610, 1540, 1370 cm$^{-1}$.

(11) 7-[2-(6-Aminopyridin-2-yl)-2-methoxyiminoacetamido]-3-methoxy-3-cephem-4-carboxylic acid.

I.R. $\nu_{max}^{Nujol}$: 3300, 1775, 1700-1650, 1045 cm$^{-1}$.

(12) 7-[2-(6-Aminopyridin-2-yl)-2-methoxyiminoacetamido]-7-methoxy-3-(1-methyl-1H-tetrazol-5-yl)thiomethyl-3-cephem-4-carboxylic acid (syn isomer).

I.R. $\nu_{max}^{Nujol}$: 3300, 1780, 1700, 1680 cm$^{-1}$.

(13) 7-[2-(6-Aminopyridin-2-yl)-2-methoxyiminoacetamido]-2-methyl-3-cephem-4-carboxylic acid (syn isomer).

I.R. $\nu_{max}^{Nujol}$: 3400-3100, 1780, 1730, 1665, 1550, 1295, 1258, 1050 cm$^{-1}$.

(14) 7-[2-(6-Aminopyridin-2-yl)-2-methoxyiminoacetamido]-3-methyl-3-cephem-4-carboxylic acid hydrochloride (syn isomer).

I.R. $\nu_{max}^{Nujol}$: 3100, 1780, 1682, 1668, 1260, 1050 cm$^{-1}$.

(15) 7-[2-(6-Aminopyridin-2-yl)-2-hydroxyiminoacetamido]-3-(1-methyl-1H-tetrazol-5-yl)thiomethyl-3-cephem-4-carboxylic acid (syn isomer).

I.R. $\nu_{max}^{Nujol}$: 3300, 1760, 1680 cm$^{-1}$.

(16) 7-[2-(6-Aminopyridin-2-yl)-2-methoxyiminoacetamido]-3-carbamoyloxymethyl-3-cephem-4-carboxylic acid (syn isomer).

I.R. $\nu_{max}^{Nujol}$: 3400, 1780, 1720, 1670 cm$^{-1}$.

(17) 7-[2-(2-Aminopyrimidin-4-yl)-2-methoxyiminoacetamido]-3-(1-methyl-1H-tetrazol-5-yl)thiomethyl-3-cephem-4-carboxylic acid.

I.R. $\nu_{max}^{Nujol}$: 3440, 3320, 1790, 1693, 1660, 1630, 1525, 1043 cm$^{-1}$.

(18) 7-[2-(6-Aminopyridin-2-yl)-2-ethoxyiminoacetamido]-3-(1-methyl-1H-tetrazol-5-yl)thiomethyl-3-cephem-4-carboxylic acid (syn isomer).

I.R. $\nu_{max}^{Nujol}$: 3380, 3240, 1780, 1670 cm$^{-1}$.

(19) 7-[2-(6-Aminopyridin-2-yl)-2-methoxyiminoacetamido]cephalosporanic acid (syn isomer).

I.R. $\nu_{max}^{Nujol}$: 3350-3220, 1780, 1740, 1680-1655, 1380, 1040 cm$^{-1}$.

(20) 7-[2-(4-Aminopyrimidin-2-yl)-2-methoxyiminoacetamido]-3-(1-methyl-1H-tetrazol-5-ylthiomethyl)-3-cephem-4-carboxylic acid (a mixture of syn and anti isomer).

I.R. $\nu_{max}^{Nujol}$: 3380, 3220, 1780, 1700-1620, 1240, 1040 cm$^{-1}$.

(21) 7-[2-Allyloxyimino-2-(6-aminopyridin-2-yl)acetamido]-3-(1-methyl-1H-tetrazol-5-ylthiomethyl)-3-cephem-4-carboxylic acid (syn isomer).

I.R. $\nu_{max}^{Nujol}$: 3380, 3310, 1780, 1670, 1620 cm$^{-1}$.

(22) 7-[2-(6-Aminopyridin-2-yl)-2-propargyloxyiminoacetamido]-3-(1-methyl-1H-tetrazol-5-ylthiomethyl)-3-cephem-4-carboxylic acid (syn isomer).

I.R. $\nu_{max}^{Nujol}$: 3270, 1765, 1690, 1665, 1620, 1580, 1530 cm$^{-1}$.

(23) 7-[2-(2-Amino-6-chloropyrimidin-4-yl)-2-methoxyiminoacetamido]-3-(1-methyl-1H-tetrazol-5-ylthiomethyl)3-cephem-4-carboxylic acid hydrochloride.

I.R. $\nu_{max}^{Nujol}$: 3300-3100, 1785, 1660, 1390, 1050 cm$^{-1}$.

(24) 7-[2-(4-Aminopyridin-2-yl)-2-methoxyiminoacetamido]-3-(1-methyl-1H-tetrazol-5-ylthiomethyl)-3-cephem-4-carboxylic acid (syn isomer).

I.R. $\nu_{max}^{Nujol}$: 3400, 3230, 1778, 1650, 1600, 1380, 1050 cm$^{-1}$.

(25) 7-[2-(6-Aminopyridin-2-yl)-2-propoxyiminoacetamido]-3-(1-methyl-1H-tetrazol-5-ylthiomethyl)-3-cephem-4-carboxylic acid (syn isomer).

I.R. $\nu_{max}^{Nujol}$: 3400, 3250, 1780, 1670, 1625, 1590, 1550 cm$^{-1}$.

(26) 7-[2-(6-Aminopyridin-2-yl)-2-isopropoxyiminoacetamido]-3-(1-methyl-1H-tetrazol-5-ylthiomethyl)-3-cephem-4-carboxylic acid (syn isomer).

I.R. $\nu_{max}^{Nujol}$: 3380, 3240, 1780, 1670, 1620 cm$^{-1}$.

(27) 7-[2-(6-Aminopyridin-2-yl)-2-isobutoxyiminoacetamido]-3-(1-methyl-1H-tetrazol-5-ylthiomethyl)-3-cephem-4-carboxylic acid (syn isomer).

I.R. $\nu_{max}^{Nujol}$: 3370, 3220, 1780, 1670, 1620 cm$^{-1}$.

(28) 7-[2-(2-Aminopyridin-4-yl)-2-methoxyiminoacetamido]-3-(1-methyl-1H-tetrazol-5-ylthiomethyl)-3-cephem-4-carboxylic acid (syn isomer).

I.R. $\nu_{max}^{Nujol}$: 3200, 1775, 1670, 1600, 1560 cm$^{-1}$.

(29) 7-[2-(6-Aminopyridin-2-yl)-2-ethoxyiminoacetamido]-2-methyl-3-cephem-4-carboxylic acid (syn isomer).

I.R. $\nu_{max}^{Nujol}$: 3350, 3150, 1795, 1730, 1670 cm$^{-1}$.

(30) 7-[2-(6-Aminopyridin-2-yl)-2-propoxyiminoacetamido]-2-methyl-3-cephem-4-carboxylic acid (syn isomer).

I.R. $\nu_{max}^{Nujol}$: 3340, 3150, 1780, 1735, 1670 cm$^{-1}$.

(31) 7-[2-(6-Aminopyridin-2-yl)-2-isopropoxyiminoacetamido]-2-methyl-3-cephem-4-carboxylic acid (syn isomer).

I.R. $\nu_{max}^{Nujol}$: 3350, 3150, 1795, 1735, 1670 cm$^{-1}$.

(32) 7-[2-(6-Aminopyridin-2-yl)-2-butoxyiminoacetamido]-3-(1-methyl-1H-tetrazol-5-ylthiomethyl)-3-cephem-4-carboxylic acid (syn isomer).

I.R. $\nu_{max}^{Nujol}$: 3350, 3200, 1775, 1670, 1620, 1585, 1540 cm$^{-1}$.

(33) 7-[2-(6-Aminopyridin-2-yl)-2-butoxyiminoacetamido]-2-methyl-3-cephem-4-carboxylic acid (syn isomer).

I.R. $\nu_{max}^{Nujol}$: 3400, 3120, 1785, 1660 cm$^{-1}$.

(34) 7-[2-(6-Aminopyridin-2-yl)-2-isobutoxyiminoacetamido]-2-methyl-3-cephem-4-carboxylic acid (syn isomer).

I.R. $\nu_{max}^{Nujol}$: 3300, 1785, 1735, 1660 cm$^{-1}$.

(35) 7-[2-Allyloxyimino-2-(6-aminopyridin-2-yl)acetamido]-2-methyl-3-cephem-4-carboxylic acid (syn isomer).

I.R. $\nu_{max}^{Nujol}$: 3350, 3150, 1795, 1735, 1670 cm$^{-1}$.

(36) 7-[2-(6-Aminopyridin-2-yl)-2-propargyloxyiminoacetamido]-2-methyl-3-cephem-4-carboxylic acid (syn isomer).

I.R. $\nu_{max}^{Nujol}$: 3350, 1780, 1670 cm$^{-1}$.

(37) 7-[2-(6-Aminopyridin-2-yl)-2-(2,2,2-trifluoroethoxyimino)acetamido]-3-(1-methyl-1H-tetrazol-5-ylthiomethyl)-3-cephem-4-carboxylic acid (syn isomer).

I.R. $\nu_{max}^{Nujol}$: 3400, 1780, 1690 cm$^{-1}$.

(38) 7-[2-(6-Aminopyridin-2-yl)-2-phenoxyiminoacetamido]-2-methyl-3-cephem-4-carboxylic acid (syn isomer).

I.R. $\nu_{max}^{Nujol}$: 3200, 1760, 1690, 1670 cm$^{-1}$.

(39) 7-[2-(6-Aminopyridin-3-yl)-2-methoxyiminoacetamido]-3-(1-methyl-1H-tetrazol-5-ylthiomethyl)-3-cephem-4-carboxylic acid (syn isomer).

I.R. $\nu_{max}^{Nujol}$: 3380, 3220, 1780, 1680, 1630, 1590, 1550 cm$^{-1}$.

(40) 7-[2-(6-Aminopyridin-3-yl)-2-methoxyiminoacetamido]-3-(1-methyl-1H-tetrazol-5-ylthiomethyl)-3-cephem-4-carboxylic acid (anti isomer).

I.R. $\nu_{max}^{Nujol}$: 3350, 3200, 1780, 1680, 1630, 1520 cm$^{-1}$.

(41) 7-[2-(6-Amino-3-chloropyridin-2-yl)-2-methoxyiminoacetamido]-3-(1-methyl-1H-tetrazol-5-ylthiomethyl)-3-cephem-4-carboxylic acid hydrochloride (syn isomer).

I.R. $\nu_{max}^{Nujol}$: 3350–3100, 1790, 1670, 1550, 1380, 1235, 1040 cm$^{-1}$.

(42) 7-[2-(6-Amino-3,5-dichloropyridin-2-yl)-2-methoxyiminoacetamido]-3-(1-methyl-1H-tetrazol-5-ylthiomethyl)-3-cephem-4-carboxylic acid (syn isomer).

I.R. $\nu_{max}^{Nujol}$: 3300, 1785, 1730, 1660, 1545, 1380, 1235, 1045 cm$^{-1}$.

(43) 7-[2-(4-Aminopyrimidin-2-yl)-2-methoxyiminoacetamido]-3-(1,3,4-thiadiazol-2-ylthiomethyl)-3-cephem-4-carboxylic acid (syn isomer), mp. 164°–171° C. (dec.).

(44) 7-[2-(4-Aminopyrimidin-2-yl)-2-methoxyiminoacetamido]-3-(5-methyl-1,3,4-thiadiazol-2-ylthiomethyl)-3-cephem-4-carboxylic acid (syn isomer), mp. 161°–167° C. (dec.).

(45) 7-[2-(4-Aminopyrimidin-2-yl)-2-methoxyiminoacetamido]cephalosporanic acid (syn isomer), mp. 149°–159° C. (dec.).

EXAMPLE 5

(1) A solution of 7-[2-(6-formamidopyridin-2-yl)-2-methoxyiminoacetamido]cephalosporanic acid (syn isomer) (2.10 g.) and disodium 2-(5-sulfido-1H-tetrazol-1-yl)acetate (2.70 g) in water (40 ml.) was adjusted to pH 7 with sodium bicarbonate, and stirred at 65° C. for 6 hours at pH 7 to 7.4. The resultant solution was washed with ethyl acetate, adjusted to pH 2.5 with 10% hydrochloric acid and stirred. The precipitates were collected by filtration, washed with water and diethyl ether in turn to give 7-[2-(6-formamidopyridin-2-yl)-2-methoxyiminoacetamido]-3-(1-carboxymethyl-1H-tetrazol-5-yl)-thiomethyl-3-cephem-4-carboxylic acid (syn isomer) (1.27 g.), mp. 166° to 168° C. (dec.).

I.R. $\nu_{max}^{Nujol}$: 3300, 1782, 1737, 1670 (broad), 1577, 1247, 1053 cm$^{-1}$.

N.M.R. δ ppm (DMSO-d$_6$): 3.60, 3.72 (2H, AB-q, J=18 Hz), 3.92 (3H, s), 4.23, 4.45 (2H, AB-q, J=13 Hz), 5.12 (1H, d, J=5 Hz), 5.28 (2H, s), 5.83 (1H, dd, J=5 Hz, 8 Hz), 6.88 (1H, broad d, J=8 Hz), 7.50 (1H, d, J=8 Hz), 7.83 (1H, t, J=8 Hz), 9.32 (1H, broad d, J=8 Hz), 9.55 (1H, broad d, J=8 Hz), 10.5–10.8 (1H, m).

The following compounds were prepared in substantially the same manner as that of Example 5-(1).

(2) 7-[2-(6-Aminopyridin-2-yl)-2-methoxyiminoacetamido]-3-(1-methyl-1H-tetrazol-5-yl)thiomethyl-3-cephem-4-carboxylic acid (syn isomer).

I.R. $\nu_{max}^{Nujol}$: 3360, 3220, 1780, 1670, 1620, 1585, 1544, 1042 cm$^{-1}$.

(3) 7-[2-(6-Aminopyridin-2-yl)-2-methoxyiminoacetamido]-3-(1,3,4-thiadiazol-2-yl)-thiomethyl-3-cephem-4-carboxylic acid (syn isomer).

I.R. $\nu_{max}^{Nujol}$: 3400, 3230, 1780, 1670, 1622, 1590, 1550, 1050 cm$^{-1}$.

(4) 7-[2-(6-Aminopyridin-2-yl)-2-methoxyiminoacetamido]-3-(5-aminomethyl-1,3,4-thiadiazol-2-yl)-thiomethyl-3-cephem-4-carboxylic acid (syn isomer).

I.R. $\nu_{max}^{Nujol}$: 3500, 3400, 3230, 1770, 1670, 1620, 1040 cm$^{-1}$.

(5) 7-[2-(6-Aminopyridin-2-yl)-2-methoxyiminoacetamido]-3-(1-carboxymethyl-1H-tetrazol-5-yl)-thiomethyl-3-cephem-4-carboxylic acid (syn isomer).

I.R. $\nu_{max}^{Nujol}$: 3380, 3220, 1780, 1670, 1620, 1050 cm$^{-1}$.

(6) 7-[2-(6-Aminopyridin-2-yl)acetamido]-3-(1-methyl-1H-tetrazol-5-yl)thiomethyl-3-cephem-4-carboxylic acid (syn isomer).

I.R. $\nu_{max}^{Nujol}$: 3600–3080, 1763, 1698, 1663 cm$^{-1}$.

(7) 7-[2-(6-Aminopyridin-2-yl)-2-methoxyiminoacetamido]-7-methoxy-3-(1-methyl-1H-tetrazol-5-yl)thio methyl-3-cephem-4-carboxylic acid (syn isomer).

I.R. $\nu_{max}^{Nujol}$: 3300, 1780, 1700, 1680 cm$^{-1}$.

(8) 7-[2-(6-Aminopyridin-2-yl)-2-hydroxyiminoacetamido]-3-(1-methyl-1H-tetrazol-5-yl)thiomethyl-3-cephem-4-carboxylic acid (syn isomer).

I.R. $\nu_{max}^{Nujol}$: 3300, 1760, 1680 cm$^{-1}$.

(9) 7-[2-(2-Aminopyrimidin-4-yl)-2-methoxyiminoacetamido]-3-(1-methyl-1H-tetrazol-5-yl)-thiomethyl-3-cephem-4-carboxylic acid.

I.R. $\nu_{max}^{Nujol}$: 3440, 3320, 1790, 1693, 1660, 1630, 1525, 1043 cm$^{-1}$.

(10) 7-[2-(6-Aminopyridin-2-yl)-2-ethoxyiminoacetamido]-3-(1-methyl-1H-tetrazol-5-yl)thiomethyl-3-cephem-4-carboxylic acid (syn isomer).

I.R. $\nu_{max}^{Nujol}$: 3380, 3240, 1780, 1670 cm$^{-1}$.

(11) 7-[2-(4-Aminopyrimidin-2-yl)-2-methoxyiminoacetamido]-3-(1-methyl-1H-tetrazol-5-ylthiomethyl)-3-cephem-4-carboxylic acid (a mixture of syn and anti isomer).

I.R. $\nu_{max}^{Nujol}$: 3380, 3220, 1780, 1700–1620, 1240, 1040 cm$^{-1}$.

(12) 7-[2-(Allyloxyimino-2-(6-aminopyridin-2-yl)-acetamido]-3-(1-methyl-1H-tetrazol-5-ylthiomethyl)-3-cephem-4-carboxylic acid (syn isomer).

I.R. (4 $_{max}^{Nujol}$: 3380, 3310, 1780, 1670, 1620 cm$^{-1}$.

(13) 7-[2-(6-Aminopyridin-2-yl)-2-propargyloxyiminoacetamido]-3-(1-methyl-1H-tetrazol-5-ylthiomethyl)-3-cephem-4carboxylic acid (syn isomer).

I.R. $\nu_{max}^{Nujol}$: 3270, 1765, 1690, 1665, 1620, 1580, 1530 cm$^{-1}$.

(14) 7-[2-(2-Amino-6-chloropyrimidin-4-yl)-2-methoxyiminoacetamido]-3-(1-methyl-1H-tetrazol-5-ylthiomethyl)-3-cephem-4-carboxylic acid hydrochloride.

I.R. $\nu_{max}^{Nujol}$: 3300–3100, 1785, 1660, 1390, 1050 cm$^{-1}$.

(15) 7-[2-(4-Aminopyridin-2-yl)-2-methoxyiminoacetamido]-3-(1-methyl-1H-tetrazol-5-ylthiomethyl)-3-cephem-4-carboxylic acid (syn isomer).

I.R. $\nu_{max}^{Nujol}$: 3400, 3230, 1778, 1650, 1600, 1380, 1050 cm$^{-1}$.

(16) 7-[2-(6-Aminopyridin-2-yl)-2-propoxyiminoacetamido]-3-(1-methyl-1H-tetrazol-5-ylthiomethyl)-3-cephem-4-carboxylic acid (syn isomer).

I.R. $\nu_{max}^{Nujol}$: 3400, 3250, 1780, 1670, 1625, 1590, 1550 cm$^{-1}$.

(17) 7-[2-(6-Aminopyridin-2-yl)-2-isopropoxyiminoacetamido]-3-(1-methyl-1H-tetrazol-5-ylthiomethyl)-3-cephem-4-carboxylic acid (syn isomer).

I.R. $\nu_{max}^{Nujol}$: 3380, 3240, 1780, 1670, 1620 cm$^{-1}$.

(18) 7-[2-(6-Aminopyridin-2-yl)-2-isobutoxyiminoacetamido]-3-(1-methyl-1H-tetrazol-5-ylthiomethyl)-3-cephem-4-carboxylic acid (syn isomer).

I.R. $\nu_{max}^{Nujol}$: 3370, 3220, 1780, 1670, 1620 cm$^{-1}$.

(19) 7-[2-(2-Aminopyridin-4-yl)-2-methoxyiminoacetamido]-3-(1-methyl-1H-tetrazol-5-ylthiomethyl)-3-cephem-4-carboxylic acid (syn isomer).

I.R. $\nu_{max}^{Nujol}$: 3200, 1775, 1670, 1600, 1560 cm$^{-1}$.

(20) 7-82-(6-Aminopyridin-2-yl)-2-butoxyiminoacetamido]-3-(1-methyl-1H-tetrazol-5-ylthiomethyl)-3-cephem-4-carboxylic acid (syn isomer).

I.R. $\nu_{max}^{Nujol}$: 3350, 3200, 1775, 1670, 1620, 1585, 1540 cm$^{-1}$.

(21) 7-[2-(6-Aminopyridin-2-yl)-2-(2,2,2-trifluoroethoxyimino)acetamido]-3-(1-methyl-1H-tetrazol-5-ylthiomethyl)-3-cephem-4-carboxylic acid (syn isomer).

I.R. $\nu_{max}^{Nujol}$: 3400, 1780, 1690 cm$^{-1}$.

(22) 7-[2-(6-Aminopyridin-3-yl)-2-methoxyiminoacetamido]-3-(1-methyl-1H-tetrazol-5-ylthiomethyl)-3-cephem-4-carboxylic acid (syn isomer).

I.R. $\nu_{max}^{Nujol}$: 3380, 3220, 1780, 1680, 1630, 1590, 1550 cm$^{-1}$.

(23) 7-[2-(6-Aminopyridin-3-yl)-2-methoxyiminoacetamido]-3-(1-methyl-1H-tetrazol-5-ylthiomethyl)-3-cephem-4-carboxylic acid (anti isomer).

I.R. $\nu_{max}^{Nujol}$: 3350, 3200, 1780, 1680, 1630, 1520 cm$^{-1}$.

(24) 7-[2-(6-Amino-3-chloropyridin-2-yl)-2-methoxyiminoacetamido]-3-(1-methyl-1H-tetrazol-5-ylthiomethyl)-3-cephem-4-carboxylic acid hydrochloride (syn isomer).

I.R. $\nu_{max}^{Nujol}$: 3350–3100, 1790, 1670, 1550, 1380, 1235, 1040 cm$^{-1}$.

(25) 7-[2-(6-Amino-3,5-dichloropyridin-2-yl)-2-methoxyiminoacetamido]-3-(1-methyl-1H-tetrazol-5-ylthiomethyl)-3-cephem-4-carboxylic acid (syn isomer).

I.R. $\nu_{max}^{Nujol}$: 3300, 1785, 1730, 1660, 1545, 1380, 1235, 1045 cm$^{-1}$.

(26) 7-[2-(4-Aminopyrimidin-2-yl)-2-methoxyiminoacetamido]-3-(1,3,4-thiadiazol-2-ylthiomethyl)-3-cephem-4-carboxylic acid (syn isomer), mp 164°–171° C. (dec.).

(27) 7-[2-(4-Aminopyrimidin-2-yl)-2-methoxyiminoacetamido]-3-(5-methyl-1,3,4-thiadiazol-2-ylthiomethyl)-3-cephem-4-carboxylic acid (syn isomer), mp 161°–167° C. (dec.).

EXAMPLE 6

To phosphoryl chloride (2.6 g.) was added N,N-dimethylformamide (4 ml.) and the mixture was stirred at 40° to 50° C. for 30 minutes, and then methylene chloride (20 ml.) was added thereto. To this mixture was added 2-(4-formamidopyrimidin-2-yl)-2-methoxyiminoacetic acid (1.9 g.) under cooling at −20° to −15° C. with stirring, and the stirring was continued at the same temperature for 30 minutes.

On the other hand, 7-amino-3-(1-methyl-1H-tetrazol-5-ylthiomethyl)-3-cephem-4-carboxylic acid and trimethylsilylacetamide (11 g.) were added to methylene chloride (66 ml.) and the mixture was stirred at ambient temperature for an hour, and to this solution was added all at once the above activated solution of 2-(4-formamidopyrimidin-2-yl)-2-methoxyiminoacetic acid under cooling at −20° C. with stirring, and the stirring was continued at the same temperature for an hour and at ambient temperature for additional an hour. The reaction mixture was concentrated under reduced pressure and then ethyl acetate and an aqueous solution of sodium bicarbonate were added to adjust the solution to pH 7 to 8. After the aqueous layer was separated out, a proper quantity of ethyl acetate was added thereto. The mixture was adjusted to pH 1 to 2 with dilute hydrochloric acid and then salted out. The ethyl acetate layer was separated out, washed with an aqueous solution of sodium chloride and dried over magnesium sulfate, and then evaporated to dryness under reduced pressure. The resultant foamy substance was pulverised in ethyl ether, collected by filtration and then dried to give 7-[2-(4-formamidopyrimidin-2-yl)-2-methoxyiminoacetamido]-3-(1-methyl-1H-tetrazol-5-ylthiomethyl)-3-cephem-4-carboxylic acid (2.9 g.). Thus obtained product (0.6 g.) was dissolved in a mixed solution of methanol and ethyl acetate (5 ml.)(2:1 by volume), and the solution was poured into ethyl ether (40 ml.) and then the mixture was allowed to stand for a while. The precipitates were collected by filtration to give purified pale-yellowish powder of 7-[2-(4-formamidopyrimidin-2-yl)-2-methoxyiminoacetamido]-3-(1-methyl-1H-tetrazol-5-ylthiomethyl)-3-cephem-4-carboxylic acid (a mixture of syn and anti isomers) (0.5 g.).

I.R. $\nu_{max}^{Nujol}$: 3300, 1785, 1650–1730, 1570, 1240, 1175, 1040, 720 cm$^{-1}$.

N.M.R. δppm (DMSO-d$_6$) : 3.70 (2H, m)
3.92 (3H, s)
3.92 (s)
3.99 (s)  } (3H)
4.20 and 4.30 (2H, ABq, J = 15Hz)
5.05 (d, J = 5Hz)
5.15 (d, J = 5Hz)  } (1H)
5.60 (m)
5.80 (d,d, J = 5Hz, 9Hz)  } (1H)
6.90–7.60 (1H, m)
8.61 (1H, d, J = 5Hz)
8.76 (d, J = 9Hz)
9.51 (d, J = 9Hz)  } (1H)
11.10 (1H, broad s)

EXAMPLE 7

To phosphoryl chloride (1.6 g.) was added N,N-dimethylformamide (8 ml.) and the mixture was stirred at 40° C. for 30 minutes. To this mixture was added a solution of 2-allyloxyimino-2-(6-formamidopyridin-2-yl)acetic acid (syn isomer) (2.0 g.) in N,N-dimethylformamide (8 ml.) under cooling at −15° C. with stirring and the stirring was continued at −10° to −8° C. for an hour.

On the other hand, 7-amino-3-(1-methyl-1H-tetrazol-5-ylthiomethyl)-3-cephem-4-carboxylic acid (3.2 g.) and trimethylsilylacetamide (11.5 g.) were added to methylene chloride (35 ml.), and the mixture was stirred at 30° C. till it became a solution and then cooled to −15° C.

To this solution was added the above obtained N,N-dimethylformamide solution under cooling at −15° C. with stirring, and the stirring was continued at the same temperature for an hour. After the reaction mixture was poured into an aqueous solution (80 ml.) of sodium bicarbonate (3.2 g.), the aqueous layer was separated out, washed with ethyl acetate. To the aqueous solution was added ethyl acetate and the mixture was adjusted to pH 3 to 4 with 5% hydrochloric acid. The ethyl acetate layer was separated out and the remaining aqueous solution was extracted twice with ethyl acetate. The ethyl acetate solution and these extracts were combined together, dried and then evaporated to dryness under reduced pressure. The residue was crystallized from water, collected by filtration and then dried to give 7-[2-allyloxyimino-2-(6-formamidopyridin-2-yl)acetamido]-3-(1-methyl-1H-tetrazol-5-ylthiomethyl)-3-cephem-4-carboxylic acid (syn isomer) (1.81 g.), mp. 132°–135° C. (dec.)

I.R. $\nu_{max}^{Nujol}$: 3300, 1785, 1670, 1580, 1545 cm$^{-1}$.

N.M.R. δ ppm [acetone-d$_6$ and D$_2$O]: 3.83 (2H, broad s), 4.00 (3H, s), 4.43 (2H, broad s), 4.70–4.87 (2H, m), 5.27 (1H, d, J = 5 Hz), 5.13–5.60 (2H, m), 5.83–6.27 (2H, m), 7.00–8.00 (3H, m).

EXAMPLE 8-(1)

To phosphoryl chloride (1.61 g.) was added N,N-dimethylformamide (8 ml.) and the mixture was stirred at 40° C. for 30 minutes. To this mixture was added a solution of 2-(6-formamidopyridin-2-yl)-2-propargyloxyiminoacetic acid (syn isomer) (2.0 g.) in N,N-dimethylformamide (8 ml.) under cooling at −15° C. with stirring, and the stirring was continued at −10° to −8° C. for 40 minutes.

On the other hand, 7-amino-3-(1-methyl-1H-tetrazol-5-ylthiomethyl)-3-cephem-4-carboxylic acid (3.25 g.) and trimethylsilylacetamide (10.5 g.) were added to methylene chloride (40 ml.), and the mixture was stirred at 30° C. till it became a solution.

To the solution was added the above obtained N,N-dimethylformaide mixture under cooling at −15° C. with stirring, and the stirring was continued at the same temperature for an hour. After the reaction mixture was poured into an aqueous solution (80 ml.) of sodium bicarbonate (4.0 g.), the aqueous layer was separated out. The remaining methylene chloride solution was extracted with an aqueous solution of sodium bicarbonate. Thus obtained aqueous layer and extract were combined together, and adjusted to pH 2 with 10% hydrochloric acid and then extracted with ethyl acetate. The extract was washed with water, dried and then evaporated to dryness under reduced pressure. The residue was pulverized in water, collected by filtration and then dried to give 7-[2-(6-formamidopyridin-2-yl)-2-propargyloxyiminoacetamido]-3-(1-methyl-1H-tetrazol-5-ylthiomethyl)-3-cephem-4-carboxylic acid (syn isomer) (2.41 g.), mp. 123°-125° C. (dec.).

I.R. $\nu_{max}^{Nujol}$: 3300, 1780, 1670, 1575, 1540 cm$^{-1}$.

N.M.R. δ ppm (acetone-d$_6$ and D$_2$O): 3.07 (1H, t, J=2 Hz), 3.83 (2H, s), 4.00 (3H, s), 4.43 (2H, s), 4.87 (2H, d, J=2 Hz), 5.27 (1H, d, J=5 Hz), 6.07 (1H, d, J=5 Hz), 7.00–8.07 (3H, m).

The following compounds were obtained according to similar manners to those of Examples 6 to 8-(1).

(2) 7-[2-(2-Formamidopyridin-4-yl)-2-methoxyiminoacetamido]-3-(1-methyl-1H-tetrazol-5-ylthiomethyl)-3-cephem-4-carboxylic acid (syn isomer), mp. 138°-140° C. (dec.).

I.R. $\nu_{max}^{Nujol}$: 3250, 1780, 1680, 1610, 1550 cm$^{-1}$.

N.M.R. δ ppm (DMSO-d$_6$): 3.73 (2H, broad s), 3.97 (3H, s), 4.03 (3H, s), 4.40 (2H, broad s), 5.23 (1H, d, J=5 Hz), 5.90 (1H, d,d, J=5 Hz, 8 Hz), 7.13–8.53 (3H, m), 9.87 (1H, d, J=8 Hz), 10.73 (1H, d, J=6 Hz)

(3) 7-[2-(4-Formamidopyridin-2-yl)-2-methoxyiminoacetamido]-3-(1-methyl-1H-tetrazol-5-ylthiomethyl)-3-cephem-4-carboxylic acid (syn isomer), mp. 160°-166° C. (dec.).

I.R. $\nu_{max}^{Nujol}$: 3300, 1780, 1690, 1590, 1520, 1380, 1040 cm$^{-1}$.

N.M.R. δ ppm (DMSO-d$_6$): 3.70 (2H, m), 3.95 (6H, s), 4.32 (2H, broad s), 5.15 (1H, d, J=4.5 Hz) 5.85 (1H, d,d, J=4.5 Hz, 8.0 Hz), 8.10–8.50 (4H, m), 9.52 (1H, d, J=8 Hz)

(4) 7-[2-(6-Chloro-2-formamidopyrimidin-4-yl)-2-methoxyiminoacetamido]-3-(1-methyl-1H-tetrazol-5-ylthiomethyl)-3-cephem-4-carboxylic acid (syn and anti mixture).

I.R. $\nu_{max}^{Nujol}$: 3200–3300, 1780, 1700, 1680, 1550, 1380, 1040 cm$^{-1}$.

| N.M.R. δppm (DMSO-d$_6$) : | 3.75 (2H, m) |
|---|---|
| | 3.98 (3H, s) |
| | 4.01 (3H, s) |
| | 4.35 (2H, m) |
| | 5.20 |
| | (1H, d, J = 4.5Hz) |
| | 5.90 (1H, m) |
| | 6.80 (s) ⎫ (1H) |
| | 6.90 (s) ⎭ |
| | 9.41 (d, J = 8Hz) ⎫ (1H) |
| | 9.69 (d, J = 8Hz) ⎭ |
| | 9.45 |
| | (1H, d, J = 10Hz) |
| | 11.05 (d, J = 10Hz) ⎫ (1H) |
| | 11.43 (d, J = 10Hz) ⎭ |

(5) 7-[2-(3-Chloro-6-formamidopyridin-2-yl)-2-methoxyiminoacetamido]-3-(1-methyl-1H-tetrazol-5-ylthiomethyl)-3-cephem-4-carboxylic acid (syn isomer), mp. 165°-172° C. (dec.).

I.R. $\nu_{max}^{Nujol}$: 3300, 1790, 1710, 1670, 1645, 1370, 1270, 1050, 725 cm$^{-1}$.

N.M.R. δ ppm (DMSO-d$_6$): 3.68 (2H, m), 3.94 (3H, s), 3.98 (3H, s), 4.20, 4.38 (2H, AB$_q$, J=14 Hz), 5.14 (1H, d, J=4.5 Hz), 5.82 (1H, d,d, J=4.5 Hz, 8 Hz), 6.90 (1H, m), 7.94 (1H, d, J=8 Hz), 9.22 (1H, m), 9.52 (1H, d, J=8 Hz), 10.72 (1H, d, J=8 Hz)

(6) 7-[2-(3,5-Dichloro-6-formamidopyridin-2-yl)-2-methoxyiminoacetamido]-3-(1-methyl-1H-tetrazol-5-ylthiomethyl)-3-cephem-4-carboxylic acid (syn isomer), mp. 149°-155° C. (dec.).

I.R. $\nu_{max}^{Nujol}$: 3250, 1785, 1705, 1688, 1665, 1420, 1255, 1200, 1073, 1050 cm$^{-1}$.

N.M.R. δ ppm (DMSO-d$_6$): 3.70 (2H, m), 3.95 (3H, s), 4.01 (3H, s), 4.33 (2H, broad s), 5.17 (1H, d, J=4.5 Hz), 5.87 (1H, d,d, J=4.5 Hz, 8 Hz), 8.31 (1H, s), 9.18 (1H, d, J=8 Hz), 9.57 (1H, d, J=8 Hz), 10.65 (1H, d, J=8 Hz).

(7) 7-[2-Ethoxyimino-2-(6-formamidopyridin-2-yl)acetamido]-2-methyl-3-cephem-4-carboxylic acid (syn isomer), mp. 183°-186° C. (dec.).

I.R. $\nu_{max}^{Nujol}$: 3350, 3300, 1790, 1730, 1670 cm$^{-1}$.

N.M.R. δ ppm (DMSO-d$_6$): 1.25 (3H, t, J=7 Hz), 1.40 (3H, d, J=7 Hz), 3.75 (1H, m), 4.15 (2H, q, J=7 Hz), 5.10 (1H, d, J=4 Hz), 5.90 (1H, d,d, J=8 Hz, 4 Hz), 6.50 (1H, d, J=6 Hz), 6.70–8.20 (3H, m).

(8) 7-[2-(6-Formamidopyridin-2-yl)-2-propoxyiminoacetamido]-3-(1-methyl-1H-tetrazol-5-ylthiomethyl)-3-cephem-4-carboxylic acid (syn isomer).

I.R. $\nu_{max}^{Nujol}$: 3300, 1785, 1680, 1580, 1550 cm$^{-1}$.

N.M.R. δ ppm (acetone-d$_6$ and D$_2$O): 0.96 (3H, t, J=7 Hz), 1.64–1.84 (2H, m), 3.72, 3.82 (2H, AB$_q$, J=18 Hz), 3.96 (3H, s), 4.16 (2H, t, J=7 Hz), 4.40 (2H, broad s), 5.20 (1H, d, J=5 Hz), 6.00 (1H, d, J=5 Hz), 6.88–8.20 (3H, m).

(9) 7-[2-Isopropoxyimino-2-(6-formamidopyridin-2-yl)acetamido]-3-(1-methyl-1H-tetrazol-5-ylthiomethyl)-3-cephem-4-carboxylic acid (syn isomer).

I.R. $\nu_{max}^{Nujol}$: 3300, 1785, 1680, 1580, 1540 cm$^{-1}$.

N.M.R. δ ppm (acetone-d$_6$ and D$_2$O): 1.32 (6H, d, J=6 Hz), 3.76, 3.88 (2H, AB$_q$, J=18 Hz), 3.98 (3H, s), 4.40 (2H, broad s), 4.36–4.64 (1H, m), 5.24 (1H, d, J=5 Hz), 6.04 (1H, d, J=5 Hz), 6.92–8.20 (3H, m).

(10) 7-[2-(6-Formamidopyridin-2-yl)-2-propoxyiminoacetamido]-2-methyl-3-cephem-4-carboxylic acid (syn isomer), mp. 145°-150° C. (dec.).

I.R. $\nu_{max}^{Nujol}$: 3300, 1790, 1680 cm$^{-1}$.

N.M.R. δ ppm (DMSO-d$_6$): 0.95 (3H, t, J=8 Hz), 1.45 (3H, d, J=7 Hz), 1.40–1.90 (2H, m), 3.83 (1H, m), 4.17 (2H, t, J=6 Hz), 5.17 (1H, d, J=4 Hz), 6.00 (1H, d,d, J=4 Hz, 8 Hz), 6.58 (1H, d, J=6 Hz), 6.80–8.20 (3H, m).

(11) 7-[2-Isopropoxyimino-2-(6-formamidopyridin-2-yl)-acetamido]-2-methyl-3-cephem-4-carboxylic acid (syn isomer), mp 160°-163° C.

I.R. $\nu_{max}^{Nujol}$: 3300, 1790, 1735, 1670 cm$^{-1}$.

N.M.R. δ ppm (DMSO-d$_6$): 1.30 (6H, d, J=6 Hz), 1.45 (3H, d, J=7 Hz), 3.80 (1H, m), 4.45 (1H, m), 5.15 (1H, d, J=4 Hz), 6.00 (1H, d,d, J=4 Hz, 8 Hz), 6.58 (1H, d, J=6 Hz), 6.80–8.20 (3H, m).

(12) 7-[2-Butoxyimino-2-(6-formamidopyridin-2-yl)-acetamido]-3-(1-methyl-1H-tetrazol-5-ylthiomethyl)-3-cephem-4-carboxylic acid (syn isomer), mp. 153°-155° C. (dec.).

I.R. $\nu_{max}^{Nujol}$: 3300, 1785, 1670, 1580, 1550 cm$^{-1}$.

N.M.R. δ ppm (acetone-d$_6$ and D$_2$O): 0.80–1.07 (3H, m), 1.23–1.83 (4H, m), 3.83 (2H, broad s), 3.97 (3H, s), 4.23 (2H, t, J=6 Hz), 4.43 (2H, broad s), 5.27 (1H, d, J=5 Hz), 6.10 (1H, d, J=5 Hz), 6.97–8.00 (3H, m).

(13) 7-[2-(6-Formamidopyridin-2-yl)-2-isobutoxyiminoacetamido]-3-(1-methyl-1H-tetrazol-5-ylthiomethyl)-3-cephem-4-carboxylic acid (syn isomer), mp. 118°-120° C. (dec.).

I.R. $\nu_{max}^{Nujol}$: 3500, 3300, 1785, 1680, 1580, 1550 cm$^{-1}$.

N.M.R. δ ppm (DMSO-d$_6$): 0.93 (6H, d, J=6 Hz), 1.77–2.17 (1H, m), 3.70 (2H, broad s), 3.93 (3H, s), 4.00

(2H, d, J=6 Hz), 4.33 (2H, broad s), 5.18 (1H, d, J=5 Hz), 5.90 (1H, d,d, J=5 Hz, 9 Hz), 6.83–8.00 (3H, m).

(14) 7-[2-Butoxyimino-2-(6-formamidopyridin-2-yl)-acetamido]-2-methyl-3-cephem-4-carboxylic acid (syn isomer), mp. 155°–160° C. (dec.).

I.R. $\nu_{max}^{Nujol}$: 3300, 1790, 1680 cm$^{-1}$.

N.M.R. δ ppm (DMSO-d$_6$): 0.83–1.83 (10H, m), 3.67–4.00 (1H, m), 4.27 (3H, t, J=4 Hz), 5.22 (1H, d, J=4 Hz), 6.03 (1H, d,d, J=4 Hz, 8 Hz), 6.62 (1H, d, J=6 Hz), 7.00–8.50 (3H, m).

(15) 7-[2-(6-Formamidopyridin-2-yl)-2-isobutoxyiminoacetamido]-2-methyl-3-cephem-4-carboxylic acid (syn isomer), mp. 152°–154° C. (dec.).

I.R. $\nu_{max}^{Nujol}$: 3300, 1790, 1675 cm$^{-1}$.

N.M.R. δ ppm (DMSO-d$_6$): 0.90 (6H, d, J=6 Hz), 1.42 (3H, d, J=6 Hz), 2.00 (1H, m), 3.80 (1H, m), 3.90 (2H, d, J=6 Hz), 5.10 (1H, d, J=4 Hz), 5.95 (1H, d,d, J=4Hz, 8 Hz), 6.50 (1H, d, J=6 Hz), 6.80–8.20 (3H, m).

(16) 7-[2-Allyloxyimino-2-(6-formamidopyridin-2-yl)-acetamido]-2-methyl-3-cephem-4-carboxylic acid (syn isomer) mp. 128°–132° C. (dec.).

I.R. $\nu_{max}^{Nujol}$: 3300, 1790, 1730, 1670 cm$^{-1}$.

N.M.R. δ ppm (DMSO-d$_6$): 1.45 (3H, d, J=7 Hz), 3.85 (1H, m), 4.70 (2H, d, J=5 Hz), 5.20 (1H, d, J=4 Hz), 5.20–5.50 (2H, m), 5.80–6.20 (1H, m), 6.00 (1H, d,d, J=4 Hz, 8 Hz), 6.60 (1H, d, J=6 Hz), 6.80–8.20 (3H, m).

(17) 7-[2-(6-Formamidopyridin-2-yl)-2-propargyloxyiminoacetamido]-2-methyl-3-cephem-4-carboxylic acid (syn isomer), mp. 134°–137° C. (dec.).

I.R. $\nu_{max}^{Nujol}$: 3300, 1790, 1730, 1670 cm$^{-1}$.

N.M.R. δ ppm (DMSO-d$_6$): 1.45 (3H, d, J=7 Hz), 3.50 (1H, t, J=2 Hz), 3.80 (1H, m), 4.85 (2H, d, J=2 Hz), 5.15 (1H, d, J=4 Hz), 6.00 (1H, d,d, J=4 Hz, 8 Hz), 6.58 (1H, d, J=6 Hz), 6.80–8.20 (3H, m).

(18) 7-[2-(2,2,2-Trifluoroethoxyimino)-2-(6-formamidopyridin-2-yl)acetamido]-3-(1-methyl-1H-tetrazol-5-ylthiomethyl)-3-cephem-4-carboxylic acid (syn isomer), mp. 165°–170° C. (dec.).

I.R. $\nu_{max}^{Nujol}$: 3300, 1790, 1690 cm$^{-1}$.

N.M.R. δ ppm (DMSO-d$_6$): 3.70 (2H, broad s), 3.93 (3H, s), 4.32 (2H, broad s), 4.70, 4.95 (2H, AB$_q$, J=9 Hz), 5.15 (1H, d, J=4 Hz), 5.88 (1H, d,d, J=4 Hz, 8 Hz), 7.00–8.00 (3H, m), 9.33 (1H, m), 9.67 (1H, d, J=8 Hz), 10.60 (1H, m).

(19) 7-[2-(6-Formamidopyridin-2-yl)-2-phenoxyiminoacetamido]-2-methyl-3-cephem-4-carboxylic acid (syn isomer), mp. 150°–155° C. (dec.).

I.R. $\nu_{max}^{Nujol}$: 3250, 1780, 1720, 1650 cm$^{-1}$.

N.M.R. δ ppm (DMSO-d$_6$): 1.50 (3H, d, J=7 Hz), 3.90 (1H, m), 5.25 (1H, d, J=4 Hz), 6.10 (1H, d,d, J=4 Hz, 8 Hz), 6.60 (1H, d, J=6 Hz), 7.0–8.2 (8H, m), 9.86 (1H, d, J=8 Hz), 10.73 (1H, d, J=8 Hz).

(20) 7-[2-(6-Formamidopyridin-3-yl)-2-methoxyiminoacetamido-3-(1-methyl-1H-tetrazol-5-ylthiomethyl)-3-cephem-4-carboxylic acid (syn isomer).

I.R. $\nu_{max}^{Nujol}$: 3250, 1780, 1680, 1250, 1175, 1035 cm$^{-1}$.

N.M.R. δ ppm (DMSO-d$_6$): 3.75 (2H, broad s), 3.98 (6H, s), 4.35 (2H, broad s), 5.22 (1H, d, J=5 Hz), 5.87 (1H, d,d, J=5 Hz), 8 Hz), 7.8–8.5 (3H, m), 9.83 (1H, d, J=8 Hz), 10.87 (1H, d, J=7 Hz).

(21) 7-[2-(6-Formamidopyridin-3-yl)-2-methoxyiminoacetamido]-3-(1-methyl-1H-tetrazol-5-ylthiomethyl)-3-cephem-4-carboxylic acid (anti isomer).

I.R. $\nu_{max}^{Nujol}$: 3300, 1780, 1680–1710, 1600, 1240, 1050 cm$^{-1}$.

N.M.R. δ ppm (DMSO-d$_6$): 3.74 (2H, broad s), 3.96 (3H, s), 4.00 (3H, s), 4.00, 4.28 (2H, AB$_q$, J=13 Hz), 5.16 (1H, d, J=5 Hz), 5.72 (1H, d,d, J=5 Hz, 8 Hz), 7.80–8.50 (3H, m), 9.28 (1H, d, J=8 Hz), 10.80 (1H, d, J=6 Hz).

EXAMPLE 9

(1) Phosphoryl chloride (500 mg.) was added dropwise to a suspension of 2-(4-aminopyrimidin-2-yl)-2-methoxyiminoacetic acid (syn isomer) (250 mg.) in ethyl acetate (5 ml.) at 0° to 6° C. with stirring and the stirring was continued at the same temperature for 45 minutes. To this solution was added dropwise N,N-dimethylformamide (0.7 ml.) over a period of 6 minutes at 0° to 6° C. with stirring, and the stirring was continued at the same temperature for 40 minutes. To the resultant solution was added all at once a solution of 7-amino-3-(1-methyl-1H-tetrazol-5-ylthiomethyl)-3-cephem-4-carboxylic acid (365 mg.) and trimethylsilylacetamide (1.5 g.) in ethyl acetate (7 ml.) under cooling at −20° C., and the mixture was stirred at 0° to 6° C. for an hour. The reaction mixture was poured into water (20 ml.) and adjusted to pH 4 with an aqueous solution of sodium bicarbonate. The aqueous layer was separated out and the remaining organic layer was extracted with water. The aqueous layers were combined together and the ethyl acetate remained in the aqueous solution was removed therefrom under reduced pressure. The aqueous solution was subjected to column chromatography on a non-ionic adsorption resin, "Diaion HP-20" (Trade Mark, manufactured by Mitsubishi Chemical Industry Ltd.) (20 ml.). After the column was washed with water, elution was carried out with 5–10% aqueous methanol (100 ml.), 20% aqueous methanol (150 ml.) and 20 to 30% aqueous methanol (150 ml.) in turn, and the fractions containing the desired compound were collected and evaporated to dryness under reduced pressure. The resultant residue was lyophilized to give 7-[2-(4-aminopyrimidin-2-yl)-2-methoxyiminoacetamido]-3-(1-methyl-1H-tetrazol-5-ylthiomethyl)-3-cephem-4-carboxylic acid (syn isomer) (110 mg.), mp. 155° to 158° C.

I.R. $\nu_{max}^{Nujol}$: 3380, 3220, 1780, 1630–1690, 1590, 1040, 840 cm$^{-1}$.

N.M.R. δ ppm (DMSO-d$_6$): 3.65 (2H, m), 3.94 (3H, s), 4.32 (2H, broad s), 5.11 (1H, d, J=5 Hz), 5.80 (1H, d,d, J=5 Hz, 8 Hz), 6.44 (1H, d, J=6 Hz), 7.04 (2H, broad s), 8.10 (1H, d, J=6 Hz), 9.43 (1H, d, J=8 Hz).

The following compounds were obtained according to similar manner to that of Example 9-(1).

(2) 7-[2-Allyloxyimino-2-(6-aminopyridin-2-yl)-acetamido]-3-(1-methyl-1H-tetrazol-5-ylthiomethyl)-3-cephem-4-carboxylic acid (syn isomer), mp. 149°–151° C. (dec).

(3) 7[2-(6-Aminopyridin-2-yl)-2-propargyloxyiminoacetamido]-3-(1-methyl-1H-tetrazol-5-ylthiomethyl)-3-cephem-4-carboxylic acid (syn isomer), mp. 163°–165° C. (dec.).

(4) 7-[2-(2-Aminopyridin-4-yl)-2-methoxyiminoacetamido]-3-(1-methyl-1H-tetrazol-5-ylthiomethyl)-3-cephem-4-carboxylic acid (syn isomer), mp. 175°–177° C. (dec.).

(5) 7-[2-(4-Aminopyridin-2-yl)-2-methoxyiminoacetamido]-3-(1-methyl-1H-tetrazol-5-ylthiomethyl)-3-cephem-4-carboxylic acid (syn isomer), mp. 163°–167° C. (dec.).

(6) 7-[2(2-Amino-6-chloropyrimidin-4-yl)-2-methoxyiminoacetamido]-3-(1-methyl-1H-tetrazol-5-ylthiomethyl)-3-cephem-4-carboxylic acid hydrochloride, mp. 170°–180° C.

(7) 7-[2-(6-Amino-3-chloropyridin-2-yl)-2-methoxyiminoacetamido]-3-(1-methyl-1H-tetrazol-5-ylthiomethyl)-3-cephem-4-carboxylic acid hydrochloride (syn isomer), mp. 155°–160° C. (dec.).

(8) 7-[2-(6-Amino-3,5-dichloropyridin-2-yl)-2-methoxyiminoacetamido]-3-(1-methyl-1H-tetrazol-5-ylthiomethyl)-3-cephem-4-carboxylic acid (syn isomer), mp. 139°–144° C. (dec.).

(9) 7[2-(6-Aminopyridin-2yl)-2-ethoxyiminoacetamido]-2-methyl-3-cephem-4-carboxylic acid (syn isomer), mp. 190°–195° C. (dec.).

(10) 7-[2-(6-Aminopyridin-2-yl)-2-propoxyiminoacetamido]-3-(1-methyl-1H-tetrazol-5-ylthiomethyl)-3-cephem-4-carboxylic acid (syn isomer), 138°–140° C. (dec.).

(11) 7-[2-(6-Aminopyridin-2-yl)-2-isopropoxyiminoacetamido]-3-(1-methyl-1H-tetrazol-5-ylthiomethyl)-3-cephem-4-carboxylic acid (syn isomer), mp. 149°–151° C. (dec.).

(12) 7-[2-(6-Aminopyridin-2-yl)-2-propoxyiminoacetamido]-2-methyl-3-cephem-4-carboxylic acid (syn isomer), mp. 190°–195° C. (dec.).

(13) 7[2-(6-Aminopyridin-2-yl)-2-isopropoxyiminoacetamido]-2-methyl-3-cephem-4carboxylic acid (syn isomer), mp. 185°–188° C. (dec.).

(14) 7-[2-(6-Aminopyridin-2-yl)-2-butoxyiminoacetamido]-3-(1-methyl-1H-tetrazol-5-ylthiomethyl)-3-cephem-4-carboxylic acid (syn isomer), mp. 108°–110° C. (dec.).

(15) 7-[2-(6-Aminopyridin-2-yl)-2-isobutoxyiminoacetamido]-3-(1-methyl-1H-tetrazol-5-ylthiomethyl)-3-cephem-4-carboxylic acid (syn isomer), mp. 140°–142° C. (dec.).

(16) 7-[2-(6-Aminopyridin-2yl)-2-butoxyiminoacetamido]-2-methyl-3-cephem-4-carboxylic acid (syn isomer), mp. 200°–205° C. (dec.).

(17) 7-[2-(6-Aminopyridin-2-yl)-2-isobutoxyiminoacetamido]-2-methyl-3-cephem-4-carboxylic acid (syn isomer), mp. 175°–180° C. (dec.).

(18) 7-[2-Allyloxyimino-2-(6-aminopyrydin-2-yl)-acetamido]-2-methyl-3-cephem-4-carboxylic acid (syn isomer), mp. 168°–173° C. (dec.).

(19) 7-[2-(6-Aminopyridin-2-yl)-2-propargyloxyiminoacetamido]-2-methyl-3-cephem-4-carboxylic acid (syn isomer), mp. 165°–170° C. (dec.).

(20) 7-[2-(6-Aminopyridin-2-yl)-2-(2,2,2-trifluoroethoxyiminoacetamido]-3-(1-methyl-1H-tetrazol-5-ylthiomethyl)-3-cephem-4-carboxylic acid (syn isomer), mp. 165°–170° C. (dec.).

(21) 7-[2-(6-Aminopyridin-2-yl)-2-phenoxyiminoacetamido]-2-methyl-3-cephem-4-carboxylic acid (syn isomer), mp. 145°–147° C. (dec.).

(22) 7-[2-(6-Aminopyridin-3-yl)-2-methoxyiminoacetamido]-3-(1-methyl-1H-tetrazol-5-ylthiomethyl)-3-cephem-4-carboxylic acid (syn isomer), mp. 165°–167° C. (dec.).

(23) 7[2-(6-Aminopyridin-3-yl)-2-methoxyiminoacetamido]-3-(1-methyl-1H-tetrazol-5-ylthiomethyl)-3-cephem-4-carboxylic acid (anti isomer), mp. 153°–155° C. (dec.).

(24) 7-[2-(4-Aminopyrimidin-2-yl)-2-methoxyiminoacetamido]-3-(1,3,4-thiadiazol-2-ylthiomethyl)-3-cephem-4-carboxylic acid (syn isomer), mp 164°–171° C. (dec.).

I.R. $\nu_{max}^{Nujol}$: 3380, 3220, 1780, 1620–1690, 1585, 1540, 1250, 1060, 1040, 895, 830, 720 cm$^{-1}$.

N.M.R. δ ppm (DMSO-d$_6$): 3.73 (2H, broad s), 3.95 (3H, s), 4.28, 4.65 (2H, ABq, J=13 Hz), 5.18 (1H, d, J=5 Hz), 5.87 (1H, d, d, J=5 Hz, 8 Hz), 6.48 (1H, d, J=7 Hz), 7.05 (2H, broad s), 8.15 (1H, d, J=7 Hz), 9.47 (1H, d, J=8 Hz), 9.63 (1H, s).

(25) 7-[2-(4-Aminopyrimidin-2-yl)-2-methoxyiminoacetamido]-3-(5-methyl-1,3,4-thiadiazol-2-ylthiomethyl)-3-cephem-4-carboxylic acid (syn isomer), mp 161°–167° C. (dec.).

I.R. $\nu_{max}^{Nujol}$: 3380, 3220, 1780, 1620–1690, 1585, 1250, 1045, 840, 720 cm$^{-1}$.

N.M.R. δ ppm (DMSO-d$_6$): 2.70 (3H, s), 3.70 (2H, broad s), 3.97 (3H, s), 4.21, 4.58 (2H, ABq, J=13 Hz), 5.22 (1H, d, J=5 Hz), 5.81 (1H, d, d, J=5 Hz, 8 Hz), 6.47 (1H, d, J=7 Hz), 7.05 (2H, broad s), 8.12 (1H, d, J=7 Hz), 9.47 (1H, d, J=8 Hz).

(26) 7-[2-(4-Aminopyrimidin-2-yl)-2-methoxyiminoacetamido]cephalosporanic acid (syn isomer), mp 149°–159° C. (dec.).

I.R. $\nu_{max}^{Nujol}$: 3370, 3220, 1780, 1730, 1630–1680, 1040, 725 cm$^{-1}$.

N.M.R. δ ppm (DMSO-d$_6$): 2.03 (3H, s), 3.36, 3.62 (2H, ABq, J=18 Hz), 3.93 (3H, s), 4.7, 5.0 (2H, ABq, J=12 Hz), 5.10 (1H, d, J=4.5 Hz), 5.77 (1H, d, d, J=4.5 Hz, 8.0 Hz), 6.43 (1H, d, J=6.0 Hz), 8.10 (1H, d, J=6.0 Hz), 9.40 (1H, d, J=8.0 Hz).

(27) 7-[2-(6-Aminopyridin-2-yl)-2-methoxyiminoacetamido]-3-(1-methyl-1H-tetrazol-5-yl)thiomethyl-3-cephem-4-carboxylic acid (syn isomer).

I.R. $\nu_{max}^{Nujol}$: 3360, 3220, 1780, 1670, 1620, 1585, 1544, 1042 cm$^{-1}$.

(28) 7-[2-(6-Aminopyridin-2-yl)-2-methoxyiminoacetamido]-3-cephem-4-carboxylic acid.

I.R. $\nu_{max}^{Nujol}$: 3300, 1785, 1730, 1670 cm$^{-1}$.

(29) 7-[2-(6-Aminopyridin-2-yl)-2-methoxyiminoacetamido]-3-(1,3,4-thiadiazol-2-yl)thiomethyl-3-cephem-4-carboxylic acid (syn isomer).

I.R. $\nu_{max}^{Nujol}$: 3400, 3230, 1780, 1670, 1622, 1590, 1550, 1050 cm$^{-1}$.

(30) 7-[2-(6-Aminopyridin-2-yl)-2-methoxyiminoacetamido]-3-(5-aminomethyl-1,3,4-thiadiazol-2-yl)thiomethyl-3-cephem-4-carboxylic acid (syn isomer).

I.R. $\nu_{max}^{Nujol}$: 3500, 3400, 3230, 1770, 1670, 1620, 1040 cm$^{-1}$.

(31) 7-[2-(6-Aminopyridin-2-yl)-2-methoxyiminoacetamido]-3-(1-carboxymethyl-1H-tetrazol-5-yl)thiomethyl-3-cephem-4-carboxylic acid (syn isomer).

I.R. $\nu_{max}^{Nujol}$: 3380, 3220, 1780, 1670, 1620, 1050 cm$^{-1}$.

(32) 7-[2-(6-Aminopyridin-2-yl)acetamido]-3-(1-methyl-1H-tetrazol-5-yl)thiomethyl-3-cephem-4-carboxylic acid (syn isomer).

I.R. $\nu_{max}^{Nujol}$: 3600-3080, 1763, 1698, 1663 cm$^{-1}$.

(33) 7-[2-(6-Aminopyridin-2-yl)-2-methoxyiminoacetamido]-3-chloro-3-cephem-4-carboxylic acid hydrochloride (syn isomer).

I.R. $\nu_{max}^{Nujol}$: 3300-3100, 1780, 1710, 1660, 1610, 1540, 1370 cm$^{-1}$.

(34) 7-[2-(6-Aminopyridin-2-yl)-2-methoxyiminoacetamido]-3-methoxy-3-cephem-4-carboxylic acid.

I.R. $\nu_{max}^{Nujol}$: 3300, 1775, 1700-1650, 1045 cm$^{-1}$.

(35) 7-[2-(6-Aminopyridin-2-yl)-2-methoxyiminoacetamido]-7-methoxy-3-(1-methyl-1H-tetrazol-5-yl)-thiomethyl-3-cephem-4-carboxylic acid (syn isomer).

I.R. $\nu_{max}^{Nujol}$: 3300, 1780, 1700, 1680 cm$^{-1}$.

(36) 7-[2-(6-Aminopyridin-2-yl)-2-methoxyiminoacetamido]-2-methyl-3-cephem-4-carboxylic acid (syn isomer).

I.R. $\nu_{max}^{Nujol}$: 3400–3100, 1780, 1730, 1665, 1550, 1295, 1258, 1050 cm$^{-1}$.

(37) 7-[2-(6-Aminopyridin-2-yl)-2-methoxyiminoacetamido]-3-methyl-3-cephem-4-carboxylic acid hydrochloride (syn isomer).

I.R. $\nu_{max}^{Nujol}$: 3100, 1780, 1682, 1668, 1260, 1050 cm$^{-1}$.

(38) 7-[2-(6-Aminopyridin-2-yl)-2-hydroxyiminoacetamido]-3-(1-methyl-1H-tetrazol-5-yl)thiomethyl-3-cephem-4-carboxylic acid (syn isomer).

I.R. $\nu_{max}^{Nujol}$: 3300, 1760, 1680 cm$^{-1}$.

(39) 7-[2-(6-Aminopyridin-2-yl)-2-methoxyiminoacetamido]-3-carbamoyloxymethyl-3-cephem-4-carboxylic acid (syn isomer).

I.R. $\nu_{max}^{Nujol}$: 3400, 1780, 1720, 1670 cm$^{-1}$.

(40) 7-[2-(2-Aminopyrimidin-4-yl)-2-methoxyiminoacetamido]-3-(1-methyl-1H-tetrazol-5-yl)thiomethyl-3-cephem-4-carboxylic acid.

I.R. $\nu_{max}^{Nujol}$: 3440, 3320, 1790, 1693, 1660, 1630, 1525, 1043 cm$^{-1}$.

(41) 7-[2-(6-Aminopyridin-2-yl)-2-ethoxyiminoacetamido]-3-(1-methyl-1H-tetrazol-5-yl)thiomethyl-3-cephem-4-carboxylic acid (syn isomer).

I.R. $\nu_{max}^{Nujol}$: 3380, 3240, 1780, 1670 cm$^{-1}$.

(42) 7-[2-(6-Aminopyridin-2-yl)-2-methoxyiminoacetamido]cephalosporanic acid (syn isomer).

I.R. $\nu_{max}^{Nujol}$: 3350–3220, 1780, 1740, 1680–1655, 1380, 1040 cm$^{-1}$.

EXAMPLE 10

Conc. hydrochloric acid (0.36 ml) was added to a solution of 7-[2-(4-formamidopyrimidin-2-yl)-2-methoxyiminoacetamido]-3-(1-methyl-1H-tetrazol-5-ylthiomethyl)-3-cephem-4-carboxylic acid (1.9 g) in methanol (38 ml), and the mixture was stirred at ambient temperature for 5.5 hours. The reaction mixture was concentrated, and the concentrate was diluted with water and then washed with ethyl acetate. After the ethyl acetate in the aqueous solution was removed by distillation, the aqueous solution was subjected to column chromatography on a macroporous, non-ionic adsorption resin, "Diaion HP-20" (Trade mark, manufactured by Mitsubishi Chemical Industries Ltd.) (110 ml). Elution was carried out with water (400 ml), 10% aqueous methanol (100 ml.), 20% aqueous methanol (200 ml.) and then 30% aqueous methanol (2 l.), and the fractions containing the desired compound were collected. The combined fractions were evaporated to dryness under reduced pressure to give powders (1.0 g.) of 7-[2-(4-aminopyrimidin-2-yl)-2-methoxyiminoacetamido]-3-(1-methyl-1H-tetrazol-5-ylthiomethyl)-3-cephem-4-carboxylic acid (a mixture of syn and anti isomer), mp. 150°–160° C. (dec.).

I.R. $\nu_{max}^{Nujol}$: 3380, 3220, 1780, 1620–1700, 1240, 1040 cm$^{-1}$.

| N.M.R. δppm (DMSO-d$_6$) : | 3.72 (2H, broad s), |
| --- | --- |
| | 3.98 (6H, s) |
| | 4.34 (2H, broad s) |
| | 5.08 (d, J = 4H) |
| | 5.15 (d, J = 4Hz) ⎫ (1H) |
| | 5.60–6.00 (1H, m) |
| | 6.45 |
| | (1H, d, J = 6Hz) |
| | 7.00 (2H, m) |
| | 8.12 |
| | (1H, d, J = 6Hz) |
| | 8.87 (d, J = 8Hz) ⎫ (1H) |
| | 9.43 (d, J = 8Hz) ⎭ |

EXAMPLE 11

Conc. hydrochloric acid (0.31 ml.) was added to a solution of 7-[2-allyloxyimino-2-(6-formamidopyridin-2-yl)acetamido]-3-(1-methyl-1H-tetrazol-5-ylthiomethyl)-3-cephem-4-carboxylic acid (syn isomer) (1.75 g.) in methanol (7 ml.), and the mixture was stirred at ambient temperature for 30 minutes. The methanol was removed by distillation from the reaction mixture, and the remaining aqueous solution was diluted with water (80 ml.) and then adjusted to pH 2–3 with an aqueous solution of sodium bicarbonate. The aqueous solution was subjected to column chromatography on a macroporous, non-ionic adsorption resin "Diaion HP-20" (Trade Mark, manufactured by Mitsubishi Chemical Industries Ltd.) (50 ml.). After the column was washed with water (1 l.), elution was carried out with 50% aqueous methanol (1 l.) and fractions containing the desired compound were collected. The methanol was removed by distillation from the combined fractions under reduced pressure and the resultant aqueous solution was lyophilized to give 7-[2-allyloxyimino-2-(6-aminopyridin-2-yl)acetamido]-3-(1-methyl-1H-tetrazol-5-ylthiomethyl)-3-cephem-4-carboxylic acid (syn isomer) (1.13 g.), mp. 149°–151° C. (dec.).

I.R. $\nu_{max}^{Nujol}$: 3380, 3310, 1780, 1670, 1620 cm$^{-1}$.

N.M.R. δppm (DMSO-d$_6$): 3.70 (2H, broad s), 3.93 (3H, s), 4.33 (2H, broad s), 4.67 (2H, d, J=5 Hz), 5.17–5.57 (2H, m), 5.10 (1H, d, J=5 Hz), 5.80 (1H, d,d, J=5 Hz, 9 Hz), 5.83–6.27 (1H, m), 6.50 (1H, d, J=8 Hz), 6.90 (1H, d, J=8 Hz), 7.43 (1H, t, J=8 Hz), 9.47 (1H, d, J=9 Hz).

EXAMPLE 12

Conc. Hydrochloric acid (0.43 ml.) was added to a solution of 7-[2-(6-formamidopyridin-2-yl)-2-propargyloxyiminoacetamido]-3-(1-methyl-1H-tetrazol-5-ylthiomethyl)-3-cephem-4-carboxylic acid (syn isomer) (2.35 g.) in methanol (15 ml.), and the mixture was stirred at ambient temperature for 30 minutes. The methanol was removed by distillation under reduced pressure from the reaction mixture, and the remaining aqueous solution was diluted with water (100 ml.) and then adjusted to pH 2 with an aqueous solution of sodium bicarbonate. The precipitating crystals were collected by filtration, washed with water and then dried to give 7-[2-(6-aminopyridin-2-yl)-2-proparglyoxyiminoacetamido]-3-(1-methyl-1H-tetrazol-5-ylthiomethyl)-3-cephem-4-carboxylic acid (syn isomer) (1.05 g.), mp. 163°–165° C. (dec.).

I.R. $\nu_{max}^{Nujol}$: 3270, 1765, 1690, 1665, 1620, 1580, 1530 cm$^{-1}$.

N.M.R. δppm (DMSO-d$_6$): 3.48 (1H, t, J=2 Hz), 3.62, 3.76 (2H, AB$_q$, J=18 Hz), 3.90 (3H, s), 4.26, 4.34 (2H, AB$_q$, J=13 Hz), 4.76 (2H, d, J=2 Hz), 5.12 (1H, d, J=5 Hz), 5.80 (1H, d,d, J=5 Hz, 9 Hz), 6.52 (1H, d, J=8 Hz), 6.88 (1H, d, J=8 Hz), 7.42 (1H, t, J=8 Hz), 9.54 (1H, d, J=9 Hz).

EXAMPLE 13-(1)

Conc. hydrochloric acid (242 mg.) was added to a solution of 7-[2-(6-chloro-2-formamidopyrimidin-4-yl)-2-methoxyiminoacetamido]-3-(1-methyl-1H-tetrazol-5-ylthimethyl)-3-cephem-4-carboxylic acid (1.2 g.) in methanol (12 ml.), and the mixture was stirred at ambient temperature for 5 hours. The reaction mixture was evaporated to dryness under reduced pressure to give a foamy residue, which was pulverized with ethyl ether. This powder (1.1 g.) was dissolved in methanol (6 ml.), and to ethyl ether (50 ml.) was added dropwise the methanol solution. The precipitates were collected by filtration and then dried to give 7-[2-(2-amino-6-chloropyrimidin-4-yl)-2-methoxyiminoacetamido]-3-(1-methyl-1H-tetrazol-5-ylthiomethyl)-3-cephem-4-carboxylic acid hydrochloride (0.95 g.).

I.R. $\nu_{max}^{Nujol}$: 3100–3300, 1785, 1660, 1390, 1050 cm$^{-1}$.

N.M.R. δppm (DMSO-d$_6$): 3.75 (2H, m), 3.95 (3H, s), 4.00 (3H, s), 4.24, 4.40 (2H, AB$_q$, J=14 Hz), 5.18 (1H, d, J=4.5 Hz), 5.79 (1H, d,d, J=4.5 Hz, 8.0 Hz), 6.28 (1H, s), 8.00–10.00 (2H, broad s), 9.96 (1H, d, J=8 Hz).

The following compounds were obtained according to similar manners to those of Examples 10 and 13-(1).

(2) 7-[2-(4-Aminopyridin-2-yl)-2-methoxyiminoacetamido]-3-methyl-1H-tetrazol-5-ylthiomethyl)-3-cephem-4-carboxylic acid (syn isomer), mp. 163°–167° C. (dec.).

I.R. $\nu_{max}^{Nujol}$: 3400, 3230, 1778, 1650, 1600, 1380, 1050 cm$^{-1}$.

N.M.R. δppm (DMSO-d$_6$ and D$_2$O): 3.64 (2H, m), 3.97 (6H, s), 4.32 (2H, broad s), 5.12 (1H, d, J=4.5 Hz), 5.80 (1H, d,d, J=4.5 Hz, 8 Hz), 6.60 (1H, d,d, J=2 Hz, 7 Hz), 6.97 (1H, d, J=2 Hz), 8.00 (1H, d, J=7 Hz), 9.52 (1H, d, J=8 Hz).

(3) 7-[2-(6-Aminopyridin-2-yl)-2-propoxyiminoacetamido]-3-(1-methyl-1H-tetrazol-5-ylthiomethyl)-3-cephem-4-carboxylic acid (syn isomer), mp. 138°–140° C. (dec.).

I.R. $\nu_{max}^{Nujol}$: 3400, 3250, 1780, 1670, 1625, 1590, 1550 cm$^{-1}$.

N.M.R. δppm (DMSO-d$_6$): 0.9 (3H, t, J=8 Hz), 1.67 (2H, m), 3.7 (2H, broad s), 3.93 (3H, s), 4.07 (2H, t, J=8 Hz), 4.30 (2H, broad s), 5.13 (1H, d, J=5 Hz), 5.83 (1H, d,d, J=5 Hz, 9 Hz), 6.50 (1H, d, J=8 Hz), 6.90 (1H, d, J=8 Hz), 7.47 (1H, t, J=8 Hz), 9.30 (1H, d, J=9 Hz).

(4) 7-[2-(6-Aminopyridin-2-yl)-2-isopropoxyiminoacetamido]-3-(1-methyl-1H-tetrazol-5-ylthiomethyl)-3-cephem-4-carboxylic acid (syn isomer), mp. 149°–151° C. (dec.).

I.R. $\nu_{max}^{Nujol}$: 3380, 3240, 1780, 1670, 1620 cm$^{-1}$.

N.M.R. δppm (DMSO-d$_6$): 1.27 (6H, d, J=6 Hz), 3.70 (2H, broad s), 3.97 (3H, s), 4.33 (2H, broad s), 4.35 (1H, m), 5.17 (1H, d, J=5 Hz), 5.87 (1H, d,d, J=5 Hz, 9 Hz), 6.50 (1H, d, J=8 Hz), 6.93 (1H, d, J=8 Hz), 7.47 (1H, t, J=8 Hz), 9.43 (1H, d, J=9 Hz).

(5) 7-[2-(6-Aminopyridin-2-yl)-2-isobutoxyiminoacetamido]-3-(1-methyl-1H-tetrazol-5-ylthiomethyl)-3-cephem-4-carboxylic acid (syn isomer), mp. 140°–142° C. (dec.).

I.R. $\nu_{max}^{Nujol}$: 3370, 3220, 1780, 1670, 1620 cm$^{-1}$.

N.M.R. δppm (DMSO-d$_6$): 0.88 (6H, d, J=7 Hz), 1.96 (1H, m), 3.68 (2H, broad s), 3.88 (2H, d, J=7 Hz), 3.92 (3H, s), 4.24, 4.36 (2H, AB$_q$, J=13 Hz), 5.12 (1H, d, J=5 Hz), 5.84 (1H, d,d, J=5 Hz, 9 Hz), 6.48 (1H, d, J=8 Hz), 6.88 (1H, d, J=8 Hz), 7.40 (1H, t, J=8 Hz), 9.44 (1H, d, J=9 Hz)

(6) 7-[2-(2-Aminopyridin-4-yl)-2-methoxyiminoacetamido]-3-(1-methyl-1H-tetrazol-5-ylthiomethyl)-3-cephem-4-carboxylic acid (syn isomer), mp. 175°–177° C. (dec.).

I.R. $\nu_{max}^{Nujol}$: 3200, 1775, 1670, 1600, 1560 cm$^{-1}$.

N.M.R. δppm (DMSO-d$_6$): 3.73 (2H, broad s), 3.98 (6H, s), 4.35 (2H, broad s), 5.18 (1H, d, J=5 Hz), 5.83 (1H, d,d, J=5 Hz, 8 Hz), 6.67–6.80 (2H, m), 8.00 (1H, d, J=6 Hz), 9.79 (1H, d, J=8 Hz).

(7) 7-[2-(6-Aminopyridin-2-yl)-2-ethoxyiminoacetamido]-2-methyl-3-cephem-4-carboxylic acid (syn isomer), mp. 190°–195° C. (dec.).

I.R. $\nu_{max}^{Nujol}$: 3350, 3150, 1795, 1730, 1670 cm$^{-1}$.

N.M.R. δppm (DMSO-d$_6$): 1.33 (3H, t, J=7 Hz), 1.43 (3H, d, J=7 Hz), 3.90 (1H, m), 4.35 (2H, q, J=7 Hz), 5.17 (1H, d, J=4 Hz), 5.92 (1H, d,d, J=4 Hz, 8 Hz), 6.58 (1H, d, J=6 Hz), 6.73 (1H, d, J=7 Hz), 7.17 (1H, d, J=8 Hz), 7.95 (1H, d,d, J=7 Hz, 8 Hz), 9.93 (1H, d, J=8 Hz).

(8) 7-[2-(6-Aminopyridin-2-yl)-2-propoxyiminoacetamido]-2-methyl-3-cephem-4-carboxylic acid (syn isomer), mp. 190°–195° C. (dec.).

I.R. $\nu_{max}^{Nujol}$: 3340, 3150, 1780, 1735, 1670 cm$^{-1}$.

N.M.R. δppm (DMSO-d$_6$): 0.85 (3H, t, J=8 Hz), 1.40 (3H, d, J=7 Hz), 1.70 (2H, m), 3.80 (1H, m), 4.15 (2H, t, J=6 Hz), 5.10 (1H, d, J=4 Hz), 5.90 (1H, d,d, J=4 Hz, 8 Hz), 6.54 (1H, d, J=6 Hz), 6.74 (1H, d, J=7 Hz), 6.85 (1H, d, J=7 Hz), 7.68 (1H, t, J=7 Hz), 9.68 (1H, d, J=8 Hz).

(9) 7-[2-(6-Aminopyridin-2-yl)-2-isopropoxyiminoacetamido]-2-methyl-3-cephem-4-carboxylic acid (syn isomer), mp. 185°–188° C. (dec.).

I.R. $\nu_{max}^{Nujol}$: 3350, 3150, 1795, 1735, 1670 cm$^{-1}$.

N.M.R. δppm (DMSO-d$_6$): 1.37 (6H, d, J=6 Hz), 1.47 (3H, d, J=6 Hz), 3.92 (1H, m), 4.58 (1H, m), 5.20 (1H, d, J=4 Hz), 5.93 (1H, d,d, J=4 Hz, 8 Hz), 6.60 (1H, d, J=6 Hz), 6.77 (1H, d, J=7 Hz), 7.08 (1H, d, J=8 Hz), 7.90 (1H, d,d, J=7 Hz, 8 Hz), 9.87 (1H, d, J=8 Hz)

(10) 7-[2-(6-Aminopyridin-2-yl)-2-butoxyiminoacetamido]-3-(1-methyl-1H-tetrazol-5-ylthiomethyl)-3-cephem-4-carboxylic acid (syn isomer), mp. 108°–110° C. (dec.).

I.R. $\nu_{max}^{Nujol}$: 3350, 3200, 1775, 1670, 1620, 1585, 1540 cm$^{-1}$.

N.M.R. δppm (DMSO-d$_6$): 0.90 (3H, t, J=7 Hz), 1.80–1.16 (4H, m), 3.70 (2H, broad s), 3.92 (3H, s), 4.16 (2H, t, J=7 Hz), 4.30 (2H, broad s), 5.14 (1H, d, J=5 Hz), 5.78 (1H, d,d, J=5 Hz, 9 Hz), 6.58 (1H, d, J=8 Hz), 6.86 (1H, d, J=8 Hz), 7.48 (1H, t, J=8 Hz), 9.50 (1H, d, J=9 Hz)

(11) 7-[2-(6-Aminopyridin-2-yl)-2-butoxyiminoacetamido]-2-methyl-3-cephem-4-carboxylic acid (syn isomer), mp. 200°–205° C. (dec.).

I.R. $\nu_{max}^{Nujol}$: 3400, 3120, 1785, 1660 cm$^{-1}$.

N.M.R. δppm (DMSO-d$_6$): 0.90 (3H, t, J=7 Hz), 1.45 (3H, d, J=6 Hz), 1.20–1.80 (4H, m), 3.85 (1H, m), 4.25 (2H, t, J=6 Hz), 5.12 (1H, d, J=5 Hz), 5.90 (1H, d,d, J=5 Hz, 8 Hz), 6.56 (1H, d, J=5 Hz), 6.70 (1H, d, J=7 Hz), 7.05 (1H, d, J=7 Hz), 7.82 (1H, t, J=7 Hz), 9.80 (1H, d, J=8 Hz).

(12) 7-[2-(6-Aminopyridin-2-yl)-2-isobutoxyiminoacetamido]-2-methyl-3-cephem-4-carboxylic acid (syn isomer), mp. 175°–180° C. (dec.).

I.R. $\nu_{max}^{Nujol}$: 3300, 1785, 1735, 1660 cm$^{-1}$.

N.M.R. δppm (DMSO-d$_6$): 0.95 (6H, d, J=6 Hz), 1.48 (3H, d, J=7 Hz), 2.08 (1H, m), 3.92 (1H, m), 4.08 (2H, d, J=7 Hz), 5.20 (1H, d, J=4 Hz), 5.95 (1H, d,d, J=4 Hz, 8 Hz), 6.62 (1H, d, J=6 Hz), 6.80 (1H, d, J=7 Hz), 7.07 (1H, d, J=8 Hz), 7.88 (1H, d,d, J=7 Hz, 8 Hz), 9.87 (1H, d, J=8 Hz).

(13) 7-[2-Allyloxyimino-2-(6-aminopyridin-2-yl)acetamido]-2-methyl-3-cephem-4-carboxylic acid (syn isomer), mp. 168°–173° C. (dec.).

I.R. $\nu_{max}^{Nujol}$: 3350, 3150, 1795, 1735, 1670 cm$^{-1}$.

N.M.R. δ ppm (DMSO-d$_6$): 1.47 (3H, d, J=7 Hz), 3.90 (1H, m), 4.83 (2H, d, J=5 Hz), 5.20 (1H, d, J=4 Hz), 5.23–5.66 (2H, m), 5.95 (1H, d,d, J=4 Hz, 8 Hz), 5.83–6.30 (1H, m), 6.60 (1H, d, J=6 Hz), 6.77 (1H, d, J=7 Hz), 7.10 (1H, d, J=7 Hz), 7.93 (1H, t, J=7 Hz), 9.93 (1H, d, J=8 Hz).

(14) 7-[2-(6-Aminopyridin-2-yl)-2-propargyloxyiminoacetamido]-2-methyl-3-cephem-4-carboxylic acid (syn isomer), mp. 165°–170° C. (dec.).

I.R. $\nu_{max}^{Nujol}$: 3350, 1780, 1670 cm$^{-1}$.

N.M.R. δ ppm (DMSO-d$_6$): 1.47 (3H, d, J=7 Hz), 3.58 (2H, t, J=2 Hz), 3.87 (1H, m), 4.88 (1H, d, J=2 Hz), 5.17 (1H, d, J=4 Hz), 5.93 (1H, d,d, J=4 Hz, 8 Hz), 6.58 (1H, d, J=6 Hz), 6.66 (1H, d, J=8 Hz), 6.70 (1H, d, J=8 Hz), 7.68 (1H, t, J=8 Hz), 9.77 (1H, d, J=8 Hz).

(15) 7-[2-(6-Aminopyridin-2-yl)-2-(2,2,2-trifluoroethoxyimino)acetamido]-3-(1-methyl-1H-tetrazol-5-ylthiomethyl)-3-cephem-4-carboxylic acid (syn isomer), mp. 165°–170° C. (dec.).

I.R. $\nu_{max}^{Nujol}$: 3400, 1780, 1690 cm$^{-1}$.

N.M.R. δ ppm (DMSO-d$_6$): 3.72 (2H, broad s), 3.95 (3H, s), 4.32 (2H, broad s), 4.66, 4.92 (2H, AB$_q$, J=9 Hz), 5.17 (1H, d, J=4 Hz), 5.83 (1H, d,d, J=4 Hz, 8 Hz), 6.32 (1H, d, J=8 Hz), 6.90 (1H, d, J=8 Hz), 7.55 (1H, t, J=8 Hz), 9.68 (1H, d, J=8 Hz).

(16) 7-[2-(6-Aminopyridin-2-yl)-2-phenoxyiminoacetamido]-2-methyl-3-cephem-4-carboxylic acid (syn isomer), mp. 145°–147° C. (dec.).

I.R. $\nu_{max}^{Nujol}$: 3200, 1760, 1690, 1670 cm$^{-1}$.

N.M.R. δ ppm (DMSO-d$_6$): 1.50 (3H, d, J=7 Hz), 3.90 (1H, m), 5.23 (1H, d, J=4 Hz), 6.05 (1H, d,d, J=4 Hz, 8 Hz), 6.60 (1H, d, J=6 Hz), 6.73 (1H, d, J=7.5 Hz), 7.13 (1H, d, J=7.5 Hz), 7.00–7.50 (5H, m), 7.63 (1H, d, J=7.5 Hz), 9.88 (1H, d, J=8 Hz).

(17) 7-[2-(6-Aminopyridin-3-yl)-2-methoxyiminoacetamido]-3-(1-methyl-1H-tetrazol-5-ylthiomethyl)-3-cephem-4-carboxylic acid (syn isomer), mp. 165°–167° C. (dec.).

I.R. $\nu_{max}^{Nujol}$: 3380, 3220, 1780, 1680, 1630, 1590, 1550 cm$^{-1}$.

N.M.R. δ ppm (DMSO-d$_6$): 3.75 (2H, broad s), 3.90 (3H, s), 3.97 (3H, s), 4.35 (2H, broad s), 5.17 (1H, d, J=5 Hz), 5.82 (1H, d,d, J=5 Hz, 8 Hz), 6.57 (1H, d, J=9 Hz), 7.67 (1H, d,d, J=2 Hz, 9 Hz), 8.03 (1H, d, J=2 Hz), 9.73 (1H, d, J=8 Hz).

(18) 7-[2-(6-Aminopyridin-3-yl)-2-methoxyiminoacetamido]-3-(1-methyl-1H-tetrazol-5-ylthiomethyl)-3-cephem-4-carboxylic acid (anti isomer), mp 153°–155° C. (dec.).

I.R. $\nu_{max}^{Nujol}$: 3350, 3200, 1780, 1680, 1630, 1520 cm$^{-1}$.

N.M.R. δ ppm (DMSO-d$_6$): 3.73 (2H, broad s), 3.97 (6H, s), 4.35 (2H, broad s), 5.17 (1H, d, J=5 Hz), 5.72 (1H, d,d, J=5 Hz, 8 Hz), 6.62 (1H, d, J=9 Hz), 7.75 (1H, d,d, J=2 Hz, 9 Hz), 8.25 (1H, d, J=2 Hz), 9.25 (1H, d, J=8 Hz).

(19) 7-[2-(6-Amino-3-chloropyridin-2-yl)-2-methoxyiminoacetamido]-3-(1-methyl-1H-tetrazol-5-ylthiomethyl)-3-cephem-4-carboxylic acid hydrochloride (syn isomer), mp. 155°–160° C. (dec.).

I.R. $\nu_{max}^{Nujol}$: 3100-3350, 1790, 1670, 1550, 1380, 1235, 1040 cm$^{-1}$.

N.M.R. δ ppm (DMSO-d$_6$): 3.70 (2H, m), 3.94 (3H, s), 4.03 (3H, s), 4.21, 4.37 (2H, AB$_q$, J=14 Hz), 5.14 (1H, d, J=4.5 Hz), 5.80 (1H, d,d, J=4.5 Hz, 8 Hz), 6.97 (1H, d, J=10 Hz), 7.80 (1H, d, J=10 Hz), 7.50–9.00 (2H, m), 9.70 (1H, d, J=8 Hz).

(20) 7-[2-(6-Amino-3,5-dichloropyridin-2-yl)-2-methoxyiminoacetamido]-3-(1-methyl-1H-tetrazol-5-ylthiomethyl)-3-cephem-4-carboxylic acid (syn isomer), mp. 139°–144° C. (dec.).

I.R. $\nu_{max}^{Nujol}$: 3300, 1785, 1730, 1660, 1545, 1380, 1235, 1045 cm$^{-1}$.

N.M.R. δ ppm (DMSO-d$_6$): 3.73 (2H, m), 3.98 (6H, s), 4.35 (2H, broad s), 5.17 (1H, d, J=4.5 Hz), 5.81 (1H, d,d, J=4.5 Hz, 8 Hz), 7.87 (1H, s), 7.50–8.20 (2H, m), 9.43 (1H, d, J=8 Hz).

(21) 7-[2-(4-Aminopyrimidin-2-yl)-2-methoxyiminoacetamido]-3-(1,3,4-thiadiazol-2-ylthiomethyl)-3-cephem-4-carboxylic acid (syn isomer), mp 164°–171° C. (dec.).

(22) 7-[2-(4-Aminopyrimidin-2-yl)-2-methoxyiminoacetamido]-3-(5-methyl-1,3,4-thiadiazol-2-ylthiomethyl)-3-cephem-4-carboxylic acid (syn isomer), mp 161°–167° C. (dec.).

(23) 7-[2-(4-Aminopyridin-2-yl)-2-methoxyiminoacetamido]-cephalosporanic acid (syn isomer), mp 149°–159° C. (dec.).

EXAMPLE 14

(1) A mixture of N,N-dimethyl formamide (12 ml) and phosphoryl chloride (1.84 g) was stirred for 30 minutes at ambient temperature. To the mixture were added methylene chloride (12 ml) and 2-ethoxyimino-2-(4-formamidopyrimidin-2-yl)acetic acid (syn isomer) (1.91 g) at −5° to 0° C., and then the reaction mixture was stirred for an hour at the same temperature.

On the other hand, a mixture of 7-amino-3-(1,3,4-thiadiazol-2-ylthiomethyl)-3-cephem-4-carboxylic acid (4.36 g) and trimethylsilyl acetamide (12 g) in methylene chloride (120 ml) was warmed to make a clear solution. The solution was cooled to −10° C. and added to the activated acid solution obtained above. The reaction mixture was stirred for 40 minutes at 0° C., and then poured into a cold aqueous solution of sodium bicarbonate. The aqueous layer was separated out, adjusted to pH 2 with 10% hydrochloric acid and extracted with ethyl acetate. The extract was dried over anhydrous magnesium sulfate and evaporated to dryness. The residue was triturated with diethyl ether to give an amorphous precipitate (3.6 g) of 7-[2-ethoxyimino-2-(4-formamidopyrimidin-2-yl)acetamido]-3-(1,3,4-thiadiazol-2-ylthiomethyl)-3-cephem-4-carboxylic acid (syn isomer).

I.R. $\nu_{max}^{Nujol}$: 3250, 1780, 1660, 1570 cm$^{-1}$.

N.M.R. δppm (DMSO-d$_6$): 1.30 (3H,t,J=7 Hz), 3.72 (2H, board s), 4.27 (2H,q,J=7 Hz), 4.30, 4.57 (2H,AB$_q$,J=13 Hz), 5.18 (1H,d,J=5 Hz), 5.88 (1H, dd, J=5 Hz, 8 Hz), 7.1–7.5 (1H,m), 8.67 (1H,d,J=6 Hz), 8.9–9.2 (1H,m), 9.45 (1H,d,J=8 Hz), 9.52 (1H,s), 11.10 (1H,d,J=7 Hz).

The following compounds were obtained according to the similar manner to that of Example 14-(1).

(2) 7-[2-(4-Formamidopyrimidin-2-yl)-2-propoxyiminoacetamido]-3-(1,3,4-thiadiazol-2-ylthiomethyl)-3-cephem-4-carboxylic acid (syn isomer), mp 170°–175° C. (dec.).

I.R.$\nu_{max}^{Nujol}$: 3250, 3100, 1780, 1710, 1670, 1615, 1580 cm$^{-1}$.

N.M.R. δppm (DMSO-d$_6$): 0.93 (3H,t,J=7 Hz), 1.4-1.9 (2H,m), 3.72 (2H,broad s), 4.20 (2H,t,J=7 Hz), 4.33, 4.58 (2H, ABq, J=13 Hz), 5.20 (1H,d,J=6 Hz), 5.92 (1H, d,d,J=5 Hz,8 Hz), 7.0-7.7 (1H,m), 8.67 (1H,d,J=6 Hz), 8.8-9.2 (1H,m), 9.47 (1H,d,J=8 Hz), 9.53 (1H,s), 11.23 (1H,d,J=6 Hz).

(3) 7-[2-Allyloxyimino-2-(4-formamidopyrimidin-2-yl)acetamido]-3-(1,3,4-thiadiazol-2-ylthiomethyl)-3-cephem-4-carboxylic acid (syn isomer), mp 130°-133° C. (dec.).

I.R.$\nu_{max}^{Nujol}$: 3250, 1780, 1720, 1660, 1570 cm$^{-1}$.

N.M.R. δppm (DMSO-d$_6$): 3.73 (2H,broad s), 4.80 (2H,d,J=5 Hz), 5.20 (1H,d, J=5 Hz), 5.1-5.6 (2H, m), 5.90 (1H,d,d,J=5 Hz, 8 Hz), 5.7-6.3 (1H, m), 7.0-8.7 (1H,m), 8.68 (1H,d, J=6 Hz), 8.8-9.3 (1H,m), 9.53 (1H, d,J=8 Hz), 9.57 (1H,s), 11.23 (1H, d, J=6 Hz).

(4) 7-[2-Benzyloxyimino-2-(4-formamidopyrimidin-2-yl)acetamido]-3-(1,3,4-thiadiazol-2-ylthiomethyl)-3-cephem-4-carboxylic acid (syn isomer), mp 143°-145° C. (dec.).

I.R.$\nu_{max}^{Nujol}$: 3300, 1785, 1720, 1670, 1575 cm$^{-1}$.

N.M.R. δppm (DMSO-d$_6$): 3.63 (2H, broad s), 4.28, 4.52 (2H,ABq,J=13 Hz), 5.13 (1H,d,J=5 Hz), 5.27 (2H,s), 5.85(1H,d,d,J=5 Hz,8 Hz), 7.32 (5H,s), 7.2-7.6 (1H,m), 8.60 (1H,d,J=6 Hz), 8.8-9.2 (1H,m), 9.52 (1H,s), 9.55 (1H,d,J=8 Hz), 11.30 (1H,d,J=6 Hz).

(5) 7-[2-(6-Formamidopyridin-2-yl)-2-methoxyiminoacetamido]-3-(1-allyl-1H-tetrazol-5-yl)thiomethyl]-3-cephem-4-carboxylic acid (syn isomer).

I.R.$\nu_{max}^{Nujol}$: 3300, 1785, 1700-1670, 1580, 1380, 1260, 815 cm$^{-1}$.

N.M.R. δppm (DMSO-d$_6$): 3.72 (2H, broad s), 3.95 (3H,s), 4.20, 4.50 (2H, ABq, J=13 Hz), 4.9-6.6(7H,m), 6.85-9.42(5H,m), 10.5(1H,m).

(6) 7-[2-(2,2,2-Trifluoroethoxyimino)-2-(6-formamidopyridin-2-yl)acetamido]cephalosporanic acid (syn isomer), which starts to decompose at 120° C.

I.R.$\nu_{max}^{Nujol}$: 3310, 1788, 1718, 1673 cm$^{-1}$.

N.M.R. δppm (DMSO-d$_6$): 2.00 (3H,s), 3.53 (2H, broad s), 4.5-5.0 (4H,m), 5.15 (1H,d,J=5 Hz), 5.88 (1H,d,d, J=5 Hz, 8 Hz), 6.7-8.1 (3H,m), 9.27 (1H,broad d, J=10 Hz), 9.62 (1H,d,J=8 Hz), 10.40-10.85 (1H, m).

(7) 7-[2-Allyloxyimino-2-(6-formamidopyridin-2-yl) acetamido]-3-(5-tert-butoxycarbonylaminomethyl-1,3,4-thiadiazol-2-ylthiomethyl)-3-cephem-4-carboxylic acid (syn isomer), mp. 170°-180° C. (dec.)

I.R.$\nu_{max}^{Nujol}$: 3300, 1788, 1720-1680 cm$^{-1}$.

N.M.R. δppm (DMSO-d$_6$): 1.43 (9H,s), 3.72 (2H, broad s), 4.1-4.9 (6H,m), 5.1-6.3 (5H,m), 6.75-8.1 (3H,m), 9.1-9.5 (1H,m), 9.58 (1H,d,J=8 Hz), 10.4-10.8 (1H,m).

(8) 7-[2-(6-Formamidopyridin-2-yl)-2-propargyloxyiminoacetamido]-3-(1,3,4-thiadiazol-2-ylthiomethyl)-3-cephem-4-carboxylic acid (syn isomer), mp 152°-156° C. (dec.).

I.R.$\nu_{max}^{Nujol}$: 3300, 1780, 1670, 1580 cm$^{-1}$.

N.M.R. δppm (DMSO-d$_6$): 3.5 (1H,m), 3.7 (2H,m), 4.25, 4.62 (2H,ABq,J=13 Hz), 4.8 (2H,m), 5.17(1H,d,J=4.5 Hz), 6.22 (1H,d,d,J=4.5 Hz,8 Hz), 7.0-9.4 (2H,m), 7.5 (1H,d,J=7 Hz), 7.85 (1H,t,J=7 Hz), 9.57(1H,s), 9.4-9.5 (1H,m), 10.6 (1H,m).

(9) 7-[2-(4-Formamidopyrimidin-2-yl)-2-methoxyimino acetamido]-3-(tetrazolo[1,5-b]pyridazin-6-ylthiomethyl)-3-cephem-4-carboxylic acid (syn isomer).

I.R.$\nu_{max}^{Nujol}$: 3250, 1780, 1710, 1680, 1570 cm$^{-1}$.

(10) 7-[2-(4-Formamidopyrimidin-2-yl)-2-methoxyimino acetamido]cephalosporanic acid (syn isomer), mp 150°-154° C. (dec.).

I.R.$\nu_{max}^{Nujol}$: 3250, 1780, 1700, 1670, 1590 cm$^{-1}$.

N.M.R.δppm (DMSO-d$_6$): 2.05 (3H,s), 3.58 (2H, broad s), 4.00 (3H,s), 4.73, 5.00 (2H,ABq,J=13 Hz), 5.20 (1H,d,J=4 Hz), 5.90 (1H,d,d,J=4 Hz,8 Hz), 7.40 (1H, broad s), 8.68 (1H,d,J=5 Hz), 9.07 (1H,broad s), 9.53 (1H,d,J=8 Hz), 11.23 (1H,d,J=8 Hz). (11) A mixture of N,N-dimethylformamide (14 ml) and phosphoryl chloride (2.5 g) was stirred for 30 minutes at 40° C. To the mixture were added methylene chloride (14 ml) and 2-(2,2-dichloroacetoxyimino)-2-(6-formamidopyridin-2-yl)acetic acid (syn isomer) (5.3 g) at −20° C., and then the reaction mixture was stirred for 30 minutes at −15° to −10° C.

On the other hand, a mixture of 7-amino-3-[(1-hexyl-1H-tetrazol-5-yl)thiomethyl]-3-cephem-4-carboxylic acid (5.89 g) and trimethylsilyl acetamide (16 g) in methylene chloride (150 ml) was warmed to make a clear solution. The solution was cooled to −15° C. and added all at once to the activated acid solution prepared above. The reaction mixture was stirred for 30 minutes at −15° to 0° C. and for additional 30 minutes at ambient temperature. The solvent was removed by distillation from the reaction mixture under reduced pressure to give a residue, to which ethyl acetate (150 ml) and water (100 ml) were added, and then the mixed solution was adjusted to pH 3 with an aqueous solution of sodium bicarbonate. The organic layer was separated out, washed two times with an aqueous solution of sodium chloride and dried over magnesium sulfate, and then evaporated to dryness to give a brownish oil. This oil was washed three times with diethyl ether (70 ml) and triturated with diisopropyl ether to give a powder of 7-[2-(6-formamidopyridin-2-yl)-2-hydroxyiminoacetamido]-3-(1-hexyl-1H-tetrazol-5-yl)thiomethyl]-3-cephem-4-carboxylic acid (syn isomer), mp 74°-84° C. (dec.).

I.R.$\nu_{max}^{Nujol}$: 3300, 1785, 1700-1675, 1580, 1380, 1260, 810 cm$^{-1}$.

N.M.R.δppm (DMSO-d$_6$): 0.8-1.8 (11H,m), 3.7 (2H,m), 4.3 (4H,m), 5.18 (1H,d, J=4.5 Hz), 5.95 (1H,d,d,J=4.5 Hz, 8 Hz), 7.5-9.43 (5H,m), 10.6 (1H,m).

The following compound was obtained according to the similar manner to that of Example 14-(11).

(12) 7-[2-(6-Formamidopyridin-2-yl)-2-hydroxyiminoacetamido]-3-[(1-allyl-1H-tetrazol-5-yl)thiomethyl]-3-cephem-4-carboxylic acid (syn isomer), mp 88°-91° C. (dec.).

I.R.$\nu_{max}^{Nujol}$: 3300, 1785, 1700-1660, 1580, 1380, 1260, 815 cm$^{-1}$.

N.M.R.δppm (DMSO-d$_6$): 3.63 (2H, broad s), 4.13, 4.43 (2H, ABq,J=13 Hz), 4.93 (2H,m), 5.0-5.2 (1H,m), 5.25 (2H,m), 5.67-6.16 (2H,m), 6.38-8.08 (3H,m), 9.3 (1H,d,J=8 Hz), 10.55 (1H,m).

(13) A mixture of 2-(4-aminopyrimidin-2-yl)-2-methoxyiminoacetic acid dihydrate (syn isomer) (1.62 g) and phosphoryl chloride (4.3 g) in methylene chloride (10 ml) was stirred for 30 minutes at 0° to 5° C. To the above mixture was added dropwise N,N-dimethylformamide (5.3 ml) and the resultant mixture was stirred for 30 minutes at 0° to 5° C.

On the other hand, a mixture of 7-amino-3-[(1-allyl-1H-tetrazol-5-yl)thiomethyl]-3-cephem-4-carboxylic acid (2.5 g) and trimethylsilyl acetamide (10 g) in methylene chloride (35 ml) was warmed to make a clear solution. The solution was cooled to −5° C. and added to the activated acid solution obtained above.

The reaction mixture was stirred for 30 minutes at 5° to 10° C. and for additional 30 minutes at ambient temperature and then poured into a cold aqueous solution of sodium bicarbonate. The aqueous layer was separated out, adjusted to pH 3 with 10% hydrochloric acid, washed with ethyl acetate and then subjected to column chromatography over nonionic adsorption resin, "Diaion HP20" (Trade Mark, manufactured by Mitsubishi Chemical Industries Ltd.) (70 ml). The column was washed with water and eluted with 30% aqueous methanol. The eluent containing a desired compound was evaporated to remove the methanol under reduced pressure and then lyophilized to give 7-[2-(4-aminopyrimidin-2-yl)-2-methoxyiminoacetamido]-3-[1-allyl-1H-tetrazol-5-yl)thiomethyl-3-cephem-4-carboxylic acid (syn isomer) (1.58 g), mp 151°–156° C. (dec.).

I.R.$\nu_{max}^{Nujol}$: 3370, 3220, 1780, 1680~1640 cm$^{-1}$.

N.M.R.δppm (DMSO-d$_6$): 3.7 (2H,m), 3.95 (3H, s), 4.23, 4.48 (2H,ABq,J=13 Hz), 4.8–5.4 (5H,m), 5.7–6.2 (2H,m), 6.45 (1H,d,J=7 Hz), 7.05 (2H, broad s), 8.10 (1H,d,J=7 Hz), 9.45 (1H,d,J=8 Hz).

(14) A mixture of 2-(4-aminopyrimidin-2-yl)-2-methoxyiminoacetic acid (syn isomer) (2.32 g) and phosphoryl chloride (4.6 g) in methylene chloride (15 ml) was stirred for 30 minutes at 3° C. To the mixture was added dropwise a solution of N,N-dimethylformamide (3.0 ml) in methylene chloride (15 ml) and stirred for 40 minutes at 3° C. A solution of 4-nitrobenzyl 7-amino-3-cephem-4-carboxylate (3.20 g) and trimethylsilyl acetamide (15 g) in methylene chloride (60 ml) was cooled to −5° C. and added to the activated acid solution obtained above. The mixture was stirred for 30 minutes at 3° to 5° C. and for additional 30 minutes at ambient temperature. The solvent was evaporated to dryness and the residue was dissolved in ethyl acetate (200 ml). The solution was washed with an aqueous solution of sodium bicarbonate and water, dried over anhydrous magnesium sulfate and evaporated to dryness. The residue was washed with diethyl ether to give 4-nitrobenzyl 7-[2-(4-aminopyrimidin-2-yl)-2-methoxyiminoacetamido]-3-cephem-4-carboxylate (syn isomer) (3.1 g) as a powder, mp 125°–131° C. (dec.).

I.R.$\nu_{max}^{Nujol}$: 3500, 3400, 3250, 1790, 1720, 1690, 1640, 1525, 1040, 855, 740 cm$^{-1}$.

The following compounds were obtained according to the similar manner to those of Examples 1-(13) and (14).

(15) 7-[2-(4-aminopyrimidin-2-yl)-2-methoxyimino acetamido]-2-methyl-3-cephem-4-carboxylic acid (syn isomer), mp 175°–181° C. (dec.).

I.R.$\nu_{max}^{Nujol}$: 3400, 3300, 1780, 1665, 1635, 1590 cm$^{-1}$.

N.M.R.δppm (DMSO-d$_6$): 1.45 (3H,d,J=7 Hz), 3.78 (1H,d,J=7 Hz), 3.95 (3H,s), 5.10 (1H,d,J=4.5 Hz), 5.93 (1H, d,d,J=4.5 Hz, 8 H4c), 6.45 (1H,d, J=7 Hz), 6.57 (1H,d,J=6 Hz), 7.05 (2H, broad s), 8.10 (1H,d, J=6 Hz), 9.41 (1H,d,J=8 Hz).

(16) 7-[2-(4-Aminopyrimidin-2-yl)-2-methoxyimino acetamido]-3-methyl-3-cephem-4-carboxylic acid (syn isomer), mp 169°–175° C. (dec.).

I.R.$\nu_{max}^{Nujol}$: 3350, 3210, 1765, 1680, 1630, 1580, 1375, 1040, 920, 720 cm$^{-1}$.

N.M.R.δppm (DMSO-d$_6$): 2.03 (3H,s), 3.25, 3.66 (2H, ABq, J=18 Hz), 3.95 (3H,s), 5.08 (1H,d,J=4.5 Hz), 5.76 (1H,d,d,J=4.5 Hz,8.0 Hz), 6.43 (1H,d,J=7 Hz), 7.03(2H, broad s), 8.10 (1H,d,J=7 Hz), 9.37 (1H,d,J=8.0 Hz)

(17) 7-[2-(4-Aminopyrimidin-2-yl)-2-methoxyiminoacetamido]-3-carbomoyloxymethyl-3-cephem-4-carboxylic acid (syn isomer), mp 200°–204° C. (dec.).

I.R.$\nu_{max}^{Nujol}$: 3370, 3200, 1775, 1710, 1670-1630, 1400, 1320, 1040, 985, 720 cm$^{-1}$.

N.M.R.δppm (DMSO-d$_6$): 3.38, 3.61 (2H,ABq,J=18 Hz), 3.94 (3H,s), 4.62, 4.90 (2H,ABq,J=13 Hz), 5.15(1H,d,J=4.5 Hz), 5.80 (1H,d,d,J=4.5 Hz, 8.0 Hz), 6.44 (1H,d,J=7.0 Hz), 6.58 (2H,s), 7.03 (2H,broad s), 8.10 (1H,d,J=7.0 Hz), 9.41 (1H, d,J=8.0 Hz).

(18) 7-[2-(4-Aminopyrimidin-2-yl)-2-methoxyiminoacetamido]-3-acetylthiomethyl-3-cephem-4-carboxylic acid (syn isomer), mp 168°–173° C. (dec.).

I.R.$\nu_{max}^{Nujol}$: 3400, 3240, 1780, 1680-1630 cm$^{-1}$.

N.M.R.δppm (DMSO-d$_6$): 2.33 (3H,s), 3.2, 3.7 (2H, ABq,J=18 Hz), 3.92 (3H,s), 3.9–4.2 (2H,m), 5.10 (1H,d,J=4.5 Hz), 5.78 (1H,d,d,J=4.5 Hz,8 Hz), 6.40 (1H,d,J=6 Hz),7.02 (2H,broad s), 8.08 (1H,d,J=6 Hz), 9.37 (1H, d,J=8 Hz).

(19) 4-Nitrobenzyl 7-[2-(4-aminopyrimidin-2-yl)-2-methoxyiminoacetamido]-3-chloro-3-cephem-4-carboxylate (syn isomer), mp 100°–108° C. (dec.).

I.R.$\nu_{max}^{Nujol}$: 3370, 3210, 1780, 1740, 1680, 1630, 1520, 1375, 1350, 1220, 1040, 850, 735 cm$^{-1}$.

N.M.R.δppm (DMSO-d$_6$): 3.75, 4.07 (2H,ABq, J=18 Hz), 3.93 (3H,s), 5.30 (1H, d,J=4.5 Hz), 5.45 (2H,s), 5.95 (1H,d,d,J=4.5 Hz, 8.0 Hz), 6.42 (1H,d,J=7.0 Hz), 7.06 (2H, broad s), 7.68 (2H,d,J=8.0 Hz), 8.22 (2H,d,J=8.0 Hz), 8.08 (1H,d,J=7.0 Hz), 9.53 (1H,d,J=8.0 Hz).

(20) Sodium 7-[2-(4-Aminopyrimidin-2-yl)-2-methoxy iminoacetamido]-3-[5-(4-chlorophenyl)-1,3,4-oxadiazol-2-ylthiomethyl]-3-cephem-4-carboxylate (syn isomer), mp 211°–221° C. (dec.).

I.R.$\nu_{max}^{Nujol}$: 3370, 3220, 1765, 1670-1600, 1400, 1090, 1040, 835, 728 cm$^{-1}$.

N.M.R.δppm (DMSO-d$_6$): 3.3–3.7 (2H,m), 3.90 (3H,s), 4.4 (2H,m), 5.00 (1H,d,J=4.5 Hz), 5.6 (1H,m), 6.45 (1H, d,J=7 Hz), 7.05 (2H,broad s), 7.5–8.1 (4H,m), 8.10 (1H,d,J=7 Hz), 9.3 (1H,m).

(21) 7-[2-(4-Amino-6-chloropyrimidin-2-yl)-2-methoxyiminoacetamido]-3-(1,3,4-thiadiazol-2-ylthiomethyl)-3-cephem-4-carboxylic acid (syn isomer), mp 173°–178° C. (dec.).

I.R.$\nu_{max}^{Nujol}$: 3400, 3280, 1780, 1680, 1630, 1575, 1530, 1380, 1040, 900, 800 cm$^{-1}$.

N.M.R.δppm (DMSO-d$_6$): 3.72 (2H,broad s), 4.00 (3H,s), 4.28, 4.63 (2H, ABq, J=13 Hz), 5.17 (1H,d,J=4.5 Hz), 5.85 (1H,d,d,J=4.5 Hz, 8.0 Hz), 6.50 (1H,s), 7.4 (2H,broad s), 9.50 (1H,d,J=8.0 Hz), 9.58 (1H,s).

(22) 7-[2-(4-Aminopyrimidin-2-yl)-2-ethoxyiminoacetamido]-3-(1,3,4-thiadiazol-2-ylthiomethyl)-3-cephem-4-carboxylic acid (syn isomer).

I.R.$\nu_{max}^{Nujol}$: 3350, 3250, 1780, 1660, 1585 cm$^{-1}$.

(23) 7-[2-(4-Aminopyrimidin-2-yl)-2-propoxyiminoacetamido]-3-(1,3,4-thiadiazol-2-ylthiomethyl)-3-cephem-4-carboxylic acid (syn isomer).

I.R.$\nu_{max}^{Nujol}$: 3375, 3225, 1780, 1660, 1590, 1540 cm$^{-1}$.

(24) 7-[2-Allyloxyimino-2-(4-aminopyrimidin-2-yl)acetamido]-3-(1,3,4-thiadiazol-2-ylthiomethyl)-3-cephem-4-carboxylic acid (syn isomer).

I.R.$\nu_{max}^{Nujol}$: 3380, 3230, 1780, 1660, 1585, 1540 cm$^{-1}$.

(25) 7-[2-(4-Aminopyrimidin-2-yl)-2-benzyloxyiminoacetamido]-3-(1,3,4-thiadiazol-2-ylthiomethyl)-3-cephem-4-carboxylic acid (syn isomer).

I.R.$\nu_{max}^{Nujol}$: 3370, 3230, 1780, 1660, 1590, 1540 cm$^{-1}$.

(26) 7-[2-(6-Aminopyridin-2-yl)-2-hydroxyiminoacetamido]-3-[(1-hexyl-1H-tetrazol-5-yl)thiomethyl]-3-cephem-4-carboxylic acid (syn isomer).

I.R.$\nu_{max}^{Nujol}$: 3200, 1780, 1670, 1620, 810, 725 cm$^{-1}$.

(27) 7-[2-(6-Aminopyridin-2-yl)-2-hydroxyiminoacetamido]-3-[1-allyl-1H-tetrazol-5-yl)thiomethyl]-3-cephem-4-carboxylic acid (syn isomer).

I.R.$\nu_{max}^{Nujol}$: 3350, 3200, 1775, 1665, 1620, 1250, 990, 805 cm$^{-1}$.

(28) 7-[2-(6-Aminopyridin-2-yl)-2-methoxyiminoacetamido]-3-[1-allyl-1H-tetrazol-5-yl)thiomethyl]-3-cephem-4-carboxylic acid (syn isomer).

I.R.$\nu_{max}^{Nujol}$: 3380, 3240, 1780, 1670, 1620 cm$^{-1}$.

(29) 7-[2-(6-Aminopyridin-2-yl)-2-(2,2,2-trifluoro ethoxyimino)acetamido]-3-[(1-carboxymethyl-1H-tetrazol-5-yl)thiomethyl]-3-cephem-4-carboxylic acid (syn isomer).

I.R.$\nu_{max}^{Nujol}$: 3440, 3320, 1778, 1688, 1665, 1623, 1552 cm$^{-1}$.

(30) 7-[2-(6-Aminopyridin-2-yl)-2-propargyloxyiminoacetamido]-3-(1,3,4-thiadiazol-2-ylthiomethyl)-3-cephem-4-carboxylic acid (syn isomer).

I.R.$\nu_{max}^{Nujol}$: 3300, 3200, 2160, 1775, 1735, 1670, 1630, 1085, 1025 cm$^{-1}$.

(31) 7-[2-(4-Aminopyrimidin-2-yl)-2-methoxyiminoacetamido]-3-cephem-4-carboxylic acid (syn isomer).

I.R.$\nu_{max}^{Nujol}$: 3380, 3240, 1780, 1680-1630, 1585, 1378, 1040, 985, 725 cm$^{-1}$.

(32) 7-[2-(4-Aminopyrimidin-2-yl)-2-methoxyiminoacetamido]-3-chloro-3-cephem-4-carboxylic acid (syn isomer).

I.R.$\nu_{max}^{Nujol}$: 3460, 3400, 3260, 1773, 1680-1650, 1620, 1570, 1380, 1270, 1095, 1040, 860 cm$^{-1}$.

(33) 7-[2-(4-Aminopyrimidin-2-yl)-2-methoxyiminoacetamido]-3-(pyrazin-2-ylthiomethyl)-3-cephem-4-caroxylic acid (syn isomer).

I.R.$\nu_{max}^{Nujol}$: 3350, 3250, 1780, 1660, 1590 cm$^{-1}$.

(34) 7-[2-(4-Aminopyrimidin-2-yl)-2-methoxyiminoacetamido]-3-(tetrazolo[1,5-b]pyridazin-6-ylthiomethyl)-3-cephem-4-carboxylic acid (syn isomer).

I.R.$\nu_{max}^{Nujol}$: 3350, 1770, 1660, 1530 cm$^{-1}$.

(35) 7-[2-(4-Amino-6-methoxypyrimidin-2-yl)-2-methoxyiminoacetamido]-3-(1,3,4-thiadiazol-2-yl)thiomethyl-3-cephem-4-carboxylic acid, mp 161°-163° C. (dec.).

I.R.$\nu_{max}^{Nujol}$: 3400, 3250, 1780, 1675, 1620, 1580, 1380, 1040 cm$^{-1}$.

N.M.R.δppm(DMSO-d$_6$): 3.73(2H, broad s), 3.83(3H,s), 3.97(3H,s), 4.27,4,63(2H, ABq,J=13 Hz), 5.17(1H,d,J=4.5 Hz), 5.73 (1H,s), 5.87(1H,d,d,J=4.5 Hz, 8 Hz), 6.77 (2H,broad s), 9.45(1H,m), 9.57(1H,s).

(36) 7-[2-(4-Amino-6-phenylthiopyrimidin-2-yl)-2-methoxyiminoacetamido]-3-(1,3,4-thiadiazol-2-yl)-thiomethyl-3-cephem-4-carboxylic acid, mp 148°-160° C.(dec.).

I.R.$\nu_{max}^{Nujol}$: 3370, 3250, 1780, 1680, 1630, 1570, 750, 722 cm$^{-1}$.

N.M.R. δppm(DMSO-d$_6$): 3.7(2H,m), 3.95 (3H,s), 4.28,4,60(2H,ABq,J=13 Hz), 5.16 (1H,d,J=4.5 Hz), 5.8(2H,m), 6.98(2H, broad s), 7.60(5H,s), 9.47(1H,d,J=8 Hz), 9.59 (1H,s).

EXAMPLE 15

(1) A solution of 7-[2-ethoxyimino-2-(4-formamidopyrimidin-2-yl)acetamido]-3-(1,3,4-thiadiazol-2-ylthiomethyl)-3-cephem-4-carboxylic acid (syn isomer) (3.97 g) and concentrated hydrochloric acid (0.73 ml) in methenol (80 ml) was stirred for 1.5 hours at ambient temperature. The solvent was evaporated to dryness and the residue was dissolved in water (100 ml). The aqueous solution was washed with ethyl acetate and adjusted to pH 3 with an aqueous solution of sodium bicarbonate and then subjected to column chromatography over nonionic adsorption resin, "Diaion HP 20". The column was washed with water and eluted with 50% aqueous methanol. The eluent containing a desired compound was evaporated to remove the methanol and then lyophilized to give 7-[2-(4-aminopyrimidin-2-yl)-2-ethoxyiminoacetamido]-3-(1,3,4-thiadiazol-2-ylthiomethyl)-3-cephem-4-carboxylic acid (syn isomer) (1.75 g), mp 155°-160° C. (dec.).

I.R.$\nu_{max}^{Nujol}$: 3350, 3250, 1780, 1660, 1585 cm$^{-1}$.

N.M.R.δppm (DMSO-d$_6$): 1.27 (3H,t,J=7 Hz), 3.72 (2H, broad s), 4.22 (2H,q, J=7 Hz), 4.33, 4.58 (2H,ABq, J=13 Hz), 5.17 (1H,d,J=5 Hz), 5.87 (1H,dd,J=5 Hz, and 8 Hz), 6.45 (1H,d,J=6 Hz), 7.03 (2H, broad s), 8.12 (1H,d,J=6 Hz), 9.37 (1H,d, J=8 Hz), 9.57 (1H,s).

The following compounds were obtained according to the similar manner to that of Example 15-(1).

(2) 7-[2-(4-Aminopyrimidin-2-yl)-2-propoxyiminoacetamido]-3-(1,3,4-thiadiazol-2-ylthiomethyl)-3-cephem-4-carboxylic acid (syn isomer), mp 145°-150° C. (dec.).

I.R.$\nu_{max}^{Nujol}$: 3375, 3225, 1780, 1660, 1590, 1540 cm$^{-1}$.

N.M.R.δppm (DMSO-d$_6$): 0.90 (3H,t,J=7 Hz), 1.4-1.8 (2H,m), 3.58, 3.74 (2H, ABq,J=18 Hz), 4.08 (2H,t,J=7 Hz), 4.26, 4.54 (2H, ABq,J=13 Hz), 5.12 (1H,d,J=5 Hz), 5.80 (1H,d,d, J=5 Hz, 8 Hz), 6.40 (1H,d,J=6 Hz), 7.00 (2H,s), 8.06 (1H,d,J=6 Hz), 9.36 (1H,d,J=8 Hz), 9.52 (1H,s).

(3) 7-[2-Allyloxyimino-2-(4-aminopyrimidin-2-yl)acetamido]-3-(1,3,4-thiadiazol-2-ylthiomethyl)-3-cephem-4-carboxylic acid (syn isomer), mp 150°-153° C. (dec.).

I.R.$\nu_{max}^{Nujol}$: 3380, 3230, 1780, 1660, 1585, 1540 cm$^{-1}$.

N.M.R.δppm (DMSO-d$_6$): 3.7 (2H,broad s), 4.30, 4.57 (2H,ABq,J=13 Hz), 4.68 (2H,d,J=5 Hz), 5.13 (1H,d, J=5 Hz), 5.0-5.6 (2H,m), 5.85 (1H,d,d,J=5 Hz, 8 Hz), 5.7-6.2(1H,m), 6.42 (1H,d,J=6 Hz), 7.02 (2H, broad s), 8.10 (1H,d,J=6 Hz), 9.43 (1H,d,J=8 Hz), 9.57 (1H,s).

(4) 7-[2-(4-Aminopyrimidin-2-yl)-2-benzyloxyiminoacetamido]-3-(1,3,4-thiadiazol-2-ylthiomethyl)-3-cephem-4-carboxylic acid (syn isomer), mp 145°-150° C. (dec.).

I.R.$\nu_{max}^{Nujol}$: 3370, 3230, 1780, 1660, 1590, 1540 cm$^{-1}$.

N.M.R.δppm (DMSO-d$_6$): 3.6 (2H,broad s), 4.33, 4.57 (2H, ABq,J=13 Hz), 5.15 (1H, d,J=5 Hz), 5.28 (2H,s), 5.87 (1H, d,d,J=5 Hz, 8 Hz), 6.47 (1H,d,J=6 Hz), 7.0-7.3 (2H,m), 7.40 (5H,s), 8.13 (1H,d,J=6 Hz), 9.55 (1H,d,J=8 Hz), 9.60 (1H,s).

(5) 7-[2-(6-Aminopyridin-2-yl)-2-hydroxyiminoacetamido]-3-[(1-hexyl-1H-tetrazol-5-yl)thiomethyl]-3-cephem-4-carboxylic acid (syn isomer), mp 148°-153° C. (dec.).

I.R.$\nu_{max}^{Nujol}$: 3200, 1780, 1670, 1620, 810, 725 cm$^{-1}$.

N.M.R.δppm (DMSO-d₆): 0.8-1.8 (11H,m), 3.73 (2H, broad s), 4.4 (4H,m)m 5.17 (1H,d,J=4.5 Hz), 5.87 (1H, d,d,J=4.5 Hz, 8 Hz), 6.63 (1H,d,J=8 Hz), 6.88 (1H,d,J=8 Hz), 7.53 (1H,t,J=8 Hz), 9.45 (1H,d,J=8 Hz).

(6) 7-[2-(6-Aminopyridin-2-yl)-2-hydroxyiminoacetamido]-3-[(1allyl-1H-tetrazol-5-yl)thiomethyl]-3-cephem-4-carboxylic acid (syn isomer), mp 168°-171° C. (dec.).

I.R.$\nu_{max}^{Nujol}$: 3350, 3200, 1775, 1665, 1620, 1250, 990, 805 cm⁻¹.

N.M.R.δppm (DMSO-d₆): 3.75 (2H, broad s), 4.20, 4.52 (2H,ABq,J=14 Hz), 5.0 (2H,m), 5.06 (1H,d,J=4.5 Hz), 5.3 (2H,m), 5.8-5.9 (2H,m), 6.65 (1H,d,J=8 Hz), 6.91 (1H,d,J=8 Hz), 7.50 (1H,t,J=8 Hz), 9.4 (1H,d, J=8 Hz).

(7) 7-[2-(6-Aminopyridin-2-yl)-2-methoxyiminoacetamido]-3-[(1-allyl-1H-tetrazol-5-yl)thiomethyl]-3-cephem-4-carboxylic acid (syn isomer), mp 148°-149° C. (dec.).

I.R.$\nu_{max}^{Nujol}$: 3380, 3240, 1780, 1670, 1620 cm⁻¹.

N.M.R.δppm (DMSO-d₆): 3.73(2H,broad s), 3.93 (3H,s), 4.21, 4.54 (2H,ABq,J=14 Hz), 5.0 (2H,m), 5.15 (1H,d,J=4.5 Hz), 5.3 (2H,m), 5.8 (1H,m), 5.85 (1H,d,d,J=4.5 Hz, 8 Hz), 6.51 (1H,d,J=8 Hz), 6.91 (1H,d,J=8 Hz), 7.48 (1H, t,J=8 Hz), 9.5 (1H,d,J=8 Hz).

(8) 7-[2-(6-Aminopyridin-2-yl)-2-(2,2,2-trifluoroethoxyimino)acetamido]-3-[(1-carboxymethyl-1H-tetrazol-5-yl)thiomethyl]-3-cephem-4-carboxylic acid (syn isomer), mp 178° C. (dec.).

I.R.$\nu_{max}^{Nujol}$: 3440, 3320, 1778, 1688, 1665, 1623, 1552 cm⁻¹.

N.M.R.δppm (DMSO-d₆): 3.60,3.74 (2H,ABq,J=19 Hz), 4.22,4.48 (2H,ABq,J=14 Hz), 4.68, 4.84 (2H,ABq,J=9 Hz), 5.12 (1H,d,J=5 Hz), 5.30 (2H,s), 5.83 (1H,d,d,J=5 Hz, 8 Hz), 6.56 (1H,d,J=8 Hz), 6.90 (1H,d,J=8 Hz), 7.48 (1H,t,J=8 Hz), 9.66 (1H,d,J=8 Hz).

(9) 7-[2-(6-Aminopyridin-2-yl)-2-propargyloxyiminoacetamido]-3-(1,3,4-thiadiazol-2-ylthiomethyl)-3-cephem-4-carboxylic acid (syn isomer), mp 168°-175° C. (dec.).

I.R.$\nu_{max}^{Nujol}$: 3300, 3200, 2160, 1775, 1735, 1670, 1630, 1085, 1025 cm⁻¹.

N.M.R.δppm (DMSO-d₆): 3.6 (3H,m), 4.30, 4.60 (2H,Abq,J=13 Hz), 5.00 (2H,s), 5.22 (1H,d,J=4.5 Hz), 5.83 (1H,d,d,J=4.5 Hz, 8.0 Hz), 6.80 (1H,d,J=6 Hz), 7.16 (1H,d,J=6 Hz), 7.90 (1H,t,J=6 Hz), 9.60 (1H,s), 10.01 (1H,d,J=8 Hz).

(10) 7-[2-(4-Aminopyrimidin-2-yl)-2-methoxyiminoacetamido]-3-[(1-allyl-1H-tetrazol-5-yl)thiomethyl]-3-cephem-4-carboxylic acid (syn isomer).

I.R.$\nu_{max}^{Nujol}$: 3370, 3220, 1780, 1680-1640 cm⁻¹.

(11) 7-[2-(4-Aminopyrimidin-2-yl)-2-methoxyiminoacetamido]-3-cephem-4-carboxylic acid (syn isomer).

I.R.$\nu_{max}^{Nujol}$: 3380, 3240, 1780, 1680-1630, 1585, 1378, 1040, 985, 725 cm⁻¹.

(12) 7-[2-(4-Aminopyrimidin-2-yl)-2-methoxyimino acetamido]-2-methyl-3-cephem-4-carboxylic acid (syn isomer).

I.R.$\nu_{max}^{Nujol}$: 3400, 3300, 1780, 1665, 1635, 1590 cm⁻¹.

(13) 7-[2-(4-Aminopyrimidin-2-yl)-2-methoxyimino acetamido]-3-methyl-3-cephem-4-carboxylic acid (syn isomer).

I.R.$\nu_{max}^{Nujol}$: 3350, 3210, 1765, 1680-1630, 1580, 1375, 1040, 920, 720 cm⁻¹.

(14) 7-[2-(4-Aminopyrimidin-2-yl)-2-methoxyiminoacetamido]-3-carbamoyloxymethyl-3-cepyem-4-carboxylic acid (syn isomer).

I.R.$\nu_{max}^{Nujol}$: 3370, 3200, 1775, 1710, 1670-1630, 1400, 1320, 1040, 985, 720 cm⁻¹.

(15) 7-[2-(4-Aminopyrimidin-2-yl)-2-methoxyiminoacetamido]-3-acetylthiomethyl-3-cephem-4-carboxylic acid (syn isomer)

I.R.$\nu_{max}^{Nujol}$: 3400, 3240, 1780, 1680-1630 cm⁻¹.

(16) 7-[2-(4-Aminopyrimidin-2-yl)-2-methoxyiminoacetamido]-3-chloro-3-cephem-4-carboxylic acid (syn isomer).

I.R.$\nu_{max}^{Nujol}$: 3460, 3400, 3260, 1773, 1680-1650, 1620, 1570, 1380, 1270, 1095, 1040, 860 cm⁻¹.

(17) Sodium 7-[2-(4-Aminopyrimidin-2-yl)-2-methoxyiminoacetamido]-3-[5-(4-chlorophenyl)-1,3,4-oxadiazol-2-ylthiomethyl]-3-cephem-4-carboxylate (syn isomer).

I.R.$\nu_{max}^{Nujol}$: 3370, 3220, 1765, 1670-1600, 1400, 1090, 1040, 835, 728 cm⁻¹.

(18) 7-[2-(4-Amino-6-chloropyrimidin-2-yl)-2-methoxyiminoacetamido]-3-(1,3,4-thiadiazol-2-ylthiomethyl)-3-cephem-4-carboxylic acid (syn isomer).

I.R.$\nu_{max}^{Nujol}$: 3400, 3280, 1780, 1680, 1630, 1575, 1530, 1380, 1040, 900, 800 cm⁻.

(19) 7-[2-(4-Aminopyrimidin-2-yl)-2-methoxyiminoacetamido]-3-(pyrazin-2-ylthiomethyl)-3-cephem-4-carboxylic acid (syn isomer).

I.R.$\nu_{max}^{Nujol}$: 3350, 3250, 1780, 1660, 1590 cm⁻¹.

(20) 7-[2-(4-Aminopyrimidin-2-yl)-2-methoxyiminoacetamido]-3-(tetrazolo[1,5-b]pyridazin-6-ylthiomethyl)-3-cephem-4-carboxylic acid (syn isomer).

I.R.$\nu_{max}^{Nujol}$: 3350, 1770, 1660, 1530 cm⁻¹.

(21) 7-[2-(4-Amino-6-methoxypyrimidin-2-yl)-2-methoxyiminoacetamido]-3-(1,3,4-thiadiazol-2-yl)thiomethyl-3-cephem-4-carboxylic acid.

I.R. $\nu_{max}^{Nujol}$: 3400, 3250, 1780, 1675, 1620, 1580, 1380, 1040 cm⁻¹.

(22) 7-[2-(4-Amino-6-phenylthiopyrimidin-2-yl)-2-methoxyiminoacetamido]-3-(1,3,4-thiadiazol-2-yl)thiomethyl-3-cephem-4-carboxylic acid.

I.R.$\nu_{max}^{Nujol}$: 3370, 3250, 1780, 1680, 1630, 1570, 750, 722 cm⁻¹.

EXAMPLE 16

A solution of 7-[2-allyloxyimino-2-(6-formamidopyridin-2-yl)acetamido]3-(5-tert-butoxycarbonylaminomethyl-1,3,4-thiadiazol-2-ylthiomethyl)-3-cephem-4-carboxylic acid (sym isomer) (2.7 g) in formic acid (27 ml) was stirred for 2 hours at ambient temperature and evaporated to dryness. To the residue were added methanol (50 ml) and concentrated hydrochloric acid (0.82 g), and the mixture was stirred for an hour at ambient temperature. The solvent was evaporated and the residue was dissolved in water (50 ml), adjusted to pH 4 to 5 with an aqueous solution of sodium bicarbonate, treated with an activated charcoal and then subjected to column chromatography over nonionic adsorption resin, "Diaion HP 20" (80 ml). The column was washed with water and eluted with 50% aqueous methanol. The eluent containing a desired compound was evaporated to remove the methanol and then lyophilized to give 7-[2-allyloxyimino-2-(6-aminopyridin-2-yl)acetamido]-3-(5-aminomethyl-1,3,4-thiadiazol-2-ylthiomethyl)-31-cephem-4-carboxylic acid (syn isomer) (0.6 g), mp 180° C. (dec.).

I.R.$\nu_{max}^{Nujol}$: 3400, 3250, 1770, 1670, 1620 cm$^{-1}$.

N.M.R.δppm (DMSO-d$_6$+D$_2$O): 3.63 (2H, broad s), 4.2–4.8 (6H,m), 4.8–6.3 (5H,m), 6.53 (1H,d,J=8 Hz), 6.90 (1H,d,J=8 Hz), 7.47 (1H,t,J=8 Hz).

EXAMPLE 17

(1) A mixture of 4-nitrobenzyl 7-[2-(4-aminopyrimidin-2-yl)-2-methoxyiminoacetamido]-3-cephem-4-carboxylate (syn isomer) (3.0 g) and 10% palladium on carbon (1.5 g) in 50% aqueous tetrahydrofuran (90 ml) was stirred under hydrogen atmosphere for 3 hours at ambient temperature. The catalyst was removed by filtration and the filtrate was concentrated to half of the original volume. The remaining aqueous solution was diluted with water (100 ml), washed with ethyl acetate, adjusted to pH 3 with 10% hydrochloric acid and subjected to column chromatography over nonionic adsorption resin, "Diaion HP20". The column was washed with water and eluted with 10% methanol. The eluent containing a desired compound was evaporated to remove the methanol in vacuo and then lyophilized to give 7-[2-(4-amino-pyrimidin-2-yl)-2-methoxyiminoacetamido]-3-cephem-4-carboxylic acid (syn isomer) (750 mg), mp 191°–197° C. (dec.).

I.R.$\nu_{max}^{Nujol}$: 3380, 3240, 1780, 1680-1630, 1585, 1378, 1040, 985, 725 cm$^{-1}$.

N.M.R.δppm (DMSO-d$_6$): 3.6 (2H,m), 4.00 (3H,s), 5.13 (1H,d,J=4.5 Hz), 5.91 (1H,dd,J=4.5 Hz,8 Hz), 6.50(1H,d,J=7 Hz), 6.6 (1H,m), 7.03 (2H, broad s), 8.17 (1H,d,J=7 Hz), 9.47 (1H,d,J=8 Hz).

The following compounds were obtained according to the similar manner to that of Example 17-(1).

(2) 7-[2-(4-Aminopyrimidin-2-yl)-2-methoxyiminoacetamido]-3-chloro-3-cephem-4-carboxylic acid (syn isomer), mp 200°–205° C. (dec.).

I.R.$\nu_{max}^{Nujol}$: 3460, 3400, 3260, 1773, 1680-1650, 1620, 1570, 1380, 1270, 1095, 1040, 860 cm$^{-1}$.

N.M.R.δppm (DMSO-d$_6$): 3.60, 4.03 (2H,ABq, J=18 Hz), 3.95 (3H,s), 5.25 (1H,d,J=4.5 Hz), 5.85 (1H,d,d, J=4.5 Hz, 8.0 Hz), 6.43 (1H,d,J=7 Hz), 7.03 (2H, broad s), 8.11 (1H,d,J=7.0 Hz), 9.50 (1H,d,J=8.0 Hz).

(3) 7-[2-(4-Aminopyrimidin-2-yl)-2-methoxyiminoacetamido]-3-[1-allyl-1H-tetrazol-5-yl)thiomethyl]-3-cephem-4-carboxylic acid (syn isomer).

I.R.$\nu_{max}^{Nujol}$: 3370, 3220, 1780, 1680-1640 cm$^{-1}$.

(4) 7-[2-(4-Aminopyrimidin-2-yl)-2-methoxyiminoacetamido]-2-methyl-3-cephem-4-carboxylic acid (syn isomer).

I.R.$\nu_{max}^{Nujol}$: 3400, 3300, 1780, 1665, 1635, 1590 cm$^{-1}$.

(5) 7-[2-(4-Aminopyrimidin-2-yl)-2-methoxyiminoacetamido]-3-methyl-3-cephem-4-carboxylic acid (syn isomer).

I.R.$\nu_{max}^{Nujol}$: 3350, 3210, 1765, 1680–1630, 1580, 1375, 1040, 920, 720 cm$^{-1}$.

(6) 7-[2-(4-Aminopyrimidin-2-yl)-2-methoxyiminoacetamido]-3-carbamoyloxymethyl-3-cephem-4-carboxylic acid (syn isomer).

I.R.$\nu_{max}^{Nujol}$: 3370, 3200, 1775, 1710, 1670-1630, 1400, 1320, 1040, 985, 720 cm$^{-1}$.

(7) 7-[2-(4-Aminopyrimidin-2-yl)-2-methoxyiminoacetamido]-3-acetylthiomethyl-3-cephem-4-carboxylic acid (sym isomer).

I.R.$\nu_{max}^{Nujol}$: 3400, 3240, 1780, 1680-1630 cm$^{-1}$.

(8) Sodium 7-[2-(4-Aminopyrimidin-2-yl)-2-methoxyiminoacetamido]-3-[5-(4-chlorophenyl)-1,3,4-oxadiazol-2-ylthiomethyl]-3-cephem-4-carboxylate (sym isomer).

I.R.$\nu_{max}^{Nujol}$: 3370, 3220, 1765, 1670-1600, 1400, 1090, 1040, 835, 728 cm$^{-1}$.

(9) 7-[2-(4-Amino-6-chloropyrimidin-2-yl)-2-methoxyiminoacetamido]-3-(1,3,4-thiadiazol-2-ylthiomethyl)-3-cephem-4-carboxylic acid (syn isomer).

I.R. $\nu_{max}^{Nujol}$: 3400, 3280, 1780, 1680, 1630, 1575, 1530, 1380, 1040, 900, 800 cm$^{-1}$.

(10) 7-[2-(4-Aminopyrimidin-2-yl)-2-ethoxyiminoacetamido]-3-(1,3,4-thiadiazol-2-ylthiomethyl)-3-cephem-4-carboxylic acid (syn isomer).

I.R. $\nu_{max}^{Nujol}$: 3350, 3250, 1780, 1660, 1585 cm$^{-1}$.

(11) 7-[2-(4-Aminopyrimidin-2-yl)-2-propoxyiminoacetamido]-3-(1,3,4-thiadiazol-2-ylthiomethyl)-3-cephem-4-carboxylic acid (syn isomer).

I.R. $\nu_{max}^{Nujol}$: 3375, 3225, 1780, 1660, 1590, 1540 cm$^{-1}$.

(12) 7-[2-Allyloxyimino-2-(4-aminopyrimidin-2-yl)acetamido]-3-(1,3,4-thiadiazol-2-ylthiomethyl)-3-cephem-4-carboxylic acid (syn isomer).

I.R. $\nu_{max}^{Nujol}$: 3380, 3230, 1780, 1660, 1585, 1540 cm$^{-1}$.

(13) 7-[2-(4-Aminopyrimidin-2-yl)-2-benzyloxyiminoacetamido]-3-(1,3,4-thiadiazol-2-ylthiomethyl)-3-cephem-4-carboxylic acid (syn isomer).

I.R. $\nu_{max}^{Nujol}$: 3370, 3230, 1780, 1660, 1590, 1540 cm$^{-1}$.

(14) 7-[2-(6-Aminopyridin-2-yl)-2-hydroxyiminoacetamido]-3-[(1-hexyl-1H-tetrazol-5-yl)thiomethyl]-3-cephem-4-carboxylic acid (syn isomer).

I.R. $\nu_{max}^{Nujol}$: 3200, 1780, 1670, 1620, 810, 725 cm$^{-1}$.

(15) 7-[2-(6-Aminopyridin-2-yl)-2-hydroxyiminoacetamido]-3-[(1-allyl-1H-tetrazol-5-yl)thiomethyl]-3-cephem-4-carboxylic acid (sym isomer).

I.R. $\nu_{max}^{Nujol}$: 3350, 3200, 1775, 1665, 1620, 1250, 990, 805 cm$^{-1}$.

(16) 7-[2-(6-Aminopyridin-2-yl)-2-methoxyiminoacetamido]-3-[(1-allyl-1H-tetrazol-5-yl)thiomethyl]-3-cephem-4-carboxylic acid (syn isomer).

I.R. $\nu_{max}^{Nujol}$: 3380, 3240, 1780, 1670, 1620 cm$^{-1}$.

(17) 7-[2-(6-Aminopyridin-2-yl)-2-(2,2,2-trifluoroethoxyimino)acetamido]-3-[(1-carboxymethyl-1H-tetrazol-5-yl)thiomethyl]-3-cephem-4-carboxylic acid (syn isomer).

I.R. $\nu_{max}^{Nujol}$: 3440, 3320, 1778, 1688, 1665, 1623, 1552 cm$^{-1}$.

(18) 7-[2-(6-Aminopyridin-2-yl)-2-propagyloxyimino acetamido]-3-(1,3,4-thiadiazol-2-ylthiomethyl)-3-cephem-4-carboxylic acid (syn isomer).

I.R. $\nu_{max}^{Nujol}$: 3300, 3200, 2160, 1775, 1735, 1670, 1630, 1085, 1025 cm$^{-1}$.

(19) 7-[2-(4-Aminopyrimidin-2-yl)-2-methoxyiminoacetamido]-3-(pyrazin-2-ylthiomethyl)-3-cephem-4-carboxylic acid (syn isomer).

I.R. $\nu_{max}^{Nujol}$: 3350, 3250, 1780, 1660, 1590 cm$^{-1}$.

(20) 7-[2-4-Aminopyrimidin-2-yl)-2-methoxyiminoacetamido]-3-(tetrazolo[1,5-b]pyridazin-6-ylthiomethyl)-3-cephem-4-carboxylic acid (syn isomer).

I.R. $\nu_{max}^{Nujol}$: 3350, 1770, 1660, 1530 cm$^{-1}$.

(21) 7-[2-(4-Amino-6-methoxypyrimidin-2-yl)-2-methoxyiminoacetamido]-3-(1,3,4-thiadiazol-2-yl)-thiomethyl-3-cephem-4-carboxylic acid.

I.R. $\nu_{max}^{Nujol}$: 3400, 3250, 1780, 1675, 1620, 1580, 1380, 1040 cm$^{-1}$.

(22) 7-[2-(4-Amino-6-phenylthiopyrimidin-2-yl)-2-methoxyiminoacetamido]-3-(1,3,4-thiadiazol-2-yl)-thiomethyl-3-cephem-4-carboxylic acid.

I.R.$\nu_{max}^{Nujol}$: 3370, 3250, 1780, 1680, 1570, 750, 722 cm$^{-1}$.

(23) Benzhydryl 7-[2-(6-formamidopyridin-2-yl)-2-methoximinoacetamido]-7-methoxy-3-(1-methyl-1H-tetrazol-5-yl)thiomethyl-3-cephem-4-carboxylate (1.1 g) was added to a cooled mixture of trifluoroacetic acid (10 ml) and anisole (2 ml), and stirred under ice cooling for 30 minutes. After removing the solvent from the resultant solution, the residue was triturated with diethyl ether. The precipitates were collected by filtration and washed with diethyl ether to give 7-[2-(6-formamidopyridin-2-yl)-2-methoxyiminoacetamido]-7-methoxy-3-(1-methyl-1H-tetrazol-5-yl)thiomethyl-3-cephem-4-carboxylic acid (900 mg), mp 124° to 128° C. (dec.).

I.R. $\nu_{max}^{Nujol}$: 3400-3200, 1780, 1700, 1670 cm$^{-1}$.

N.M.R. δppm (aceton-d$_6$): 3.59 (3H, s), 3.63, 3.76 (2H, AB-q, J=18 Hz), 4.00 (6H, s), 4.36 (2H, broad s), 5.13 (1H, s), 6.90–8.10 (3H, m).

EXAMPLE 18

(1) A mixture of 7-[2-(2,2,2-trifluoroethoxyimino)-2-(6-formamidopyridin-2-yl)acetamido]cephalosporanic acid (4.7 g), disodium salt of 2-(5-mercapto-1H-tetrazol-1-yl)acetic acid (2.3 g) and sodium bicarbonate (0.72 g) in phosphate buffer (pH 6.4, 150 ml) was stirred for 3 hours at 60° to 65° C. and then for 2 hours with an additional disodium salt of 2-(5-mercapto-1H-tetrazol-1-yl)acetic acid (0.88 g) at the same temperature. The reaction mixture was cooled in an ice bath, adjusted to pH 4.5 with 10% hydrochloric acid and washed with ethyl acetate. The aqueous solution was acidified to pH 1 with 10% hydrochloric acid and extracted with ethyl acetate. The extract was washed with water, dried over anhydrous magnesium sulfate and evaporated to dryness. The residue was triturated with diethyl ether and washed with the same solvent to give crude 7-[2-(2,2,2-trifluoroethoxyimino)-2-(6-formamidopyridin-2-yl)acetamido]-3-[(1-carboxymethyl-1H-tetrazol-5-yl)thiomethyl]-3-cephem-4-carboxylic acid (syn isomer) (2.3 g).

This compound was identified by transforming it to 7-[2-(2,2,2-trifluoroethoxyimino)-2-(6-aminopyridin-2-yl)acetamido]-3-[(1-carboxymethyl-1H-tetrazol-5-yl)thiomethyl]-3-cephem-4-carboxylic acid (syn isomer) according to the similar manner to that of Example 2-(8).

I.R. $\nu_{max}^{Nujol}$: 3440, 3320, 1778, 1688, 1665, 1623, 1552 cm$^{-1}$.

The following compound was obtained according to the similar manner to that of Example 18-(1).

(2) 7-[2-(4-Formamidopyrimidin-2-yl)-2-methoxyimino acetamido]-3-(tetrazolo[1,5-b]pyridazin-6-ylthiomethyl)-3-cephem-4-carboxylic acid (syn isomer), mp 170°-175° C. (dec.).

I.R. $\nu_{max}^{Nujol}$: 3250, 1780, 1710, 1680, 1570 cm$^{-1}$.

N.M.R. δppm (DMSO-d$_6$): 3.76 (2H, broad, s), 4.00 (3H, s), 4.27, 4.63 (2H, ABq,J=14 Hz), 5.20 (1H, d,J=4 Hz), 5.90 (1H,d,d,J=4 Hz,8 Hz), 7.43 (1H, broad s), 7.77 (1H,d,J=10 Hz), 8.58 (1H,d,J=10 Hz), 8.70 (1H,d,J=4 Hz), 9.10 (1H, broad s), 9.55 (1H,d,J=8 Hz).

(3) A mixture of 7-[2-(4-formamidopyrimidin-2-yl)-2-methoxyiminoacetamido]-3-acetoxymethyl-3-cephem-4-carboxylic acid (syn isomer) (2.8 g), 2-mercaptopyrazine (0.853 g) and sodium bicarbonte (1.48 g) in phosphate buffer (pH 6.86, 120 ml) was stirred for 3 hours at 70° C. The reaction mixture was cooled in an ice bath and adjusted to pH 2 with 10% hydrochloric acid. A resultant solid was filtered and the filtrate was washed three times with ethyl acetate. The solid was dissolved in a mixture of ethyl acetate, acetone and water, and then the aqueous layer was separated out. The filtrate and the aqueous layer were combined, concentrated in vacuo to remove acetone and ethyl acetate and, then subjected to column chromatography over nonionic adsorption resin, "Diaion HP 20".

The column was washed with water and 20% aqueous methanol and eluted with 50% aqueous methanol. The eluent was evaporated to remove the methanol in vacuo and then lyophilized to give 7-[2-(4-aminopyrimidin-2-yl)-2-methoxyiminoacetamido]-3-(pyrazin-2-ylthiomethyl)-3-cephem-4-carboxylic acid (syn isomer) (0.9 g), mp 175°–180° C. (dec.).

I.R. $\nu_{max}^{Nujol}$: 3350, 3250, 1780, 1660, 1590 cm$^{-1}$.

N.M.R. δppm (DMSO-d$_6$): 3.55, 3.73 (2H,Abq,J=18 Hz), 4.00 (3H,s), 4.10, 4.62 (2H,ABq,J=13 Hz) 5.17 (1H,d,J=4 Hz), 5.83 (1H,d,d,J=4 Hz, 8 Hz), 6.48 (1H,d,J=6 Hz), 7.10 (2H,s), 8.15 (1H,d,J=6 Hz), 8.30-8.67 (3H,m), 9.45 (1H,d,J=8 Hz)

The following compounds were obtained according to the similar manner to that of Example 5-(3).

(4) 7-[2-(4-Aminopyrimidin-2-yl)-2-methoxyiminoacetamido]-3-](1-allyl-1H-tetrazol-5-yl)thiomethyl]-3-cephem-4-carboxylic acid (syn isomer).

I.R. $\nu_{max}^{Nujol}$: 3370, 3220, 1780, 1680-1640 cm$^{-1}$.

(5) Sodium 7-[2-(4-Aminopyrimidin-2-yl)-2-methoxyiminoacetamido]-3-[5-(4-chlorophenyl)-1,3,4-oxadiazol-2-ylthiomethyl]-3-cephem-4-carboxylate (syn ismer).

I.R. $\nu_{max}^{Nujol}$: 3370, 3220, 1765, 1670-1600, 1400, 1090, 1040, 835, 728 cm$^{-1}$.

(6) 7-[2-(4-Amino-6-chloropyrimidin-2-yl)-2-methoxyiminoacetamido]-3-(1,3,4-thiadiazol-2-ylthiomethyl)-3-cephem-4-carboxylic acid (syn isomer).

I.R. $\nu_{max}^{Nujol}$: 3400, 3280, 1780, 1680, 1630, 1575, 1530, 1380, 1040, 900, 800 cm$^{-1}$.

(7) 7-[2-(4-Aminopyrimidin-2-yl)-2-ethoxyiminoacetamido]-3-(1,3,4-thiadiazol-2-ylthiomethyl)-3-cephem-4-carboxylic acid (syn isomer).

I.R. $\nu_{max}^{Nujol}$: 3350, 3250, 1780, 1660, 1585 cm$^{-1}$.

(8) 7-[2-(4-Aminopyrimidin-2-yl)-2-propoxyiminoacetamido]-3-(1,3,4-thiadiazol-2-ylthiomethyl)-3-cephem-4-carboxylic acid (syn isomer).

I.R. $\nu_{max}^{Nujol}$: 3375, 3225, 1780, 1660, 1590, 1540 cm$^{-1}$.

(9) 7-([2-Allyloxyimino-2-(4-aminopyrimidin-2-yl) acetamido]-3-(1,3,4-thiadiazol-2-ylthiomethyl)-3-cephem-4-carboxylic acid (syn isomer).

I.R. $\nu_{max}^{Nujol}$: 3380, 3230, 1780, 1660, 1585, 1540 cm$^{-1}$.

(10) 7-[2-(4-Aminopyrimidin-2-yl)-2-benzyloxyiminoacetamido]-3-(1,3,4-thiadiazol-2-ylthiomethyl)-3-cephem-4-carboxylic acid (syn isomer).

I.R. $\nu_{max}^{Nujol}$: 3370, 3230, 1780, 1660, 1590, 1540 cm$^{-1}$.

(11) 7-[2-(6-Aminopyridin-2-yl)-2-hydroxyiminoacetamido]-3-[(1-hexyl-1H-tetrazol-5-yl)thiomethyl]-3-cephem-4-carboxylic acid (syn isomer).

I.R. $\nu_{max}^{Nujol}$: 3200, 1780, 1670, 1620, 810, 725 cm$^{-1}$.

(12) 7-[2-(6-Aminopyridin-2-yl)-2-hydroxyiminoacetamino]-3-[(1-allyl-1H-tetrazol-5-yl)thiomethyl]-3-cephem-4-carboxylic acid (syn isomer).

I.R. $\nu_{max}^{Nujol}$: 3350, 3200, 1775, 1665, 1620, 1250, 990, 805 cm$^{-1}$.

(13) 7-[2-(6-Aminopyridin-2-yl)-2-methoxyiminoacetamido]-3-[(1-allyl-1H-tetrazol-5-yl)thiomethyl]-3-cephem-4-carboxylic acid (syn isomer).

I.R. $\nu_{max}^{Nujol}$: 3380, 3240, 1780, 1670, 1620 cm$^{-1}$.

(14) 7-[2-(6-Aminopyridin-2-yl)-2-(2,2,2-trifluoroethoxyimino)acetamido]-3-[(1-carboxymethyl-1H-tetrazol-5-yl)thiomethyl]-3-cephem-4-carboxylic acid (syn isomer).

I.R. $\nu_{max}^{Nujol}$: 3440, 3320, 1778, 1688, 1665, 1623, 1552 cm$^{-1}$.

(15) 7-[2-(6-Aminopyridin-2-yl)-2-propargyloxyiminoacetamido]-3-(1,3,4-thiadiazol-2-ylthiomethyl)-3-cephem-4-carboxylic acid (syn isomer).

I.R. $\nu_{max}^{Nujol}$: 3300, 3200, 2160, 1775, 1735, 1670, 1630, 1085, 1025 cm$^{-1}$.

(16) 7-[2-(4-Aminopyrimidin-2-yl)-2-methoxyiminoacetamido]-3-tetrazolo[1,5-b]pyridazin-6-ylthiomethyl)-3-cephem-4-carboxylic acid (syn isomer), mp 200°-203° C. (dec.).

I.R. $\nu_{max}^{Nujol}$: 3350, 1770, 1660, 1530 cm$^{-1}$.

N.M.R. δppm (DMSO-d$_6$): 3.63, 3.77 (2H, ABq, J=18 Hz), 3.93 (3H,s), 4.23, 4.60 (2H,ABq,J=14 Hz), 5.12(1H,d,J=4 Hz), 5.85 (1H,d,d,J=4 Hz,8 Hz), 6.45 (1H,d,j=6 Hz), 7.10 (2H,s), 7.75. (1H,d,J=10 Hz), 8.12 (1H,d,J=6 Hz), 8.60 (1H,d,J=10 Hz), 9.43(1H,d,J=8 Hz).

(17) 7-[2-(4-Amino-6-methoxypyrimidin-2-yl)-2-methoxyiminoacetamido]-3-(1,3,4-thiadiazol-2-yl-thiomethyl-3-cephem-4-carboxylic acid.

I.R. $\nu_{max}^{Nujol}$: 3400, 3250, 1780, 1675, 1620, 1580, 1380, 1040 cm$^{-1}$.

(18) 7-[2-(4-Amino-6-phenylthiopyrimidin-2-yl)-2-methoxyiminoacetamido]-3-(1,3,4-thiadiazol-2-yl)thiomethyl-3-cephem-4-carboxylic acid.

I.R. $\nu_{max}^{Nujol}$: 3370, 3250, 1780, 1680, 1630, 1570, 750, 722 cm$^{-1}$.

EXAMPLE 19

7-[2-(4-Aminopyrimidin-2-yl)-2-methoxyiminoacetamido]-3-[1-(2-tert-butoxycarbonylaminoethyl)-1H-tetrazol-5-yl]thiomethyl-3-cephem-4-carboxylic acid (syn isomer) was obtained by reacting 7-amino-3-[1-(2-tert-butoxycarbonylaminoethyl)-1H-tetrazol-5-yl]thiomethyl-3-cephem-4-carboxylic acid, which can be prepared from 7-aminocephalosporanic acid and 1-(2-tert-butoxycarbonylaminoethyl)-1H-tetrazole-5-thiol, with 2-(4-aminopyrimidin-2-yl)-2-methoxyiminoacetic acid (syn isomer) in substantially the same manner as that of Example 14-(1).

Physical constant of 7-amino-3-[1-(2-tert-butoxycarbonylaminoethyl)-1H-tetrazol-5-yl]thiomethyl-3-cephem-4-carboxylic acid: mp 185°-189° C. (dec.)

I.R. $\nu_{max}^{Nujol}$: 3420, 3200, 1810, 1700 1620, 1525, 1290, 1175 cm$^{-1}$. N.M.R. δppm (NaHCO$_3$+D$_2$O): 1.33 (9H, s), 3.3-3.9 (4H, m), 4.20, 4.40 (2H, ABq, J=13 Hz), 4.5-4.9 (2H, m), 5.10 (1H, d, J=5 Hz), 5.51 (1H, d, J=5 Hz).

Physical constant of 7-[2-(4-aminopyrimidin-2-yl-2-methoxyiminoacetamido]-3-[1-(2-tert-butoxycarbonylaminoethyl)-1H-tetrazol-5-yl]thiomethyl-3-cephem-4-carboxylic acid (syn isomer);

I.R. $\nu_{max}^{Nujol}$: 3400, 3220, 1790, 1720-1640, 1530, 1260, 1175, 1055, 725 cm$^{-1}$.

N.M.R. δppm (DMSO-d$_6$+D$_2$O): 1.66 (9H, s), 3.0-3.7 (2H, m), 3.7 (2H, m), 4.12 (3H, s), 4.4 (4H, m), 5.19 (1H, d, J=5 Hz), 5.86 (1H, d, J=5 Hz), 6.90 (1H, d, J=7 Hz), 8.23 (1H, d, J=7 Hz).

EXAMPLE 20

7-[2-(4-Aminopyrimidin-2-yl)-2-methoxyiminoacetamido]-3-[1-(2-aminoethyl)-1H-tetrazol-5-yl]-thiomethyl-3-cephem-4-carboxylic acid (syn isomer) was obtained from the object compound in Example 19 in substantially the same manner as that of Example 3, mp 183°-195° C. (dec.).

I.R. $\nu_{max}^{Nujol}$: 3400, 3220, 1770, 1660, 1630, 1590, 1540, 1180, 1040 cm$^{-1}$.

N.M.R. δppm (DMSO-d$_6$+D$_2$O): 3.1-3.8 (4H, m), 3.99 (3H, s), 4.3 (2H, m), 4.7 (2H, m), 5.12 (1H, d, J=5 Hz), 5.82 (1H, d, J=5 Hz), 6.61 (1H, d, J=7 Hz), 8.28 (1H, d, J=7 Hz),

EXAMPLE 21

(1) Methylene chloride (15 ml) was added to a Vilsmeier reagent, which was prepared by phosphoryl chloride (0.75 g) and N,N-dimethylformamide (0.75 ml) in a conventional manner. To this mixture was added 2-(4-formamidopyrimidin-2-yl)-2-phenoxyiminoacetic acid (syn isomer) (1.0 g) at −20° C., followed by stirring at −15° to −13° C. for half an hour. To this solution was added a solution of 7-amino-3-(1,3,4-thiadiazol-2-ylthiomethyl)-3-cephem-4-carboxylic acid (1.27 g) and trimethylsilylacetamide (4.6 g) in methylene chloride (14 ml) at −20° C. with stirring, and the stirring was continued at −15° to −13° C. for half an hour and at ambient temperature for additional half an hour. The reaction mixture was evaporated to give a residue, to which ethyl acetate and then an aqueous solution of sodium bicarbonate were added. To the separated aqueous solution was added ethyl acetate and then adjusted to pH 1 to 2 with hydrochloric acid.

After addition of a small amount of acetone, the oganic layer was separated, washed with water and an aqueous solution of sodium chloride, dried over magnesium sulfate, and then evaporated. The residue was pulverized with diethyl ether to give 7-[2-(4-formamidopyrimidin-2-yl)-2-phenoxyiminoacetamido]-3-(1,3,4-thiadiazol-2-ylthiomethyl)-3-cephem-4-carboxylic acid (syn isomer) (1.45 g).

I.R. $\nu_{max}^{Nujol}$: 1780, 1710, 1660, 1570, 1210, 1060, 1000, 760 cm$^{-1}$.

N.M.R. δppm (DMSO-d$_6$): 3.73 (2H, m), 4.27, 4.67 (2H, ABq, J=12 Hz), 5.27 (1H, d, J=5 Hz), 5.97 L (1H, dd, J=5 Hz, 8 Hz), 6.9-7.6 (5H, m), 7.7-8.2 (1H, m), 8.77 (1H, d, J=6 Hz), 9.10 (1H, m), 9.54 (1H, s), 9.83 (1H, d, J=8 Hz), 11.10 (1H, d, J=7 Hz).

(2) 7-[2-(4-Formamidopyrimidin-2-yl)-2-phenoxyiminoacetamido]-3-[1-(2-tert-butoxycarbonylaminoethyl)-1H-tetrazol-5-ylthiomethyl]-3-cephem-4-carboxylic acid (syn isomer) (1.8 g) was obtained by reacting 7-amino-3-[1-(2-tert-butoxycarbonylaminoethyl)-1H-tetrazol-5-ylthiomethyl]-3-cephem-4-carboxylic acid (2.12 g) with an activated acid prepared from 2-(4-formamidopyrimidin-2-yl)-2-phenoxyiminoacetic acid (syn isomer) (1.1 g), phosphoryl chloride (0.83 g) and N,N-dimethylformamide (0.8 ml), in substantially the same manner as that of Example 21-(1).

I.R. $\nu_{max}^{Nujol}$: 3300-3100, 1700, 1715-1660, 1570, 1250, 1210, 1160, 990, 850, 760 cm$^{-1}$.

N.M.R. δppm (DMSO-d$_6$): 1.25 (9H, s), 3.23 (2H, m), 3.70 (2H, m), 4.27 (4H, m), 5.17 (1H, d, J=5 Hz), 5.90 (1H, m), 6.8-7.6 (5H, m), 7.90 (1H, m), 8.73 (1H, d, J=6 Hz), 9.83 (1H, d, J=8 Hz), 11.20 (1H, d, J=7 Hz).

EXAMPLE 22

(1) A solution of 7-[2-(4-formamidopyrimidin-2-yl)-2-phenoxyiminoacetamido]-3-(1,3,4-thiadiazol-2-ylthiomethyl)-3-cephem-4-carboxylic acid (syn isomer) (1.40 g) and coc. hydrochloric acid (0.23 ml) in methanol (20 ml) was stirred at ambient temperature for 1.5 hours.

The reaction mixture was poured into diethyl ether (150 ml) with stirring, followed by the precipitates were collected by filtration, washed with diethyl ether and dried to give a pale yellow powder (1.2 g). To this powder was added water (6 ml) and the suspension was stirred for 20 minutes. The remaining powder was collected by filtration, washed with water and then dried in vacuo to give a pale yellow powder (0.96 g) of hydrochloric acid salt of 7-[2-(4-aminopyrimidin-2-yl)-2-phenoxyiminoacetamido]-3-(1,3,4-thiadiazol-2-ylthiomethyl)-3-cephem-4-carboxylic acid (syn isomer), mp 155°–161° C. (dec.).

I.R. $\nu_{max}^{Nujol}$: 3300, 3160, 1770, 1650, 1580, 1200, 1060, 1000, 980, 760 cm$^{-1}$.

N.M.R. δppm (DMSO-d6+D$_2$O): 3.76 (2H, m), 4.11, 4.64 (2H, ABq, J=13 Hz), 5.28 (1H, d, J=5 Hz), 5.95 (1H, d, J=5 Hz), 6.73 (1H, d, J=6 Hz), 7.0–7.6 (5H, m), 8.30 (1H, d, J=6 Hz), 9.63 (1H, s)

(2) A solution of formic acid salt of 7-[2-(4-formamidopyrimidin-2-yl)-2-phenoxyiminoacetamido]-3-[1-(2-aminoethyl)-1H-tetrazol-5-ylthiomethyl]-3-cephem-4-carboxylic acid (syn isomer) (1.5 g) and conc. hydrochloric acid (0.45 ml) in methanol (20 ml) was stirred at ambient temperature for 1.5 hours. The reaction mixture was concentrated till the precipitates appeared therein, and to the concentrate was added water (double volume of said concentrate).

The aqueous solution was chromatographed on non-ionic adsorption resin "Diaion HP-20" (Trade Mark: maker Mitsubishi Chemical Industries Ltd.) (60 ml) with 20% aqueous methanol (500 ml), 30% aqueous methanol (300 ml) and then 60% aqueous methanol (500 ml) as an eluent, and the fractions containing a desired compound were collected. These fractions were concentrated to a volume of 150 ml and the concentrate was lyophilized to give a pale yellow powder (0.55 g) of 7-[2-(4-aminopyrimidin-2-yl)-2-phenoxyiminoacetamido]-3-[1-(2-aminoethyl)-1H-tetrazol-5-ylthiomethyl]-3-cephem-4-carboxylic acid (syn isomer), mp 217°–227° C. (dec.).

I.R. $\nu_{max}^{Nujol}$: 3300, 3160, 1760, 1660, 1620, 1580, 1200, 980, 950, 760 cm$^{-1}$.

N.M.R. δppm (DMSO-d6+D$_2$O): 3.1–3.8 (4H, m), 4.27 (2H, m), 4.69 (2H, m), 5.17 (1H, d, J=5 Hz), 5.87 (1H, d, J=5 Hz), 6.60 (1H, d, J=6 Hz), 7.0–7.7 (5H, m), 8.27 (1H, d, J=6 Hz).

EXAMPLE 23

To 7-[2-(4-formamidopyrimidin-2-yl)-2-phenoxyiminoacetamido]-3-[1-(2-tert-butoxycarbonylaminoethyl)-1H-tetrazol-5-ylthiomethyl]-3-cephem-4-carboxylic acid (syn isomer) (1.7 g) was added formic acid (17 ml) and the solution was stirred at ambient temperature for 4 hours. After the reaction mixture was evaporated, the residue was pulverized with ethyl acetate to give a brown powder (1.5 g) of formic acid salt of 7-[2-(4-formamidopyrimidin-2-yl)-2-phenoxyiminoacetamido]-3-[1-(2-aminoethyl)-1H-tetrazol-5-ylthiomethyl]-3-cephem-4-carboxylic acid (syn isomer).

I.R. $\nu_{max}^{Nujol}$: 3200, 1770, 1710, 1660, 1570, 1210, 990, 760 cm$^{-1}$.

Preparation of the starting compounds

Preparation 1

(1) A 15% n-hexane solution (636 g.) of n-butyllithium was added to a solution of 6-amino-2-methylpyridine (64.8 g.) in tetrahydrofuran (500 ml.) at −20° to −30° C. over one hour, and stirred at −8° to −10° C. for 30 minutes. To the solution was added trimethylsilylchloride (161.7 g.) at −15° to −5° C. over 40 minutes, and the resultant solution was stirred at room temperature overnight. The solution was filtered through by a column packed with silica gel (180 g.), washed with tetrahydrofuran and then the filtrate was concentrated under reduced pressure. The residue was purified by fractional distillation to give 6-[N,N-bis(-trimethylsilyl)amino]-2-methylpyridine (117.6 g.), b.p. 95° to 97° C./5–6 mm.

N.M.R. δppm (CCl$_4$): 0.13 (18H, s), 2.35 (3H, s), 6.43 (1H, d, J=8 Hz), 6.60 (1H, d, J=8 Hz), 7.25 (1H, t, J=8 Hz).

(2) A 15% n-hexane solution (338.6 g.) of n-butyllithium was dropwise added to a solution of 6-[N,N-bis(-trimethylsilyl)amino]-2-methylpyridine (100 g.) in anhydrous tetrahydrofuran (300 ml.) at −20° to −30° C. over one hour and the solution was stirred at 20° to 23° C. for one hour. The resultant solution was added in small portions to crushed dry ice (1 kg.) under stirring, and stirred till a room temperature. After removing tetrahydrofuran from the solution under reduced pressure, absolute ethanol (1 l) was added to the residue. 30% Ethanol solution (660 ml.) of hydrochloric acid was dropwise added to the solution at −5° to −10° C., and further hydrogen chloride gas was bubbled at 0° to 5° C. for 30 minutes and then the solution was stirred at 10° C. overnight. After removing ethanol from the resultant solution, the residue was dissolved in water, and washed with ethyl acetate 3 times. The solution was adjusted to pH 7 to 8 with sodium bicarbonate and extracted with ethyl acetate. The ethyl acetate extract was washed with a saturated aqueous solution of sodium chloride, dried and concentrated under reduced pressure to give the crude product (54 g.). The product was purified by column chromatography on silica gel (1 kg.) with an eluent (ethyl acetate+benzene) to give ethyl 2-(6-aaminopyridin-2-yl)acetate (30.2 g.), mp 66° L to 68° C.

I.R. $\nu_{max}^{Nujol}$: 3430, 3340, 3200, 1730, 1645, 1480, 1190 cm$^{-1}$.

N.M.R. δppm (CDCl$_3$): 1.25 (3H, t, J=6 Hz), 3.67 (2H, s), 4.20 (2H, q, J=6 Hz), 5.33 (2H, broad s), 6.43 (1H, d, J=8 Hz), 6.62 (1H, d, J=8 Hz), 7.40 (1H, t, J=8 Hz).

(3) Acetic anhydride (16.6 ml.) and 98% formic acid (7.32 ml.) were mixed at room temperature and stirred at 50° to 66° C. for 30 minutes. The solution was dropwise added to a solution of ethyl 2-(6-aminopyridin-2-yl)acetate (26.5 g.) in ethyl acetate (250 ml.) at 20° to 23° C. over 30 minutes, and stirred at the same temperature for one hour. Cool water was added to the resultant solution and shaked sufficiently. The ethyl acetate layer was separated, washed with water, an aqueous solution of sodium bicarbonate and water in turn, dried and concentrated under reduced pressure to give ethyl 2-(6-formamidopyridin-2-yl)acetate (28 g.), mp 35° to 38° C.

I. R. $\nu_{max}^{Nujol}$: 3250, 3100, 1738, 1690, 1580, 1460, 1305, 1277 cm$^{-1}$.

N.M.R. δppm (DMSO-d$_6$): 1.17 (3H, t, J=8 Hz), 3.75 (2H, s), 4.08 (2H, q, J=8 Hz), 6.85 (0.5H, broad d, J=8 Hz), 7.95 (0.5H, broad s), 7.08 (1H, d, J=8 Hz), 7.73 (1H, t, J=8 Hz), 8.33 (0.5H, broad s), 9.25 (0.5H, broad d), 10.58 (1H, broad s).

(4) To a solution of ethyl 2-(6-formamidopyridin-2-yl)acetate (26 g.) in dioxane (260 ml.) was added selenium dioxide (16.65 g.) in small portions at 85° to 90° C.

over one hour and stirred at the same temperature for one hour. After cooling the resultant solution the dioxane layer was separated and concentrated under reduced pressure and then the residue was dissolved in ethyl acetate. The solution was washed with water, dried over magnesium sulfate and treated with activated charcoal and then concentrated under reduced pressure. The residue was triturated with diethyl ether to give ethyl 2-(6-formamidopyridin-2-yl)glyoxylate (14.3 g.), mp 124° to 126° C.

I. R. $\nu_{max}^{Nujol}$: 3220, 3100, 1737, 1720, 1690, 1273, 1233 cm$^{-1}$.

N.M.R. δppm (DMSO-d$_6$): 1.34 (3H, t, J=8 Hz), 4.44 (2H, q, J=8 Hz), 7.33 (0.65H, broad s), 7.8–8.2 (0.35H), 7.84 (1H, d, J=8 Hz), 8.09 (1H, t, J=8 Hz), 8.44 (0.35H, broad s), 9.22 (0.65H, broad s), 10.85 (1H, broad s).

(5) 2 N Sodium hydroxide solution [solvent:water (1 part)+ethanol (4 parts)] (14.87 ml.) was added to a solution of ethyl 2-(6-formamidopyridin-2-yl)glyoxylate (6.00 g.) in ethanol (180 ml.) at room temperature and stirred at the same temperature for 20 minutes. Methoxyamine hydrochloride (2.71 g.) was added to the resultant solution, stirred at room temperature for 1.5 hours and then concentrated to a small volume under reduced pressure. The precipitates were collected by filteration washed with ethyl acetate and water, dissolved in methanol and then treated with activated charcoal. The solution was concentrated under reduced pressure and then the precipitates were collected by filtration to give 2-(6-formamidopyridin-2-yl)-2-methoxyiminoacetic acid (3.63 g.), mp 170° to 171° C. (dec.).

I. R. $\nu_{max}^{Nujol}$: 3230, 3132, 1745, 1680, 1575, 1450, 1320, 1208, 1032 cm$^{-1}$.

N.M.R. δppm (DMSO-d$_6$): 3.70 (3H, s), 6.90 (0.6H, broad d), 7.9 (0.4H, broad s), 7.10 (1H, d, J=8 Hz), 7.75 (1H, t, J=8 Hz), 8.38 (0.4H, broad s), 9.25 (0.6H, broad d), 10.58 (1H, broad d).

(6) To a solution of ethyl 2-(6-formamidopyridin-2-yl)acetate (4.4 g.) in ethanol (44 ml.) was added 2 N sodium hydroxide solution [solvent:water (1 part)+ethanol (4 parts] (15.9 ml.) at 18° to 20° C. over 30 minutes, and then the solution was stirred at room temperature for one hour. After 1 N hydrochloric acid (31.7 ml.) was added to the solution, the solution was concentrated under reduced pressure. The residue was extracted with hot ethyl acetate (500 ml.) and the extract was concentrated under reduced pressure. The residue was washed with ethyl acetate to give 2-(6-formamidopyridin-2-yl)acetic acid (2.5 g.), mp 125° to 126° C. (dec.).

I.R. $\nu_{max}^{Nujol}$: 3270, 1720, 1655, 1575, 1460 cm$^{-1}$.

N.M.R. δppm (DMSO-d$_6$+D$_2$O): 3.70 (2H, s), 6.9 and 7.9 (1H, m), 7.10 (1H, d, J=8 Hz), 7.75 (1H, t, J=8 Hz), 9.25 and 8.38 (1H, broad s).

(7) A suspension of 2(6-formamidopyridin-2-yl)-2-methoxyiminoacetic acid (1.5 g.) and conc. hydrochloric acid (0.77 g.) in methanol (30 ml.) was stirred at room temperature for 45 minutes. After concentrating the resultant solution under reduced pressure, the residue was washed with diethyl ether. The precipitates were collected by filtration to give 2-(6-aminopyridin-2-yl)-2-methoxyiminoacetic acid hydrochloride (1.63 g.), mp 100° to 105° C.

I. R. $\nu_{max}^{Nujol}$: 3400-3150, 1730, 1670, 1245, 1050, 803 cm$^{-1}$.

N.M.R. δppm (DMSO-d$_6$): 4.13 (3H, s), 6.89 (1H, d, J=8 Hz), 7.22 (1H, d, J=8.5 Hz), 7.95 (1H, dd, J=8.5 Hz, 8 Hz).

(8) Bis(trimethylsilyl)acetamide (1.61 g.) was added to a stirred suspension of 2-(6-aminopyridin-2-yl)-2-methoxyiminoacetic acid hydrochloride (410 mg.) in ethyl acetate (5 ml.) all at once, and stirred at 40° C. for 50 minutes. Trifluoroacetic anhydride (1.3 g.) was dropped into the solution at $-10°$ to $-5°$ C. over 30 minutes, and then the solution was stirred at the same temperature for 3 hours. Ethyl acetate (10 ml.) and water (3 ml.) were added to the resultant solution. The solution was washed with water and a saturated aqueous solution of sodium bicarbonate in turn, dried over magnesium sulfate, and concentrated under reduced pressure to give 2-(6-trifluoroacetamidopyridin-2-yl)-2-methoxyiminoacetic acid (470 mg.), mp 194° to 195° C.

I. R. $\nu_{max}^{Nujol}$: 3350, 1680-1670, 1600, 1380, 1040, 850, 810 cm$^{-1}$.

(9) 1 N Sodium hydroxide (27.5 ml.) was added to a stirred solution of ethyl 2-(6-formamidopyridin-2-yl)glyoxylate (5.55 g.) in ethanol (100 ml.) at room temperature, and the solution was stirred at the same temperature for 30 minutes. To the solution was added hydroxylamine hydrochloride (1.9 g.) all at once, and the solution was stirred at room temperature for 2 hours. After removing ethanol from the resultant solution under reduced pressure, ethylacetate was added to the residue, and then the solution was adjusted to pH 7 with an aqueous solution of sodium bicarbonate. The aqueous layer was separated and adjusted to pH 2 with 10% hydrochloric acid. The precipitates were collected by filtration, washed with water and dried to give 2-(6-formamidopyridin-2-yl)-2-hydroxyiminoacetic acid (3.6 g.), mp 190° to 192° C. (dec.).

I. R. $\nu_{max}^{Nujol}$: 3120, 1700, 1665, 1620 cm$^{-1}$.

(10) A mixture of 2-(6-formamidopyridin-2-yl)-2-hydroxyiminoacetic acid (3.6 g.), dichloroacetyl chloride (7.6 g.) and methylene chloride (100 ml.) was stirred at room temperature for 5 hours. The precipitates were collected by filtration, washed with diethyl ether and dried to give 2-(6-formamidopyridin-2-yl)-2-dichloroacetoxyiminoacetic acid (4.6 g.), mp 88° to 90° C.

I. R. $\nu_{max}^{Nujol}$: 1800, 1720, 1620 cm$^{-1}$.

Preparation 2

(1) A mixture of acetic anhydride (32.7 g.) and formic acid (16.2 g.) was stirred at 50° to 60° C. for 30 minutes. The solution was added to a suspension of methyl 2-(2-aminopyrimidin-4-yl)acetate (17.93 g.) in ethyl acetate (300 ml.) at room temperature over 10 minutes, and the solution was stirred at room temperature for 3 hours. After removing the insoluble substance by filtration, water (300 ml.) was added to the filtrate, and then the mixture was adjusted to pH 7 with sodium bicarbonate. The aqueous layer was separated and extracted with ethyl acetate. The extract and the organic layer were combined, washed with a saturated aqueous solution of sodium chloride, dried over magnesium sulfate, treated with activated charcoal, and then concentrated under reduced pressure. The residue was triturated with diethyl ether to give methyl 2-(2-formamidopyrimidin-4-yl)acetate (14.62 g.), mp 103° to 107° C.

I.R. $\nu_{max}^{Nujol}$: 3000–3400 (multiple), 1740, 1703, 1600, 1567 cm$^{-1}$.

N.M.R. δppm (DMSO-d$_6$): 3.70 (3H, s), 3.90 (2H, s), 7.25 (1H, d, J=5 Hz), 8.60 (1H, d, J=5 Hz), 9.43 (1H, d, J=10 Hz), 11.07 (1H, broad d, J=10 Hz).

(2) Selenium oxide (9.92 g.) was added to a solution of methyl 2-(2-formamidopyrimidin-4-yl)acetate (14.52 g.)

in dioxane (200 ml.) at 90° to 95° C. over 20 minutes, and stirred at the same temperature for an hour. After cooling the resultant solution, the solution was filtered through a column packed with silica gel (20 g.), washed with dioxane and concentrated under reduced pressure. The residue was dissolved in acetone and filtered, and then the filtrate was concentrated under reduced pressure. The residue was triturated with chloroform to give a crude product (8.2 g.). The product was added to ethyl acetate, heated and an insoluble material was filtered out. The filtrate was cooled, and the precipitates were collected by filtration to give methyl 2-(2-formamidopyrimidin-4-yl)glyoxylate (5.55 g.). The product was recrystallized from ethyl acetate (saturated with water) to give mono hydrate thereof, mp 143° to 144° C.

Anal. Calcd. for $C_8H_7N_3O_4 \cdot H_2O$

|  | C | H | N |
|---|---|---|---|
| Calcd. | 42.30 | 3.99 | 18.50 |
| found | 42.22 | 3.95 | 18.34 |

I. R. $\nu_{max}^{Nujol}$: 3270, 3200, 1750, 1710, 1597, 1585, 1416, 1233 cm$^{-1}$.

N.M.R. δppm (DMSO-d$_6$): 3.65 (3H, s), 7.30 (2H, s), 7.40 (1H, d, J=5 Hz), 8.63 (1H, d, J=5 Hz), 9.33 (1H, d, J=10 Hz), 10.95 (1H, bd, J=10 Hz).

(3) 4 N sodium hydroxide (10.85 ml.) was added to a solution of methyl 2-(2-formamidopyrimidin-4-yl)glyoxylate mono hydrate (4.55 g.) in methanol (60 ml.), and the solution was stirred for an hour.

To the solution was added methoxylamine hydrochloride (1.82 g.) little by little, and the solution was stirred at room temperature for 30 minutes, and then under ice cooling for 30 minutes. The precipitates were collected by filtration, and dissolved in water. The insoluble substance was filtered out. The filtrate was adjusted to pH 1 with 10% hydrochloric acid and extracted with ethyl acetate. The extract was washed with a saturated aqueous solution of sodium chloride, and concentrated under reduced pressure. The precipitates were collected by filtration to give 2-(2-formamidopyrimidin-4-yl)-2-methoxyiminoacetic acid (0.63 g.). The methanol solution obtained above was concentrated under reduced pressure, and the residue was dissolved in water. The aqueous solution was treated with activated charcoal, adjusted to pH 1 with 10% hydrochloric acid and extracted with ethyl acetate. The extract was washed with a saturated aqueous solution of sodium chloride and concentrated under reduced pressure. The precipitates were collected by filtration to give the same object compound (0.73 g.), total yield 1.36 g, mp 180° to 182° C. (dec.).

I. R. $\nu_{max}^{Nujol}$: 3300-2400 (multiple), 1750, 1670, 1590, 1573, 1408, 1240, 1048 cm$^{-1}$.

N.M.R. δppm (DMSO-d$_6$): 4.00 (3H, s), 7.47 (1H, d, J=5 Hz), 8.60 (1H, d, J=5 Hz), 9.23 (1H, d, J=10 Hz), 11.02 (1H, broad d, J=10 Hz).

Preparation 3

(1) 1 N Sodium hydroxide solution (8.5 ml.) was added to a stirred solution of ethyl 2-(6-formamidopyridin-2-yl)-glyoxylate (1.9 g.) in ethanol (30 ml.) at room temperature and stirred at the same temperature for 30 minutes. After adding ethoxylamine hydrochloride (912 mg.) to the solution, the solution was stirred at room temperature for 4 hours. The resultant solution was concentrated under reduced pressure, and ethyl acetate and an aqueous solution of sodium bicarbonate were added to the residue. The aqueous layer was separated and ethyl acetate was added to the solution. The solution was adjusted to pH 1 with 10% hydrochloric acid. The ethyl acetate layer was separated, dried over magnesium sulfate and concentrated under reduced pressure. The residue was triturated with a mixture of diethyl ether and petroleum ether to give 2-(6-formamidopyridin-2-yl)-2-ethoxyiminoacetic acid (920 mg.), mp 155° to 156° C. (dec.).

I. R. $\nu_{max}^{Nujol}$: 3250, 1740, 1650 cm$^{-1}$.

N.M.R. δppm (DMSO-d$_6$): 1.3 (3H, t, J=7 Hz), 4.3 (2H, q, J=7 Hz), 6.8–8.2 (3H, m), 9.4 (1H, broad d), 10.5 (1H, broad d)

Preparation 4

(1) A mixture of formic acid (20 g.) and acetic anhydride (41.3 g.) was stirred for 30 minutes at 50° C. and thereto was added methyl 4-amino-2-pyridinecarboxylate (11 g.) at ambient temperature, and then the mixture was stirred for 2 hours at 70°–75° C. After the removal of the solvent from the reaction mixture, the residue was recrystallized from ethanol (160 ml.) to give a pale yellow powder of methyl 4-formamido-2-pyridinecarboxylate (8.3 g.), m.p. 185° to 186.5° C.

I.R. $\nu_{max}^{Nujol}$: 3200-3300, 1690, 1675, 1585, 1570, 1495, 1420, 1260, 990, 860, 840 cm$^{-1}$ (2) To a mixture of methyl 4-formamido-2-pyridinecarboxylate (9.9 g.), methyl methylthiomethyl sulfoxide (6.82 g.) and N,N-dimethylformamide (200 ml.) was added 50% sodium hydride (7.92 g.) with stirring at 10° C. and the stirring was continued for further 10.5 hours at 45° C. After the removal of N,N-dimethylformamide from the reaction mixture, to the residue was added a cold mixture of ethyl acetate and diluted hydrochloric acid. The ethyl acetate layer was separated and the remaining aqueous layer was further extracted with ethyl acetate. The combined extract was washed with an aqueous solution of sodium chloride, dried over magnesium sulfate and the solvent was distilled off. The residue (6.0 g.) was washed with a mixture of ethyl acetate and diethyl ether, collected by filtration and then dried to give the brownish yellow powder of 4-formamido-2-(2-methanesulfinyl-2-methylthioacetyl)pyridine (1.96 g.), mp. 132° to 132.5° C. After the concentration of the filtrate, the precipitates were collected by filtration, washed with diethyl ether and then dried to give the same compound (1.11 g.). Total yield: 3.07 g.

I.R. $\nu_{max}^{Nujol}$: 3200-3225, 1680, 1580, 1290, 1170, 1020, 845 cm$^{-1}$.

(3) After stirring a mixture of acetic anhydride (14 ml.) and formic acid (136 ml.) for 10 minutes at 40° to 50° C., 4-formamido-2-(2-methanesulfinyl-2-methylthioacetyl)pyridine (3.7 g.) was added thereto, and then the stirring was continued at 65° C. for 30 minutes. To the mixture was added sodium periodate (0.872 g.), and the mixture was stirred for 15 minutes. After the removal of the solvent from the reaction mixture, the residue was dissolved in ethyl acetate. The solution was washed with an aqueous solution of sodium bicarbonate, aqueous sodium thiosulfate and water successively, and then dried over anhydrous magnesium sulfate. The solvent was distilled off and the residue was washed with diethyl ether, collected by filtration and then dried to give a pale yellow powder of S-methyl 2-(4-formamidopyridin-2-yl)-thioglyoxylate (1.96 g.), mp 145° to 148° C.

I.R. $\nu_{max}^{Nujol}$: 3150–3300, 1690, 1670, 1585, 1570, 1500, 1420, 1265, 990, 860, 835, 745 cm$^{-1}$.

(4) A mixture of S-methyl 2-(4-formamidopyridin-2-yl)thioglyoxylate (1.07 g.), methanol (20 ml.) and 1 N aqueous solution of sodium hydroxide (5.7 ml.) was stirred for 50 minutes at ambient temperature to give a solutions containing 2-(4-formamidopyridin-2-yl)glyoxylic acid. To the solution was added O-methylhydroxylamine hydrochloride (438 mg.), and the mixture was stirred for an hour at ambient temperature. After the removal of the solvent from the reaction mixture, to the residue was added water (5 ml.), and the mixture was washed with ethyl acetate and then water was distilled off. The remaining water in the residue was azeotropically removed with ethanol and benzene in turn to give a pale brown powder of 2-(4-formamidopyridin-2-yl)-2-methoxyiminoacetic acid (syn isomer) (960 mg.).

N.M.R. δppm (DMSO-d$_6$ + D$_2$O) : 3.93 (3H, s),
7.6 (1H, broad)
8.1 (broad s) ⎫
⎬ (1H)
8.55 (broad s) ⎭
8.45 (1H, broad s)

Preparation 5

(1) A mixture of formic acid (559.3 g.) and acetic anhydride (1033.4 g.) was stirred for 30 minutes at 40° to 50° C. and thereto was added methyl 6-amino-2-pyridinecarboxylate (616 g.) at 40° C., and then the mixture was stirred for 1 hour at 80° C. After the removal of the solvent from the reaction mixture, the residue was dissolved in a mixture of benzene and n-hexane and then filtered. Thus obtained precipitates were recrystallized from benzene (2 l.) to give methyl 6-formamido-2-pyridinecarboxylate (647.8 g.), mp 134° to 136° C.

Element analysis:

|  | C | N | H |
|---|---|---|---|
| Calcd (%) | 53.33 | 4.48 | 15.55 |
| Found (%) | 53.37 | 4.40 | 15.58 |

I.R. $\nu_{max}^{Nujol}$: 3200, 1740, 1700 cm$^{-1}$.

(2) To a mixture of methyl 6-formamido-2-pyridinecarboxylate (435.7 g.), methyl methylthiomethyl sulfoxide (300 g.) and N,N-dimethylformamide (2.2 l.) was added 50% sodium hydride (348 g.) with stirring under ice-cooling, and the mixture was stirred for 30 minutes at ambient temperature. To the reaction mixture was added benzene (4.4 l.) under ice-cooling and the precipitates were collected by filtration. The precipitates were added to a mixture of methylene chloride (3 l.), ice (2 kg.) and concentrated hydrochloric acid (730 ml.). The mixture was adjusted to pH 7 with sodium bicarbonate and then extracted with methylene chloride. The extract was dried over magnesium sulfate and the solvent was distilled off. The residue was crystallized in diethyl ether, collected by filtration and then dried to give 6-formamido-2-(2-methanesulfinyl-2-methylthioacetyl)pyridine (430 g.), mp. 130° to 132° C.

I.R. $\nu_{max}^{Nujol}$: 3250, 3150, 3050, 1710, 1690, 1600, 1510 cm$^{-1}$.

N.M.R. δppm (d$_6$-acetone+D$_2$O): 2.30 (3H, s), 2.88 (3H, s), 6.00 (1H, s), 7.7–8.2 (3H, m).

(3) A mixture of 6-formamido-2-(2-methanesulfinyl-2-methylthioacetyl)pyridine (424 g.), sodium periodate (100 g.) in acetic acid (2.1 l.) was stirred for 30 minutes at 70° C. After the removal of the solvent from the reaction mixture, to the residue were added water (5 l.) and sodium thiosulfate (116 g.), and then the mixture was adjusted to pH 7 with sodium bicarbonate. The precipitates were collected by filtration, washed with water and then dried to give S-methyl 2-(6-formamidopyridin-2-yl)thioglyoxylate (246.4 g.), mp. 163° to 165° C. Further, the same compound (12 g.) was obtained from the aqueous layer by extraction with ethyl acetate.

I.R. $\nu_{max}^{Nujol}$: 3250, 3150, 3080, 1700, 1670, 1595, 1580, 1510 cm$^{-1}$.

N.M.R. δppm (acetone-d$_6$+D$_2$O): 2.57 (3H, s), 7.77–8.27 (3H, m).

(4)(a) A mixture of S-methyl 2-(6-formamidopyridin-2-yl)thioglyoxylate (4.48 g.), methanol (20 ml.) and 1 N aqueous solution of sodium hydroxide (20 ml.) was stirred for 50 minutes at ambient temperature to give a solution containing 2-(6-formamidopyridin-2-yl)glyoxylic acid. To the solution was added O-propylhydroxylamine hydrochloride (2.23 g.), and the mixture was stirred for 35 minutes at the same temperature. The reaction mixture was adjusted to pH 7 with hydrochloric acid and the methanol was distilled off. The remaining aqueous mixture was washed with ethyl acetate, and ethyl acetate was added thereto and then adjusted to pH 1 with 10% hydrochloric acid. The ethyl acetate layer was separated, washed with water, dried over magnesium sulfate, treated with activated charcoal and then the solvent was distilled off. Thus obtained product was washed with a mixture of diethyl ether and diisopropyl ether and then dried to give 2-(6-formamidopyridin-2-yl)-2-propoxyiminoacetic acid (syn isomer) (1.76 g.), mp 140° to 142° C. (dec.).

I.R. $\nu_{max}^{Nujol}$: 3250, 3100, 2600, 1755, 1670, 1620, 1580 cm$^{-1}$.

N.M.R. δppm (acetone-d$_6$+D$_2$O): 0.96 (3H, t, J=7 Hz), 1.56–1.84 (2H, m), 4.2 (2H, t, J=7 Hz), 7.0–8.32 (3H, m).

Similarly, the following compounds were obtained.

(4)(b) 2-(6-Formamidopyridin-2-yl)-2-(2,2,2-trifluoroethoxyimino)acetic acid (syn isomer), mp. 183° to 184° C. (dec.)

I.R. $\nu_{max}^{Nujol}$: 3220, 1760, 1680 cm$^{-1}$.

N.M.R. δppm (DMSO-d$_6$): 4.78, 5.07 (2H, ABq, J=9 Hz), 7.0–8.2 (3H, m), 9.0–9.3 (1H, m), 10.76 (1H, m).

(4)(c) 2-(6-Formamidopyridin-2-yl)-2-isopropoxyiminoacetic acid (syn isomer), mp. 140° to 150° C. (dec.).

I.R. $\nu_{max}^{Nujol}$: 3300, 2600, 1750, 1670, 1620, 1580, 1510 cm$^{-1}$.

N.M.R. δppm (acetone-d$_6$+D$_2$O): 1.3 (6H, d, J=6 Hz), 4.36–4.64 (1H, m), 6.92–8.28 (3H, m).

(4)(d) 2-Allyloxyimino-2-(6-formamidopyridin-2-yl)acetic acid (syn isomer), mp. 140° C. (dec.).

I.R. $\nu_{max}^{Nujol}$: 3250, 3100, 2600, 1760, 1670, 1620, 1580 cm$^{-1}$.

N.M.R. δppm (acetone-d$_6$+D$_2$O): 4.67–4.9 (2H, m), 5.17–5.6 (2H, m), 5.8–6.52 (1H, m), 7.0–8.33 (3H, m).

(4)(e) 2-(6-Formamidopyridin-2-yl)-2-propargyloxyiminoacetic acid (syn isomer), mp. 145° to 150° C. (dec.).

I.R. $\nu_{max}^{Nujol}$: 3350, 3250, 3100, 2600, 1755, 1685, 1620, 1580, 1510 cm$^{-1}$.

N.M.R. δppm (acetone-d$_6$+D$_2$O): 3.04 (1H, t, J=2 Hz), 4.88 (2H, d, J=2 Hz), 7.0-8.28 (3H, m).

(4)(f) 2-Butoxyimino-2-(6-formamidopyridin-2-yl)acetic acid (syn isomer), mp. 129° to 131° C. (dec.).

I.R. $\nu_{max}^{Nujol}$: 3150, 1755, 1670 cm$^{-1}$.

N.M.R. δppm (DMSO-d$_6$): 0.7-1.9 (7H, m), 4.20 (2H, t, J=6 Hz), 7.0-8.1 (3H, m), 10.7 (1H, broad d)

(4)(g) 2-Isobutoxyimino-2-(6-formamidopyridin-2-yl)acetic acid (syn isomer), mp. 153° to 155° C. (dec.).

I.R. $\nu_{max}^{Nujol}$: 3250, 3150, 1750, 1680, 1620, 1580 cm$^{-1}$.

N.M.R. δppm (acetone-d$_6$+D$_2$O): 0.96 (6H, d, J=6 Hz), 1.88-2.16 (1H, m), 4.0 (2H, d, J=6 Hz), 7.0-8.28 (3H, m).

(4)(h) 2-(6-Formamidopyridin-2-yl)-2-phenoxyiminoacetic acid (syn isomer), mp. 148° to 150° C. (dec.).

I.R. $\nu_{max}^{Nujol}$: 1730, 1660, 1560 cm$^{-1}$.

N.M.R. δ ppm (DMSO-d$_6$): 6.80-8.2 (8H, m), 10.80 (1H, d, J=8 Hz).

Preparation 6

(1) Methyl 6-formamido-3-pyridinecarboxylate, mp. 218° to 220° C. was obtained according to the similar manner to that of the Preparation 4-(1).

I.R. $\nu_{max}^{Nujol}$: 3100, 3020, 1710, 1605, 1540 cm$^{-1}$.

N.M.R. δ ppm (DMSO-d$_6$+D$_2$O): 3.84 (3H, s), 8.12-8.84 (3H, m).

(2) 2-Formamido-5-(2-methanesulfinyl-2-methylthioacetyl)pyridine, mp. 125° to 127° C. was obtained according to the similar manner to that of Preparation 4-(2).

I.R. $\nu_{max}^{Nujol}$: 3200, 1710, 1660, 1600, 1545 cm$^{-1}$.

(3) S-Methyl 2-(6-formamidopyridin-3-yl)thioglyoxylate, mp. 152° to 154° C. was obtained according to the similar manner to that of the Preparation 4-(3) by using acetic acid instead of acetic anhydride and formic acid.

I.R. $\nu_{max}^{Nujol}$: 3250, 3150, 3050, 1730, 1680, 1600, 1590, 1510 cm$^{-1}$.

N.M.R. δ ppm (acetone-d$_6$+D$_2$O): 2.47 (3H, s), 8.35-9.17 (3H, m).

(4) A mixture of S-methyl 2-(6-formamidopyridin-3-yl)thioglyoxylate (13 g.), methanol (50 ml.), 1 N aqueous solution of sodium hydroxide (58 ml.) and water (150 ml.) was stirred at ambient temperature for 30 minutes. To the mixture was added O-methylhydroxylamine hydrochloride (4.85 g.) and then stirred for an hour. The reaction mixture was adjusted to pH 7 with an aqueous solution of sodium bicarbonate, and the methanol was removed by distillation under reduced pressure. The remaining aqueous solution was washed with ethyl acetate and thereto was added ethyl acetate. The resultant mixture was adjusted to pH 2 with 10% hydrochloric acid and thereto was added sodium chloride, and the mixture was stirred for a while. The precipitates were collected by filtration washed with diisopropyl ether and then dried to give 2-(2-formamidopyridin-3-yl)-2-methoxyiminoacetic acid (syn isomer) (2.0 g.), mp. 159° to 161° C. (dec.).

I.R. $\nu_{max}^{Nujol}$: 1735, 1665, 1590, 1550 cm$^{-1}$.

N.M.R. δ ppm (DMSO-d$_6$): 4.00 (3H, s), 7.8-8.5 (3H, m), 10.87 (1H, d, J=6 Hz).

On the other hand, the ethyl acetate layer was separated from the filtrate and the remaining aqueous layer was further extracted with ethyl acetate. The ethyl acetate layers were combined together, dried over magnesium sulfate and then the solvent was distilled off to give powder of 2-(6-formamidopyridin-3-yl)-2-methoxyiminoacetic acid (a mixture of syn and anti isomers). Thus obtained powder was dissolved in an aqueous solution of sodium bicarbonate and then adjusted to pH 2 to 3 with 10% hydrochloric acid. The precipitates were collected by filtration and then dried to give 2-(6-formamidopyridin-3-yl)-2-methoxyiminoacetic acid (anti isomer) (1.45 g.), mp. 168° to 170° C. (dec.).

I.R. $\nu_{max}^{Nujol}$: 1705, 1605, 1535 cm$^{-1}$.

N.M.R. δ ppm (DMSO-d$_6$): 4.00 (3H, s), 7.8-8.5 (3H, m), 10.80 (1H, d, J=7 Hz).

Further, the mother liquor was adjusted to pH 3 to 4 with an aqueous solution of sodium bicarbonate. The resultant solution was washed with ethyl acetate, adjusted to pH 2 with 10% hydrochloric acid and then extracted with ethyl acetate. The extract was dried over magnesium sulfate and then the solvent was distilled off to give further 2-(6-formamidopyridin-3-yl)-2-methoxyiminoacetic acid (syn isomer) (2.5 g.).

Preparation 7

(1) Methyl 2-formamido-4-pyridine mp 196° to 197° C. was obtained according to the similar manner to that of the Preparation 4-(1).

I.R. $\nu_{max}^{Nujol}$: 3100, 1740, 1710, 1580, 1540 cm$^{-1}$.

N.M.R. δ ppm (DMSO-d$_6$): 3.92 (3H, s), 7.48-8.6 (3H, m).

(2) 2-Formamido-4-(2-methanesulfinyl-2-methylthioacetyl)pyridine, mp. 123° to 125° C. was obtained according to the similar manner to that of the Preparation 4-(2).

I.R. $\nu_{max}^{Nujol}$: 3150, 3050, 1690, 1610, 1565 cm$^{-1}$.

(3) S-Methyl 2-(2-formamidopyridin-4-yl)thioglyoxylate, mp. 165° to 167° C. was obtained according to the similar manner to that of the Preparation 4-(3) by using acetic acid instead of acetic anhydride and formic acid.

I.R. $\nu_{max}^{Nujol}$: 3250, 3100, 1710, 1680, 1610, 1565, 1520 cm$^{-1}$.

N.M.R. δ ppm (CDCl$_3$+D$_2$O): 2.48 (3H, s), 7.5-8.6 (3H, m).

(4) 2-(2-Formamidopyridin-4-yl)-2-methoxyiminoacetic acid (syn isomer), mp. 170° to 172° C. (dec.) was obtained according to the similar manner to that of the Preparation 4-(4) via 2-(2-formamidopyridin-4-yl)-glyoxylic acid.

I.R. $\nu_{max}^{Nujol}$: 2500, 1710, 1640, 1615, 1600, 1520 cm$^{-1}$.

N.M.R. δ ppm (DMSO-d$_6$+D$_2$O): 4.02 (3H, s), 7.0-8.6 (3H, m).

Preparation 8

(1) A mixture of ethyl 2-(4-amino-6-hydroxypyrimidin-2-yl)acetate (15.8 g.) and phosphoryl chloride (75 ml.) was stirred for 4 hours under heating at 80° to 90° C. The resultant solution was allowed to cool and phosphoryl chloride was distilled off. The remaining oily substance was poured into a mixture of ice-water (200 ml.) and ethyl acetate (200 ml.). The resultant mixture was neutralized with an aqueous solution of ammonia and extracted with ethyl acetate. The extract was washed with water, dried over magnesium sulfate and then the solvent was distilled off. The resultant residue was washed with diisopropyl ether and then dried to give pale brown crystals of ethyl 2-(4-amino-6-chloropyrimidin-2-yl)acetate (8.1 g.), mp. 127° to 128° C.

I.R. $\nu_{max}^{Nujol}$: 3250-3400, 1700, 1650, 1520-1580, 1320, 1160-1210, 860, 840 cm$^{-1}$.

(2) Ethyl 2-(6-chloro-4-formamidopyrimidin-2-yl)-acetate (oil) was obtained according to the similar manner to that of the Preparation 4-(1).

I.R. $\nu_{max}^{Film}$: 2800–3600, 1680–1730, 1560, 1140–1190, 1020 cm$^{-1}$.

N.M.R. δ ppm (CDCl$_3$): 1.30 (3H, t, J=8 Hz), 3.92 (2H, s), 4.23 (2H, q, J=8 Hz), 8.3–9.3 (1H, broad), 9.4–10.4 (2H, broad).

(3) To a solution of ethyl 2-(6-chloro-4-formamidopyrimidin-2-yl)acetate (2.3 g.) and sodium acetate (0.93 g.) in 80% ethanol (50 ml.) was added 10% palladium on carbon (0.2 g.), and the mixture was stirred under a hydrogen atmosphere for 8 hours at ambient temperature. The reaction mixture was filtered and the filtrate was concentrated. To the residue were added ethyl acetate and a small amount of water and the ethyl acetate layer was separated. The remaining aqueous layer was extracted with ethyl acetate. The ethyl acetate layers were combined together, washed with water and dried over magnesium sulfate and then the solvent was distilled off. Thus obtained oily substance (2.2 g.) was purified by column chromatography on silica gel (40 g.) using a mixture of benzene and ethyl acetate as an eluent to give a pale brown solid of ethyl 2-(4-formamidopyrimidin-2-yl)acetate (1.3 g.), mp. 80° to 93° C.

I.R. $\nu_{max}^{Nujol}$: 1710, 1670, 1530, 1310, 1170, 840 cm$^{-1}$.

N.M.R. δ ppm (CDCl$_3$): 1.23 (3H, t, J=8 Hz), 3.78 (2H, s), 4.33 (2H, q, J=8 Hz), 6.5–8.3 (1H, broad), 8.37 (1H, d, J=5 Hz), 9.15 (1H, broad s), 9.45 (1H, broad s).

(4) To a solution of ethyl 2-(4-formamidopyrimidin-2-yl)acetate (7.0 g.) in acetic acid (34 ml.) was added dropwise a solution of sodium nitrite (4.1 g.) in water (12 ml.) over a 15 minutes period with stirring at 10° C., and the stirring was continued at the same temperature for an hour and at ambient temperature for another an hour. After cooling the reaction mixture in an ice bath, water (50 ml.) was added thereto. The precipitates were collected by filtration and washed successively with water and diethyl ether and then dried to give a quantitative yield of a powder of ethyl 2-(4-formamidopyrimidin-2-yl)-2-hydroxyiminoacetate, mp. 164° to 180° C. (dec.).

N.M.R. δ ppm (DMSO-d$_6$): 1.30 (3H, t, J=8 Hz), 4.40 (2H, q, J=8 Hz), 7.5 (1H, broad), 8.73 (1H, d, J=6 Hz), 9.05 (1H, broad s).

(5) Ethyl 2-(4-formamidopyrimidin-2-yl)-2-hydroxyiminoacetate (7.0 g.) was dissolved in dioxane (200 ml.) under heating and the resultant solution was cooled to ambient temperature in an ice bath, and then thereto was added a solution of diazomethane in diethyl ether with stirring until complete consumption of the starting materials. The reaction mixture was concentrated to give a brown oil, which was purified by column chromatography on silica gel (140 g.) using benzene as an developing solvent and a mixture of benzene and ethyl acetate (3:1) as an eluent to give a pale brown semisolid of ethyl 2-(4-formamidopyrimidin-2-yl)-2-methoxyiminoacetate (4.4 g.).

I.R. $\nu_{max}^{Film}$: 3500–3600 (shoulder), 2900–3400, 1680–1740, 1560, 1500, 1250, 1020, 840 cm$^{-1}$.

N.M.R. δ ppm (CDCl$_3$): 1.40 (3H, t, J=8 Hz), 4.17 (3H, s), 4.47 (2H, q, J=8 Hz), 7.5–8.6 (1H, broad), 8.73 (1H, d, J=6 Hz), 8.9 (1H, broad).

(6) A mixture of ethyl 2-(4-formamidopyrimidin-2-yl)-2-methoxyiminoacetate (4.3 g.) and 10 N aqueous solution of sodium hydroxide (6.1 ml.) in ethanol (100 ml.) was stirred for 3 hours at ambient temperature. To the reaction mixture was gradually added concentrated hydrochloric acid with stirring, whereby said mixture was adjusted to pH 3. The precipitates were collected by filtration and washed successively with ethanol and diethyl ether and then dried to give white crystals of 2-(4-aminopyrimidin-2-yl)-2-methoxyiminoacetic acid.

I.R. ν(Nujol): 2500–3300, 1550–1650, 1240, 1000–1040 cm$^{-1}$.

N.M.R. δ ppm (D$_2$O-Na HCO$_3$): 4.05 (3H, s), 6.67 (1H, d, J=6 Hz), 8.18 (1H, d, J=6 Hz).

The filtrate and washings are combined together and the solvents were distilled off. The residue was pulverized in diethyl ether, collected by filtration and then dried to give further the same compound.

(7) 2-(4-Formamidopyrimidin-2-yl)-2-methoxyiminoacetic acid (brown powder), mp. 64° to 70° C. (dec.) was obtained according to the similar manner to that of the Preparation 4-(1).

N.M.R. δ ppm (DMSO-d$_6$): 4.02 (3H, s), 7.1–7.9 (1H, broad) 8.73 (1H, d, J=6 Hz), 8.9 (1H, broad).

Preparation 9

(1) A mixture of ethyl 2-(4-formamidopyrimidin-2-yl)acetate (2.95 g.), selenium dioxide (1.73 g.) in dimethylsulfoxide (30 ml.) was stirred under heating at 50° to 52° C. for an hour and at 70° to 72° C. for another 0.5 hours. The reaction mixture was cooled to ambient temperature and filtered, and then the filtered precipitates were washed with ethyl acetate. The filtrate and washings were combined together and concentrated to the volume of about 5 ml. under reduced pressure below 100° C. The residue was poured into water (50 ml.), and the mixture was stirred for 10 minutes. The resultant mixture was filtered and the filtered precipitates were washed with water. The filtrate and washings were combined together and adjusted to pH 7 with an aqueous solution of sodium bicarbonate. The mixture was washed with ethyl acetate and saturated with sodium chloride and then extracted with a mixture of ethyl acetate and ethanol (2:1). The extract was washed with a saturated aqueous solution of sodium chloride, dried over magnesium sulfate and then the solvent was distilled off to give a deep yellow oil of a mixture of ethyl 2-(4-formamidopyrimidin-2-yl)glyoxylate and its monohydrate, i.e. ethyl 2-(4-formamidopyrimidin-2-yl)-2,2-dihydroxyacetate (2.4 g.).

(2) A mixture of ethyl 2-(4-formamidopyrimidin-2-yl)acetate (2.95 g.), selenium dioxide (1.87 g.) and N,N-dimethyl formamide (15 ml.) was stirred for an hour under heating at 70° C. The reaction mixture was cooled to ambient temperature and filtered and then the filtered precipitates were washed with a small amount of N,N-dimethylformamide. The filtrate and washings were combined together and the solvent was distilled off. The residue was poured into water (60 ml.) and the resulting mixture was stirred for 10 minutes. The mixture was adjusted to pH 6 to 7 with an aqueous solution of sodium bicarbonate and filtered to separate insoluble substances, which were washed with water. The filtrate and washings were combined together and washed successively with diethyl ether and ethyl acetate. The aqueous mixture was saturated with sodium chloride and then extracted with a mixture of chloroform and ethanol (1:1) (60 ml.×4). The extract was dried over magnesium sulfate and the solvent was distilled off. The resulting oily substance (2.2 g.) was dissolved in ethyl acetate (10 ml.) and subjected to column chromatography on silica gel (15 g.) using ethyl acetate as an eluent. The eluates containing the desired compound were collected and then the solvent was distilled off. The resulting oily substance (1.5 g.) was dissolved in a small amount of ethyl acetate and then crystallized from diisopropyl ether to give pale yellow crystals of a mixture of ethyl 2-(4-formamidopyrimidin-2-yl)-glyoxylate and its monohydrate, i.e. ethyl 2-(4-formamidopyrimidin-2-yl)-2,2-dihydroxyacetate (0.6 g.), mp. 74° to 78° C.

I.R. $\nu_{max}^{Nujol}$: 3200–3400, 1755, 1690–1710, 1595, 1580, 1280, 1250, 1215, 1135, 1100, 1030, 850 cm$^{-1}$.

N.M.R. δ ppm (DMSO-d$_6$): 1.16 (1.8H, t, J=7 Hz), 1.26 (1.2H, t, J=7 Hz), 4.10 (1.2H, q, J=7 Hz), 4.42 (0.8H, q, J=7 Hz), 6.97 (1.2H, broad s), 7.0–7.8 (1H, m), 8.64 (0.6H, d, J=6 Hz), 8.90 (0.4H, d, J=6 Hz), 8.8–9.6 (1H, m), 11.15 (1H, broad s).

(3) A mixture of ethyl 2-(4-formamidopyrimidin-2-yl)glyoxylate and its monohydrate obtained in Preparation 6-(1) was dissolved in ethanol (30 ml.) and thereto was added dropwise 1 N ethanol solution of potassium hydroxide (11 ml.) under ice-cooling with stirring, and then stirring was continued for 2 hours at ambient temperature. The reaction mixture was filtered and the filtered precipitates were washed successively with a small amount of ethanol and diethyl ether and then dried to give a brown powder of potassium 2-(4-aminoprimidin-2-yl)-glyoxylate (0.4 g.). The filtrate and washings were combined together and concentrated to the volume of about 15 ml, and to the residue was added diethyl ether (20 ml.). The precipitates were collected by filtration and washed successively with a small amount of ethanol and diethyl ether to give further a pale brown powder of a mixture of potassium 2-(4-aminopyrimidin-2-yl)-glyoxylate and its monohydrate (0.8 g.).

Total yield: 1.2 g.

I.R. $\nu_{max}^{Nujol}$: 3380, 3200, 1715, 1665, 1600, 1245, 940, 750 cm$^{-1}$.

N.M.R. δppm (D$_2$O) : 6.54 (d, J = 6Hz) ⎫
6.74 (d, J = 6Hz) ⎬ (1H)
8.13 (d, J = 6Hz) ⎫
8.24 (d, J = 6Hz) ⎬ (1H)

(4) To a solution of O-methylhydroxylamine hydrochloride (0.25 g.) in methanol (6 ml.) was added a mixture of potassium 2-(4-aminopyrimidin-2-yl)glyoxylate and its monohydrate with stirring at ambient temperature, and the mixture was stirred for 4 hours. The reaction mixture was allowed to stand overnight at ambient temperature, filtered, and the filtered precipitates were washed with ethanol. After the filtrate and washings were combined together, the solvents were distilled off. The resultant oily substance was pulverized in acetone (15 ml.) and collected by filtration. Thus obtained powder was washed successively with acetone and diethyl ether and then dried to give a pale brown powder of 2-(4-aminopyrimidin-2-yl)-2-methoxyiminoacetic acid (syn isomer) (290 mg.).

I.R. $\nu_{max}^{Nujol}$: 3100–3400, 2500–2900, 1540–1660, 1250, 990–1040 cm$^{-1}$.

N.M.R. δ ppm (D$_2$O+NaHCO$_3$): 4.05 (3H, s), 6.63 (1H, d, J=6 Hz), 8.13 (1H, d, J=6 Hz).

Preparation 10

(1) Methyl 2-(2-formamido-6-chloropyrimidin-4-yl)acetate (crystal) was obtained according to the similar manner to that of the Preparation 4-(1).

I.R. $\nu_{max}^{Nujol}$: 3200, 3140, 1730, 1700, 1540–1580, 1500, 1420, 1380, 1350, 1270, 1240, 1140, 840, 770, 740 cm$^{-1}$.

(2) Methyl 2-(2-formamido-6-chloropyrimidin-4-yl)-2-hydroxyiminoacetate, mp. 110° to 112° C. was obtained according to the similar manner to that of the Preparation 8-(4).

I.R. $\nu_{max}^{Nujol}$: 3200, 1740, 1700, 1675, 1570, 1560, 1380, 1270, 1240, 1180, 1045, 860, 810, 750 cm$^{-1}$.

N.M.R. δ ppm (DMSO-d$_6$): 3.90 (3H, s), 7.57 (1H, s) 9.23 (1H, d, J=9 Hz), 11.40 (1H, d, J=9 Hz), 13.28 (1H, s).

(3) Methyl 2-(2-formamido-6-chloropyrimidin-4-yl)-2-methoxyiminoacetate (powder), mp. 165° to 172.5° C. was obtained according to the similar manner to that of the Preparation 8-(5).

I.R. $\nu_{max}^{Nujol}$: 3150, 1750, 1700, 1670, 1645, 1420, 1380, 1270, 1250, 1040, 955, 795, 735 cm$^{-1}$.

N.M.R. δ ppm (DMSO-d$_6$): 3.93 and 4.14 (6H, s), 7.59 (1H, s), 9.26 (1H, d, J=9 Hz), 11.50 (1H, d, J=9 Hz).

(4) 2-(2-Amino-6-chloropyrimidin-4-yl)-2-methoxyiminoacetic acid (powder) was obtained according to the similar manner to that of the Preparation 8-(6).

I.R. $\nu_{max}^{Nujol}$: 3350, 3200, 1695–1740, 1660, 1365, 1030 cm$^{-1}$.

N.M.R. δppm (DMSO-d$_6$ + D$_2$O) : 3.80 (3H, s),
6.16 (s) ⎫
6.77 (s) ⎬ (1H)

(5) 2-(2-Formamido-6-chloropyrimidin-4-yl)-2-methoxyiminoacetic acid (powder), mp. 138° to 142° C. (dec.) was obtained according to the similar manner to that of Preparation 4-(1).

I.R. $\nu_{max}^{Nujol}$: 3400, 3325, 3200, 1740, 1695, 1670, 1550, 1385, 1250, 1040, 820 cm$^{-1}$.

N.M.R. δppm (DMSO-d $_6$) : 4.05 (3H, s)
6.87 (s) ⎫
6.93 (s) ⎬ (1H)
9.38 (1H, d, J = 9Hz)
11.11 (1H, d, J = 9Hz)

Preparation 11

(1) A 15% n-hexane solution (636 g.) of n-butyllithium was added to a solution of 2-amino-6-methylpyridin (64.8 g.) in tetrahydrofuran (500 ml.) at −20° to −30° C. over one hour, and stirred at −8° to −10° C. for 30 minutes. To the solution was added trimethylsilylchloride (161.7 g.) at −15° to −5° C. over 40 minutes, and the resultant solution was stirred at room temperature overnight. The solution was filtered through by a column packed with silica gel (180 g.), washed with tetrahydrofuran and then the filtrate was concentrated under reduced pressure. The residue was purified by fractional distillation to give a 2-[N,N-bis(-trimethylsilyl)amino]-6-methylpyridine (117.6 g.), b.p. 95° to 97° C./5–6 mmHg.

N.M.R. δ ppm (CCl$_4$): 0.13 (18H, s), 2.35 (3H, s), 6.43 (1H, d, J=8 Hz), 6.60 (1H, d, J=8 Hz), 7.25 (1H, t, J=8 Hz).

(2) A 15% n-hexane solution (338.6 g.) of n-butyllithium was dropwise added to a solution of 2-[N,N-bis(-trimethylsilyl)amino]-6-methylpyridine (100 g.) in anhydrous tetrahydrofuran (300 ml.) at −20° to −30° C. over one hour and the solution was stirred at 20° to 23° C. for one hour. The resultant solution was added in small portions to crushed dry ice (1 kg.) under stirring, and stirred till a room temperature. After removing tetrahydrofuran from the solution under reduced pressure, absolute ethanol (1 l.) was added to the residue. 30% Ethanol solution (660 ml.) of hydrochloric acid was dropwise added to the solution at −5° to −10° C., and further hydrogen chloride gas was bubbled at 0° to 5° C. for 30 minutes and then the solution was stirred at 10° C. overnight. After removing ethanol from the resultant solution, the residue was dissolved in water, and washed with ethyl acetate 3 times. The solution was adjusted to pH 7 to 8 with sodium bicarbonate and extracted with ethyl acetate. The ethyl acetate extract was washed with a saturated aqueous solution of sodium chloride, dried and concentrated under reduced pressure to give the crude product (54 g.). The product was purified by column chromatography on silica gel (1 kg.) with an eluent (ethyl acetate+benzene) to give ethyl 2-(6-aminopyridin-2-yl)acetate (30.2 g.), mp. 66° to 68° C.

I.R. $\nu_{max}^{Nujol}$: 3430, 3340, 3200, 1730, 1645, 1480, 1190 cm$^{-1}$.

N.M.R. δ ppm (CDCl$_3$): 1.25 (3H, t, J=6 Hz), 3.67 (2H, s), 4.20 (2H, q, J=6 Hz), 5.33 (2H, broad s), 6.43 (1H, d, J=8 Hz), 6.62 (1H, d, J=8 Hz), 7.40 (1H, t, J=8 Hz).

(3) Ethyl 2-(6-formamidopyridin-2-yl)acetate, mp. 35° to 38° C. was obtained according to the similar manner to that of the Preparation 4-(1).

I.R. $\nu_{max}^{Nujol}$: 3250, 3100, 1738, 1690, 1580, 1460, 1305, 1277 cm$^{-1}$.

N.M.R. δ ppm (DMSO-d$_6$): 1.17 (3H, t, J=8 Hz), 3.75 (2H, s), 4.08 (2H, q, J=8 Hz), 6.85 (0.5H, broad d, J=8 Hz), 7.95 (0.5H, broad s), 7.08 (1H, d, J=8 Hz), 7.73 (1H, t, J=8 Hz), 8.33 (0.5H, broad s), 9.25 (0.5H, broad d), 10.58 (1H, broad s).

(4) To a solution of ethyl 2-(6-formamidopyridin-2-yl)acetate (26 g.) in dioxane (260 ml.) was added selenium dioxide (16.65 g.) in small portions at 85° to 90° C. over one hour and stirred at the same temperature for one hour. After cooling the resultant solution the dioxane layer was separated and concentrated under reduced pressure and then the residue was dissolved in ethyl acetate. The solution was washed with water, dried over magnesium sulfate and treated with activated charcoal and then concentrated under reduced pressure. The residue was triturated with diethyl ether to give ethyl 2-(6-formamidopyridin-2-yl)glyoxylate (14.3 g.), mp. 124° to 126° C.

I.R. $\nu_{max}^{Nujol}$: 3220, 3100, 1737, 1720, 1690, 1273, 1233 cm$^{-1}$.

N.M.R. δ ppm (DMSO-d$_6$): 1.34 (3H, t, J=8 Hz), 4.44 (2H, q, J=8 Hz), 7.33 (0.65H, broad s), 7.8–8.2 (0.35H), 7.84 (1H, d, J=8 Hz), 8.09 (1H, t, J=8 Hz), 8.44 (0.35H, broad s), 9.22 (0.65H, broad s), 10.85 (1H, broad s).

(5) 2-(6-Formamidopyridin-2-yl)-2-methoxyiminoacetic acid (syn isomer), mp. 170° to 171° C. (dec.) was obtained according to the similar manner to that of the Preparation 4-(4) via 2-(6-formamidopyridin-2-yl)-glyoxylic acid.

I.R. $\nu_{max}^{Nujol}$: 3230, 3132, 1745, 1680, 1575, 1450, 1320, 1208, 1032 cm$^{-1}$.

N.M.R. δ ppm (DMSO-d$_6$): 3.70 (3H, s), 6.90 (0.6H, broad d), 7.9 (0.4H, broad s), 7.10 (1H, d, J=8 Hz), 7.75 (1H, t, J=8 Hz), 8.38 (0.4H, broad s), 9.25 (0.6H, broad d), 10.58 (1H, broad d).

(6) A mixture of 2-(6-formamidopyridin-2-yl)-2-methoxyiminoacetic acid (syn isomer) (5.0 g.) and concentrated hydrochloric acid (2.34 g.) in methanol (50 ml.) was stirred for 40 minutes at ambient temperature. After the removal of methanol from the reaction mixture under reduced pressure, the residue was pulverized in diethyl ether, collected by filtration and then dried to give a pale brown powder of 2-(6-aminopyridin-2-yl)-2-methoxyiminoacetic acid hydrochloride (syn isomer) (5.2 g.)

N.M.R. δ ppm (DMSO-d$_6$+D$_2$O): 4.10 (3H, s), 6.84 (1H, d, J=7 Hz), 7.23 (1H, d, J=10 Hz), 7.99 (1H, dd, J=7 Hz, 10 Hz).

(7) To a mixture of 2-(6-aminopyridin-2yl)-2-methoxyiminoacetic acid hydrochloride (syn isomer), acetic acid (350 ml.) and water (10 ml.) was introduced chloride gas for 1.5 hours. After the removal of the excess of the chlorine gas by bubbling air into the reaction mixture, the solvent was distilled off. The residue was pulverized in diethyl ether and collected by filtration. After the addition of water and ethyl acetate to the resultant powder (9.8 g.), the aqueous layer was separated and washed with ethyl acetate. The ethyl acetate layer and washings were combined together, and further extracted with water. The aqueous layers were combined together and adjusted to pH 4 with 1 N aqueous solution of sodium hydroxide, and then the solvent was distilled off under reduced pressure. The remaining water in the residue was azeotropically removed with benzene three times to yield brownish powder which was dried in a desiccator to give 2-(6-amino-3-chloropyridin-2-yl)-2-methoxyiminoacetic acid (syn isomer) (3.27 g.).

N.M.R. δ ppm (DMSO-d$_6$+D$_2$O): 3.81 (3H, s), 6.50 (1H, d, J=9 Hz), 7.48 (1H, d, J=9 Hz).

Further the remaining ethyl acetate layer was dried over magnesium sulfate and the solvent was distilled off. The residue was washed with diethyl ether and then dried to give 2-(6-amino-3,5-dichloropyridin-2-yl)-2-methoxyiminoacetic acid (syn isomer) (2.4 g.), mp. 139° to 144° C.

N.M.R. δ ppm (DMSO-d$_6$): 3.96 (3H, s), 6.2–7.1 (2H, broad), 7.83 (1H, s).

(8) (a) 2-(3-Chloro-6-formamidopyridin-2-yl)-2-methoxyiminoacetic acid (syn isomer) (powder), mp. 151° to 154° C. was obtained according to the similar manner to that of the Preparation 4-(1).

I.R. $\nu_{max}^{Nujol}$: 3200, 1740, 1680, 1580, 1290, 1250, 1140, 1050, 840 cm$^{-1}$.

(8) (b) 2-(3,5-Dichloro-6-formamidopyridin-2-yl)-2-methoxyiminoacetic acid (syn isomer) (powder). mp. 164° to 165° C. was obtained according to the similar manner to that of the Preparation 4-(1).

I.R. $\nu_{max}^{Nujol}$: 3250, 2300–2600, 1712, 1565, 1410, 1250, 1035 cm$^{-1}$.

N.M.R. δ ppm (DMSO): 4.02 (3H, s), 8.29 (1H, s), 9.05 (1H, d, J=10 Hz), 10.77 (1H, d, J=10 Hz).

Preparation 12

To a solution of ethyl 3-ethoxyacrylimidate hydrochloride (4.0 g) and 1-ethoxycarbonylformamidine hydrobromide (4.4 g) in methanol (110 ml) was added dropwise a solution of sodium metal (1 g) in methanol (110 ml) at 0° C. The reaction mixture was stirred for an hour at 0° to 5° C. and for additional 4 hours at ambient temperature. The solution was evaporated to dryness and the residue was dissolved in a mixture of ethyl acetate and an aqueous solution of sodium chloride. The organic layer was separated out and the aqueous layer was extracted with ethyl acetate five times. All organic layers were combined, dried over anhydrous magnesium sulfate and evaporated to dryness. The residue was triturated with diethyl ether to give methyl 4-aminopyrimidine-2-carboxylate (1.33 g), which was recrystallized from ethyl acetate, mp. 140°–142.5° C.

I.R. $\nu_{max}^{Nujol}$: 3450, 3300, 3180, 1730, 1630, 1585, 1540 cm$^{-1}$.

N.M.R. $\delta$ ppm (DMSO-d$_6$): 3.81 (3H, S), 6.54 (1H, d, J=6 Hz), 7.23 (2H, S), 8.16 (1H, d, J=6 Hz).

Preparation 13

(1) To a solution of 2-chloroacrylonitrile (437 mg) and 1-ethoxycarbonylformamidine hydrobromide (985 mg) in ethanol (5 ml) was added dropwise triethylamine (1.01 g) at 0° C. The reaction mixture was stirred for 4 hours at ambient temperature and evaporated to dryness. The residue was dissolved in a mixture of ethyl acetate and water, and extracted with ethyl acetate three times. The combined extracts were dried over anhydrous magnesium sulfate and evaporated to dryness. The residue was triturated with diethyl ether to give ethyl 4-aminopyrimidine-2-carboxylate (480 mg), which was recrystallized from a mixture of ethyl acetate and benzene, mp. 101°–104° C.

I.R. $\nu_{max}^{Nujol}$: 3450, 3300, 3180, 1730, 1630, 1580, 1540 cm$^{-1}$.

N.M.R. $\delta$ ppm (DMSO-d$_6$): 1.30 (3H, t, J=7 Hz), 4.30 (2H, q, J=7 Hz), 6.60 (1H, d, J=6 Hz), 7.31 (2H, S), 8.20 (1H, d, J=6 Hz).

The following compound was obtained according to the similar manner to that of Preparation 13-(1) by using triethylamine or sodium carbonate as a base.

(2) Methyl 4-aminopyrimidine-2-carboxylate.

I.R. $\nu_{max}^{Nujol}$: 3450, 3300, 3180, 1730, 1630, 1585, 1540 cm$^{-1}$.

Preparation 14

(1) A mixture of formic acid (100 g) and acetic anhydride (204 g) was stirred for half an hour at ambient temperature. To the solution was added ethyl 4-aminopyrimidine-2-carboxylate (30 g) and the mixture was stirred for 1.5 hours at 70° to 75° C. and then evaporated to dryness. The residue was triturated with ethanol, collected by filtration and washed with ethanol to give ethyl 4-formamidopyrimidine-2-carboxylate (20.0 g), mp 205°–206° C.

I.R. $\nu_{max}^{Nujol}$: 3100, 1720, 1630, 1570, 1520 cm$^{-1}$.

N.M.R. $\delta$ ppm (DMSO-d$_6$): 1.37 (3H, t, J=7 Hz), 4.40 (2H, q, J=7 Hz), 7.73 (1H, broad s), 8.83 (1H, d, J=4 Hz), 9.00 (1H, broad s), 11.40 (1H, broad s).

The following compound was obtained according to the similar manner to that of Preparation 14-(1).

(2) Methyl 4-formamidopyrimidine-2-carboxylate, mp. 234°–236° C.

I.R. $\nu_{max}^{Nujol}$: 3100, 1735, 1710, 1640, 1570, 1530, 1510 cm$^{-1}$.

N.M.R. $\delta$ ppm (DMSO-d$_6$): 3.93 (3H, s), 7.73 (1H, broad s), 8.82 (1H, d, J=5 Hz), 9.00 (1H, broad s), 11.40 (1H, broad s).

Preparation 15

(1) To a solution of methyl 4-formamidopyrimidine-2-carboxylate (1.3 g) and methyl methylthiomethyl sulfoxide (0.89 g) in N,N-dimethylformamide (10 ml) was added 50% sodium hydride (1.0 g) at 10° C. under stirring and the stirring was continued for 1.5 hours at ambient temperature. The mixture was cooled in an ice bath and thereto was added methylene chloride (30 ml).

The precipitate which was collected by filtration was added portionwise to a mixture of methylene chloride (50 ml), ice water and concentrated hydrochloric acid (2.1 ml) under stirring. The methylene chloride layer was separated out and the aqueous layer was extracted with methylene chloride. The combined extracts were dried over anhydrous magnesium sulfate and evaporated to dryness. The residue was triturated with diethyl ether, filtered and washed with diethyl ether to give 4-formamido-2-(2-methanesulfinyl-2-methylthioacetyl) pyrimidine (1.2 g).

I.R. $\nu_{max}^{Nujol}$: 1690, 1560, 1450, 1370 cm$^{-1}$.

N.M.R. $\delta$ppm
(DMSO-d$_6$): 2.23 (s), 2.30 (s), 2.73 (s), 2.93 (s) } (3H,)
5.95 (s), 6.07 (s) } (3H,)
(1H),
7.67 (1H, broad s), 8.92 (1H, d, J = 5Hz), 9.17 (1H, broad s), 11.40 (1H, broad s)

The same compound as the object compound of Preparation 15-(1) was obtained from the following compound according to the similar manner thereto.

(2) Ethyl 4-formamidopyrimidine-2-carboxylate.

Preparation 16

A mixture of formic acid (4.82 g) and acetic anhydride (9.7 g) was stirred for half an hour at ambient temperature.

To the solution was added 4-formamido-2-(2-methanesulfinyl-2-methylthioacetyl)pyrimidine (2.6 g) and the mixture was stirred for 1.5 hours at 50° C. and then for an hour with an addition of sodium periodate (610 mg) at the same temperature. The mixture was evaporated to dryness and the residue was dissolved in a mixture of ethyl acetate (50 ml) and an aqueous solution (20 ml) of sodium chloride. The organic layer was separated out and the aqueous layer was extracted with ethyl acetate three times. The combined organic layers were dried over anhydrous magnesium sulfate and evaporated to dryness. The residue (2.0 g) was subjected to column chromatography over silica gel (13 g) using a mixture of ethyl acetate and benzene (1:1 by volume) as an eluent. The fractions containing a desired compound were collected, evaporated to dryness and crystallized from a small amount of ethyl acetate to give pure product of S-methyl 4-formamidopyrimidine-2-thioglyoxylate (840 mg), mp 112°–114° C.

I.R. $\nu_{max}^{Nujol}$: 3480, 3380, 1715, 1680, 1585 cm$^{-1}$.

N.M.R. δ ppm (DMSO-d$_6$): 2.17 (3H, s), 7.20 (1H, broad s), 8.12 (1H, d, J=6 Hz), 9.17 (1H, broad s), 11.08 (1H, d, J=7 Hz).

Preparation 17

(1) To a suspension of S-methyl 4-formamidopyrimidine-2-thioglyoxylate (3.0 g) in water (26 ml) was added dropwise 1 N aqueous solution (12 ml) of sodium hydroxide at ambient temperature and the mixture was stirred for half an hour at the same temperature.

To the solution was added an aqueous solution of ethoxyamine prepared by ethoxyamine hydrochloride (1.3 g), water (10 ml) and sodium bicarbonate (1.12 g). The reaction mixture was stirred for half an hour at ambient temperature and adjusted to pH 4 with 1 N hydrochloric acid (1.5 ml). The solution was stirred for 10 minutes at ambient temperature and adjusted to pH 3 with 1 N hydrochloric acid and then washed with ethyl acetate. The aqueous layer was salted out, adjusted to pH 1 with 10% hydrochloric acid and extracted with ethyl acetate. The extract was dried over magnesium sulfate and evaporated to dryness. The crystallized residue was washed with n-hexane to give 2-ethoxyimino-2-(4-formamidopyrimidin-2-yl) acetic acid (syn isomer) (2.22 g), mp. 130°–135° C. (dec).

I.R. $\nu_{max}^{Nujol}$: 3250, 1720, 1630, 1605, 1570 cm$^{-1}$.

N.M.R. δ ppm (DMSO-d$_6$): 1.28 (3H, t, J=7 Hz), 4.32 (2H, q, J=7 Hz), 7.4–7.7 (1H, m), 8.72 (1H, d, J=6 Hz), 8.8–9.1 (1H, m), 11.37 (1H, d, J=6Hz).

The following compounds were obtained according to the similar manner to that of Preparation 17-(1).

(2) 2-(4-Formamidopyrimidin-2-yl)-2-methoxyiminoacetic acid (syn isomer), mp. 165°–166° C. (dec.).

I.R. $\nu_{max}^{Nujol}$: 3400, 3250, 3150, 1740, 1700, 1570 cm$^{-1}$.

N.M.R. δ ppm (DMSO-d$_6$): 4.00 (3H, s), 7.53 (1H, broad s), 8.72 (1H, d, J=6 Hz), 8.87 (1H, broad s), 11.23 (1H, d, J=6 Hz).

(3) 2-(4-Formamidopyrimidin-2-yl)-2-propoxyiminoacetic acid (syn isomer), mp 145°–148° C. (dec.).

I.R. $\nu_{max}^{Nujol}$: 3150, 3100, 3050, 1750, 1690, 1615, 1570, 1540 cm$^{-1}$.

(4) 2-Allyloxyimino-2-(4-formamidopyrimidin-2-yl) acetic acid (syn isomer), mp 120°–122° C. (dec.).

I.R. $\nu_{max}^{Nujol}$: 3250, 3100, 1710, 1630, 1570, 1515 cm$^{-1}$.

(5) 2-Benzyloxyimino-2-(4-formamidopyrimidin-2-yl) acetic acid (syn isomer), mp 75°–77° C.

I.R. $\nu_{max}^{Nujol}$: 3250, 3050, 1720, 1630, 1570 cm$^{-1}$.

Preparation 18

A mixture of ethyl 2-(6-chloro-4-formamidopyrimidin-2-yl) acetate (24.3 g) and selenium dioxide (16.65 g) in N,N-dimethylformamide (243 ml) was stirred for an hour at 70° to 75° C. The precipitated solid was filtered off, and the filtrate was concentrated in vacuo. The residue was dissolved in ethyl acetate (500 ml), washed with water and an aqueous solution of sodium chloride, dried over anhydrous magnesium sulfate and evaporated to dryness. The residue was triturated with diisopropyl ether to give a powder of ethyl 6-chloro-4-formamidopyrimidin-2-ylglyoxylate (17.74 g).

This product (1 g) was recrystallized from ethyl acetate (10 ml) to afford the purified product (570 mg), mp 114°–117° C.

I.R. $\nu_{max}^{Nujol}$: 3400, 3230–3100, 1760, 1720–1680, 1580–1550, 1250, 1200, 850, 730 cm$^{-1}$.

Preparation 19

To a mixture of ethyl 6-chloro-4-formamidopyrimidin-2-ylglyoxylate (10.6 g) and methoxyamine hydrochloride (3.34 g) in ethanol (200 ml) was added an aqueous solution (60 ml) of sodium bicarbonate (3.36 g) and the mixture was stirred for 2 hours at ambient temperature. After evaporation of the solvent, the residue was dissolved in ethyl acetate. The solution was washed with water, dried over anhydrous magnesium sulfate and evaporated to give oily product (10.8 g).

This product was subjected to column chromatography over silica gel (118 g) using benzene as an eluent. The fractions contained a desired compound were collected, and evaporated, and the resultant oily product (5.6 g) was crystallized from diethyl ether to give ethyl 2-(6-chloro-4-formamidopyrimidin-2-yl)-2-methoxyiminoacetic acid (syn isomer), mp. 116°–119° C.

I.R. $\nu_{max}^{Nujol}$: 3400, 1750, 1725, 1665, 1495, 1270, 1030 cm$^{-1}$.

N.M.R. δ ppm (CDCl$_3$): 1.35 (3H, t, J=7 Hz), 4.09 (3H, s), 4.40 (2H, q, J=7 Hz), 6.5–8.3 (1H, broad), 8.3–9.0 (1H, broad), 9.2 (1H, broad s).

Preparation 20

A mixture of ethyl 2-(4-formamidopyrimidine-2-yl) acetate (50.0 g) and selenium dioxide (31.87 g) in N,N-dimethylformamide (240 ml) was stirred for an hour at 70° to 75° C. and cooled to ambient temperature. The precipitated solid was filtered off and the filtrate was evaporated in vacuo to give an oily product. The oil was added to water (750 ml) under stirring, adjusting to ph7 with an aqueous solution of sodium bicarbonate. The precipitated yellow substance was filtered off and washed with water. The filtrate and washings were combined and thereto was added methoxyamine hydrochloride (19.95 g). The mixture was adjusted to pH4 with an aqueous solution of sodium bicarbonate and stirred for 3 hours at ambient temperature. The aqueous reaction mixture was extracted with ethyl acetate and the extract was washed with an aqueous solution of sodium chloride, dried over anhydrous magnesium sulfate and evaporated to give ethyl 2-(4-formamidopyrimidin-2-yl)-2-methoxyiminoacetate (syn isomer) (31 g) as a brownish oil.

N.M.R. δ ppm (CDCl$_3$): 1.36 (3H, t, J=7 Hz), 4.12 (3H, s), 4.42 (2H, q, J=7 Hz), 6.5–8.2 (1H, broad), 8.66 (1H, d, J=6 Hz), 8.8–10.0 (2H, broad).

Preparation 21

(1) To a solution of ethyl 2-(4-formamidopyrimidin-2-yl)-2-methoxyiminoacetic acid (syn isomer) (30.8 g) in ethanol (308 ml) was added 1 N alcoholic solution (550 ml) of potassium hydroxide and the mixture was stirred for 3.5 hours at ambient temperature. The reaction mixture was cooled in an ice bath and adjusted to pH3 with concentrated hydrochloric acid (53 ml). The resultant solid was filtered and washed with ethanol (60 ml), water (100 ml), acetone (100 ml) to give a crude product (28.8 g). This product (1 g) was recrystallized from water (10 ml) to give a purified product of 2-(4-aminopyrimidin-2-yl)-2-methoxyiminoacetic acid (dihydrate, syn isomer) (0.4 g), mp. 178°–183° C. (dec.).

The following compound was obtained according to the similar manner to that of Preparation (21-(1).

(2) 2-(4-Amino-6-chloropyrimidin-2-yl)-2-methoxyiminoacetic acid (syn isomer).

I.R. $\nu_{max}^{Nujol}$: 3480, 3380, 3200, 1640, 1610–1580, 1530, 1040, 720 cm$^{-1}$.

N.M.R. δ ppm (D$_2$O): 4.10 (3H, s), 6.76 (1H, s).

Preparation 22

To a solution of ethyl 2-(4-chloro-6-formamidopyrimidin-2-yl)-2-methoxyiminoacetate (syn isomer) (17 g) in ethanol (255 ml) was added dropwise phosphoryl chloride (14.7 g) under cooling in an ice bath. The mixture was stirred for 1.5 hours at ambient temperature and evaporated to dryness.

The residue was dissolved in a mixture of ethyl acetate and water and adjusted to pH7 with an aqueous solution of sodium bicarbonate. The organic layer was separated out, dried over anhydrous magnesium sulate and evaporated to dryness. The residue was triturated with n-hexane to give ethyl 2-(4-amino-6-chloropyrimidin-2-yl)-2-methoxyiminoacetate (syn isomer) (9.99 g), mp 136°–142° C.

I.R. $\nu_{max}^{KBr}$: 3500, 3380, 3200, 1735, 1640, 1575, 1535, 1040 cm$^{-1}$.

N.M.R. δ ppm (DMSO-d$_6$): 1.30 (3H, t, J=7 Hz), 4.03 (3H, s), 4.30 (2H, q, J=7 Hz), 6.53 (1H, s), 7.5 (2H, broad s).

Preparation 23

(1) To a solution of ethyl 2-(4-amino-6-chloropyrimidin-2-yl) acetate (21.5 g) in methanol (200 ml) was added a solution of sodium metal (7.25 g) in methanol (130 ml) and the mixture was refluxed for 3.5 hours. The reaction mixture was cooled in an ice-salt bath and saturated with dry hydrogen chloride and then allowed to stand overnight at ambient temperature. The mixture was evaporated to dryness and the residue was dissolved in a mixture of ethyl acetate and a cold aqueous solution of sodium bicarbonate. The organic layer was separated out, washed with water, dried over anhydrous magnesium sulfate and and evaporated to give methyl 2-(4-amino-6-methoxypyrimidin-2-yl) acetate (14.2 g), mp 91°–94° C.

I.R. $\nu_{max}^{Nujol}$: 3480, 3390, 3210, 1738, 1660, 1600 cm$^{-1}$.

N.M.R. δ ppm (DMSO-6): 3.66 (5H, s), 3.82 (3H, s), 5.68 (1H, s), 6.66 (2H, broad s).

(2) To a solution of thiophenol (2.55 g) in N,N-dimethylformamide (20 ml) was added 50% sodium hydride (1.1 g) under cooling in an ice bath and the mixture was stirred for 20 minutes at 0° C. to 5° C. To the mixture was added ethyl 2-(4-amino-6-chloropyrimidin-2-yl)-2-methoxyiminoacetate (2.0 g) and the mixture was stirred for 6 hours at ambient temperature. The resultant mixture was poured into cold water, adjusted to pH7 with diluted hydrochloric acid and extracted with ethyl acetate. The extract was washed with water, dried over anhydrous magnesium sulfate and evaporated to dryness. The residue was subjected to column chromatography on silica gel (50 g) using a mixture of chloroform and ethyl acetate (3:1 by valume) as an eluent. The fractions containing the object product were collected and evaporated to give ethyl 2-(4-amino-6-phenylthiopyrimidin-2-yl)-2-methoxyiminoacetate (syn isomer) (460 mg), mp 154°–156° C.

I.R. $\nu_{max}^{Nujol}$: 3450, 3280, 3160, 1720, 1620, 1550, 1520, 1300, 1040, 1025, 700 cm$^{-1}$.

N.M.R. δ ppm (CDCl$_3$): 1.34 (3H, t, J=7 Hz), 4.05 (3H, s), 4.27 (2H, q, J=7 Hz) 5.2 (2H, broad s), 5.84 (1H, s), 7.2–7.7 (5H, m).

Preparation 24

Methyl 2-(4-formamido-6-methoxypyridin-2-yl) acetate (13.9 g) was obtained by reacting methyl 2-(4-amino-6-methoxypyrimidin-2-yl) acetate (14 g) with formic accid (14.7 g) and acetic anhydride (30.4 g) accarding to the similar manner to that of Preparation 14-(1), mp 61°–63° C.

N.M.R.δ ppm (DMSO-d6): 3.73 (3H, s), 3.87 (2H, s), 3.96 (3H, s), 6.1–7.8 (1H, broad), 8.1–9.8 (1H, broad), 10.87 (1H, d, J=6 Hz).

Preparation 25

Methyl 2-(4-formamido-6-methoxypyrimidin-2-yl)-2-methoxyiminoacetate (syn isomer) (12.47 g) was obtained by reacting methyl 2-(4-formamido-6-methoxypyrimidin-2-yl) acetate (12.24 g) with selenium dioxide (6.94 g) and then methoxyamine hydrochloride (4.51 g) according to the semilar manner to that of Preparation 20, I.R. $\nu_{max}^{Film}$: 3300, 1750, 1720, 1660, 1590, 1565, 1210, 1035 cm$^{-1}$.

Preparation 26

(1) 2-(4-Amino-6-methoxypyrimidin-2-yl)-2-methoxyiminoacetic acid (syn isomer) (8.22 g) was obtained by reacting methyl 2-(4-formamido-6-methoxypyrimidin-2-yl)-2-methoxyiminoacetate (syn isomer) (12.0 g) with 1 N ethanolic solution (187 ml) of potassium hydroxide according to the similar manner to that of Preparation 21, mp 127°–129° C. (dec.).

I.R. $\nu_{max}^{Nujol}$: 3420, 3380, 1650, 1615, 1590, 1250, 1050, 1025 cm$^{-1}$.

N.M.R. δ ppm (DMSO-d$_6$+D$_2$O): 3.78 (3H, s), 3.95 (3H, s), 5.78 (1H, s).

(2) 2-(4-Amino-6-phenylthiopyrimidin-2-yl)-2-methoxyiminoacetic acid (syn isomer) (130 mg) was obtained by reacting ethyl 2-(4-amino-6-phenylthiopyrimidin-2-yl)-2-methoxyimino-acetate (syn isomer) (247 mg) with 1 N aqueous solution (1.8 ml) of sodium hydroxide according to the similar manner to that of Preparation 21, mp 136°–138° C. (dec.).

I.R. $\nu_{max}^{Nujol}$: 3300, 1650, 1600, 1560, 1150, 1040, 750 cm$^{-1}$.

Preparation 27

To a suspension of S-methyl (4-formamidopyrimidin-2-yl)-thioglyoxylate (6.7 g) in water (60 ml) was added dropwise 1 N aqueous solution of sodium hydroxide (26.8 ml) over a period of 15 minutes with stirring, and the stirring was continued at ambient temperature for 20 minutes.

On the other hand, an ethanolic solution (50 ml) of N-phenoxyphthalimide (9.26 g) and hydrazine monohydrate (1.84 g) was refluxed under heating for 5 minutes and the precipitates were removed by filtration. The resultant solution was added to the aqueous solution obtained above, followed by stirring for 5 minutes. After adjusting to pH 3 to 4 with 6 N hydrochloric acid, the stirring was continued at ambient temperature for additional 3 hours. The ethanol was removed by evaporation from the reaction mixture, and the remaining aqueous solution was adjusted to pH 7 to 8 with 5% aqueous solution of sodium bicarbonate and then washed with ethyl acetate. To the aqueous solution was added ethyl acetate and then adjusted to pH 1 to 2 with hydrochloric acid. The separated ethyl acetate layer was washed with water, dried over magnesium sulfate and evaporated to dryness. The residue was pulverized with diisopropyl ether to give a brownish powder (2.2 g) of 2-(4-formamidopyrimidin-2-yl)-2-phenoxyiminoacetic acid (syn isomer), mp 131°–133° C. (dec.).

I.R. $\nu_{max}^{Nujol}$: 3150, 1740, 1680, 1660, 1575, 1540, 1440, 1310, 1205, 980, 760 cm$^{-1}$.

N.M.R. δppm (DMSO-d6): 7.1–7.9 (5H, m), 8.15 (1H, m), 8.97 (1H, d, J=6 Hz), 9.23 (1H, m), 11.57 (1H, d, J=6 Hz).

What we claim is:

1. A compound of the formula:

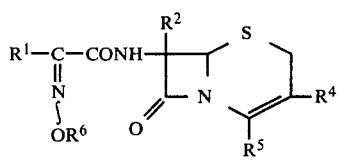

wherein $R^1$ is a group of the formula

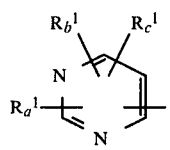

in which $R_a^1$ is amino or acylamino located at the 2, 4 or 6-position of the ring, acyl being selected from the group consisting of lower alkanoyl, halo (lower) alkanoyl, and lower alkoxycarbonyl, $R_b^1$ and $R_c^1$ are each hydrogen, halogen, lower alkoxy, phenylthio, tolylthio, xylylthio, mesitylthio or naphthylthio, $R^2$ is hydrogen or lower alkoxy $R^4$ is substituted or unsubstituted heterocyclic-thiomethyl, the heterocyclic moiety of $R^4$ being a 5 to 6-membered monocyclic group or an unsaturated bicyclic condensed heterocyclic group whose rings have 5 or 6 members, the ring atoms of said heterocyclic group being C and at least one hetero atom selected from N, O and S, the heterocyclic to thiomethyl bond being a C—S bond, the substituent in said substituted heterocyclicthiomethyl group being located in the heterocyclic moiety, and being selected from lower alkyl, $C_{5-6}$ cycloalkyl, lower alkenyl, amino(lower) alkyl, lower alkoxy-carbonyl amino (lower) alkyl, carboxy (lower) alkyl, sulfo (lower) alkyl, phenyl, mono to tri halo substituted phenyl, and lower alkyl amino (lower) alkyl, $R^6$ is hydrogen, lower alkyl, mono to tri halo (lower) alkyl, lower alkenyl, lower alkynyl, phenyl, tolyl, xylyl, cumenyl, naphthyl, phenyl (lower) alkyl, mono or di halo (lower) alkanoyl, or lower alkoxy, and $R^5$ is carboxy, or pharmaceutically acceptable esterified carboxy, and non-toxic pharmaceutically acceptable salts thereof.

2. A compound of claim 1, wherein $R^1$ is a group of the formula:

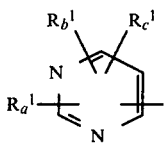

in which $R_a^1$ is amino or acylamino, located at the 2, 4 or 6 position of the ring, acyl being selected from the group consisting of lower alkanoyl, halo (lower) alkanoyl, and lower alkoxycarbonyl, $R_b^1$ and $R_c^1$ are each hydrogen, halogen, lower alkoxy or phenylthio, $R^2$ is hydrogen or lower alkoxy, and $R^4$ is substituted or unsubstituted unsaturated 5 to 6 -membered heterocyclic-thiomethyl the ring atoms of which are 2 or 3 carbon atoms, two nitrogen atoms and one sulfur atom, and the substituent of which is selected from the group consisting of lower alkyl, amino(lower) alkyl and lower alkoxycarbonylamino (lower) alkyl, substituted or unsubstituted unsaturated 5 to 6-membered heterocyclic-thiomethyl the ring atoms of which are 2 or 3 carbon atoms, two nitrogen atoms and one oxygen atom and the substituent of which is halophenyl, substituted or unsubstituted unsaturated 5 to 6-membered heterocyclic-thiomethyl, the ring atoms of which are 1 or 2 carbon atoms and four nitrogen atoms and the subsituent of which is selected from the group consisting of lower alkyl, carboxy (lower) alkyl, lower alkenyl, amino (lower) alkyl and lower alkoxycarbonylamino(lower)alkyl, unsaturated 5 to 6-membered heterocyclic-thiomethyl the ring atoms of which are 3 or 4 carbon atoms and two nitrogen atoms or tetrazolopyridazinyl-thiomethyl, $R^5$ is carboxy or a pharmaceutically acceptable esterified carboxy group, and $R^6$ is hydrogen, lower alkyl, trihalo(lower)alkyl, lower alkenyl, lower alkynyl, phenyl or phenyl(lower)alkyl.

3. A compound of claim 2, wherein $R^1$ is a group of the formula:

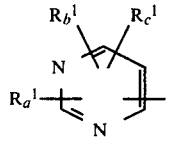

in which $R_a^1$ is amino, lower alkanoyl amino or trihalo(lower) alkanoyl amino, located at the 2, 4 or 6 position of the ring $R_b^1$ and $R_c^1$ are each hydrogen, halogen, lower alkoxy or phenylthio, and $R^2$ is hydrogen or lower alkoxy, $R^4$ is thiadiazolylthiomethyl which is unsubstituted or substituted by a substituent selected from the group consisting of lower alkyl, amino(lower)alkyl and lower alkoxycarbonylamino(lower)alkyl, halophenyloxadiazolylthiomethyl, tetrazolylthiomethyl which is unsubstituted or substituted by a substituent selected from the groups consisting of lower alkyl, carboxy(lower)alkyl, lower alkenyl, amino(lower alkyl) and lower alkoxycarbonylamino(lower)alkyl, pyrazinylthiomethyl or tetrazolopyridazinylthiomethyl, $R^5$ is carboxy, nitrophenyl(lower)alkoxycarbonyl or diphenyl(lower)alkoxycarbonyl, and $R^6$ is hydrogen, lower alkyl, trihalo(lower)alkyl, lower alkenyl, lower alkynyl, phenyl or phenyl(lower)alkyl.

4. A compound of claim 3, wherein $R^1$ is a group of the formula:

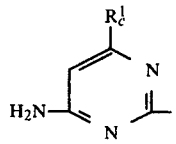

in which $R_c^1$ is hydrogen, halogen, lower alkoxy or phenylthio and $R^2$ is hydrogen.

5. A compound of claim 4, wherein $R^5$ is carboxy.

6. A compound of claim 5, wherein $R_c^1$ is hydrogen, chloro, methoxy or phenylthio, $R^4$ is 1,3,4-thiadiazol-2-ylthiomethyl, 5-methyl-1,3,4-thiadiazol-2-ylthiomethyl, 5-(4-chlorophenyl)-1,3,4-oxadiazol-2-ylthiomethyl, 1-methyl-1H-tetrazol-5-ylthiomethyl, 1-allyl-1H-tetrazol-5-ylthiomethyl, 2-pyrazinylthiomethyl, tetrazolo[1,5-b]pyridazin-6-ylthiomethyl, or 1-(2-aminoethyl)-1H-tetrazol-5-ylthiomethyl and $R^6$ is a methyl, ethyl, propyl, allyl, benzyl or phenyl.

7. A compound of claim 6, which is 7-[2-(4-aminopyrimidin-2-yl)-2-methoxyiminoacetamido]-3-(1,3,4-thiadiazol-2-yl)thiomethyl-3-cephem-4-carboxylic acid (syn isomer).

8. A compound of claim 6, which is 7-[2-(4-aminopyrimidin-2-yl)-2-ethoxyiminoacetamido]-3-(1,3,4-thiadiazol-2-yl)thiomethyl-3-cephem-4-carboxylic acid (syn isomer).

9. A compound of claim 6, which is 7-[2-(4-aminopyridin-2-yl)-2-propoxyiminoacetamido]-3-(1,3,4-thiadiazol-2-yl)thiomethyl-3-cephem-4-carboxylic acid (syn isomer).

10. A compound of claim 6, which is 7-[2-(4-aminopyrimidin-2-yl)-2-allyloxyiminoacetamido]-3-(1,3,4-thiadiazol-2-yl)thiomethyl-3-cephem-4-carboxylic acid (syn isomer).

11. A compound of claim 6, which is 7-[2-(4-aminopyrimidin-2-yl)-2-methoxyiminoacetamido]-3-(5-methyl-1,3,4-thiadiazol-2-yl)-thiomethyl-3-cephem-4-carboxylic acid (syn isomer).

12. A compound of claim 6, which is 7-[2-(4-aminopyrimidin-2-yl)-2-methoxyiminoacetamido]-3-(1-methyl-1H-tetrazol-b 5-yl)thiomethyl-3-cephem-4-carboxylic acid (syn isomer).

13. A compound of claim 6, which is 7-[2-(4-aminopyrimidin-2-yl)-2-methoxyiminoacetamido]-3-(1-allyl-1H-tetrazol-5-yl)thiomethyl-3-cephem-4-carboxylic acid (syn isomer).

14. A compound of claim 6, which is 7-[2-(4-aminopyrimidin-2-yl)-2-methoxyiminoacetamido]-3-(tetrazolo[1,5-b]pyridazin-6-yl)-thiomethyl-3-cephem-4-carboxylic acid (syn isomer).

15. A compound of claim 3 wherein $R^1$ is a group of the formula:

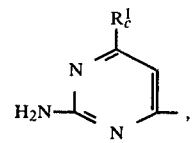

in which $R_c^1$ is hydrogen or halogen, $R^2$ is hydrogen, $R^4$ is tetrazolylthiomethyl having a lower alkyl, $R^5$ is carboxy and $R^6$ is lower alkyl.

16. A compond of claim 15, wherein $R_c^1$ is hydrogen or chloro, $R^4$ is 1-methyl-1H-tetrazol-5-ylthiomethyl and $R^6$ is methyl.

17. A compound of claim 3, wherein $R^1$ is a group of the formula:

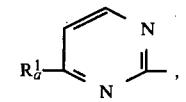

in which $R_a^1$ is lower alkanoylamino, and $R^2$ is hydrogen.

18. A compound of claim 17, wherein $R_a^1$ is formamido, $R^4$ is, 1,3,4-thiadiazol-2-ylthiomethyl, 1-methyl-1H-tetrazol-5-ylthiomethyl or tetrazolo[1,5-b]pyridazin-6-yl thiomethyl $R^5$ is carboxy and $R^6$ is methyl, ethyl, propyl, allyl or benzyl.

19. A compound of claim 3, wherein $R^1$ is a group of the formula:

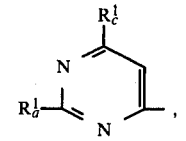

in which $R_a^1$ is lower alkanoylamino and $R_c^1$ is hydrogen or halogen, and $R^2$ is hydrogen.

20. A compound of claim 19, wherein $R_a^1$ is formamido, $R_c^1$ is hydrogen or chloro, $R^4$ is 1-methyl-1H-tetrazol-5-ylthiomethyl, $R^5$ is carboxy and $R^6$ is methyl.

21. A compound according to claim 6, which is 7-[2-(4-aminopyrimidin-2-yl)-2-methoxyiminoacetamido]-3-[1-(2-aminoethyl)-1H-tetrazol-5-ylthiomethyl]-3-cephem-4-carboxylic acid (syn isomer).

22. A compound according to claim 6, which is 7-[2-(4-aminopyrimidin-2-yl)-2-phenoxyiminoacetamido]-3-[1-(2-aminoethyl)-1H-tetrazol-5-ylthiomethyl]-3-cephem-4-carboxylic acid (syn isomer).

23. A compound according to claim 6, which is 7-[2-(4-aminopyrimidin-2-yl)-2-phenoxyiminoacetamido]-3-(1,3,4-thiadiazol-2-ylthiomethyl)-3-cephem-4-carboxylic acid (syn isomer).

24. A pharmaceutical antibacterial composition comprising, as an active ingredient, the compound of claim 1 in association with a non-toxic, pharmaceutically acceptable carrier or excipient.

25. A method for treating an infectious disease caused by pathogens, which comprises internally administering the compound of claim 1 to infected human beings.

* * * * *